US009149038B2

(12) United States Patent
Eckelbarger et al.

(10) Patent No.: US 9,149,038 B2
(45) Date of Patent: Oct. 6, 2015

(54) 4-AMINO-6-(HETEROCYCLIC)PICOLINATES AND 6-AMINO-2-(HETEROCYCLIC) PYRIMIDINE-4-CARBOXYLATES AND THEIR USE AS HERBICIDES

(71) Applicant: Dow AgroSciences LLC, Indianapolis, IN (US)

(72) Inventors: Joseph D. Eckelbarger, Carmel, IN (US); Jeffrey B. Epp, Noblesville, IN (US); Lindsey G. Fischer, Indianapolis, IN (US); Christian T. Lowe, Westfield, IN (US); Jeff Petkus, Indianapolis, IN (US); Joshua Roth, Carmel, IN (US); Norbert M. Satchivi, Carmel, IN (US); Paul R. Schmitzer, Indianapolis, IN (US); Thomas L. Siddall, Zionsville, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 14/205,883

(22) Filed: Mar. 12, 2014

(65) Prior Publication Data

US 2014/0274701 A1 Sep. 18, 2014

Related U.S. Application Data

(60) Provisional application No. 61/790,391, filed on Mar. 15, 2013.

(51) Int. Cl.
| *A01N 41/10* | (2006.01) |
| *A01N 43/54* | (2006.01) |
| *A01N 43/40* | (2006.01) |
| *C07D 405/04* | (2006.01) |
| *A01N 43/90* | (2006.01) |
| *A01N 43/80* | (2006.01) |
| *C07D 411/04* | (2006.01) |
| *C07D 409/04* | (2006.01) |
| *C07D 403/04* | (2006.01) |

(52) U.S. Cl.
CPC ............... *A01N 43/54* (2013.01); *A01N 43/40* (2013.01); *A01N 41/10* (2013.01); *A01N 43/80* (2013.01); *A01N 43/90* (2013.01); *C07D 403/04* (2013.01); *C07D 405/04* (2013.01); *C07D 409/04* (2013.01); *C07D 411/04* (2013.01)

(58) Field of Classification Search
CPC .. C07D 411/04; C07D 409/04; C07D 407/04; C07D 403/04; C07D 405/04; A01N 41/10; A01N 43/08; A01N 43/90
USPC .................. 514/256, 336, 337, 339; 544/329; 546/283.7, 284.1, 277.4, 280.4, 280.7
See application file for complete search history.

(56) References Cited

U.S. PATENT DOCUMENTS

| 6,784,137 B2 * | 8/2004 | Balko et al. ................... 504/244 |
| 7,300,907 B2 * | 11/2007 | Epp et al. ...................... 504/239 |
| 7,314,849 B2 * | 1/2008 | Balko et al. ................... 504/244 |
| 7,498,468 B2 * | 3/2009 | Balko et al. ....................... 568/1 |
| 7,538,214 B2 * | 5/2009 | Epp et al. ...................... 544/329 |
| 7,642,220 B2 * | 1/2010 | Epp et al. ...................... 504/239 |
| 7,888,287 B2 * | 2/2011 | Epp et al. ...................... 504/239 |
| 8,288,318 B2 * | 10/2012 | Epp et al. ...................... 504/239 |
| 8,426,591 B2 * | 4/2013 | Guenthensperger et al. ............................. 544/319 |
| 8,536,331 B2 * | 9/2013 | Eckelbarger et al. ......... 544/329 |
| 8,609,592 B2 * | 12/2013 | Guenthensperger et al. ............................. 504/239 |
| 8,754,229 B2 * | 6/2014 | Epp et al. ...................... 546/290 |
| 2003/0114311 A1 | 6/2003 | Balko et al. |
| 2008/0045734 A1 | 2/2008 | Balko et al. |
| 2008/0234262 A1 | 9/2008 | Zask et al. |
| 2009/0088322 A1 | 4/2009 | Epp et al. |
| 2009/0264429 A1 | 10/2009 | Apodaca et al. |
| 2010/0137137 A1 | 6/2010 | Rosinger et al. |
| 2010/0179127 A1 | 7/2010 | Floersheim et al. |
| 2011/0136666 A1 | 6/2011 | Whittingham et al. |
| 2011/0281873 A1 | 11/2011 | Chiang et al. |
| 2012/0115724 A1 * | 5/2012 | Whittingham et al. ....... 504/128 |
| 2012/0190549 A1 | 7/2012 | Eckelbarger et al. |
| 2012/0288492 A1 * | 11/2012 | Kuo et al. .................. 424/130.1 |
| 2012/0295905 A1 | 11/2012 | Witty et al. |
| 2013/0310358 A1 | 11/2013 | Coats et al. |
| 2013/0345240 A1 | 12/2013 | Whitten et al. |

FOREIGN PATENT DOCUMENTS

| CA | 2842830 | 1/2013 |
| WO | WO 03011853 A1 * | 2/2003 |
| WO | WO 2005063721 A1 * | 7/2005 |
| WO | WO 2006121648 A2 * | 11/2006 |
| WO | 2007/082076 | 7/2007 |
| WO | 2007/082098 | 7/2007 |

(Continued)

OTHER PUBLICATIONS

L. M. Abell et al. Target-Site Directed Herbicide Design in, Pest Control With Enhanced Environmental Safety 15-37 (ACS Symposium Series; American Chemical Society, S. Duke, et al. eds, 1993).*
S.C. Knight et al., Annual Review of Phytopathology 35, 349-372, 357 (1997).*
W.T. Ruegg et al., Weed Research, 47(4), 271-275, 271 (2006).*
International Search Report and Written Opinion, dated Jul. 7, 2014, in International Application No. PCT/US2014/024745, (9 pages).
International Search Report and Written Opinion, dated Jul. 10, 2014, in International Application No. PCT/US2014/024749, (9 pages).

(Continued)

*Primary Examiner* — Alexander R Pagano
(74) *Attorney, Agent, or Firm* — Michael J. Terapane; Meunier Carlin & Curfman, LLC

(57) ABSTRACT

Novel 4-amino-6-(heterocyclic)picolinic acids and their derivatives and 6-amino-2-(heterocyclic)pyrimidine-4-carboxylates and their derivatives are useful to control undesirable vegetation.

19 Claims, No Drawings

(56) References Cited

FOREIGN PATENT DOCUMENTS

| WO | 2009/023438 | | 2/2009 |
| WO | WO 2009029735 | A1 * | 3/2009 |
| WO | 2009/081112 | | 7/2009 |
| WO | 2009/138712 | | 11/2009 |
| WO | WO 2010092339 | A1 * | 8/2010 |
| WO | WO 2011080568 | A2 * | 7/2011 |
| WO | WO 2012080187 | A1 * | 6/2012 |
| WO | 2012/149528 | | 11/2012 |
| WO | 2013/014165 | | 1/2013 |
| WO | WO 2013003740 | A1 * | 1/2013 |

OTHER PUBLICATIONS

International Search Report and Written Opinion, dated Jul. 7, 2014, in International Application No. PCT/US2014/024752, (9 pages).

* cited by examiner

4-AMINO-6-(HETEROCYCLIC)PICOLINATES AND 6-AMINO-2-(HETEROCYCLIC) PYRIMIDINE-4-CARBOXYLATES AND THEIR USE AS HERBICIDES

CROSS REFERENCE TO RELATED APPLICATIONS

This application claims the benefit of U.S. Provisional Patent Application Ser. No. 61/790,391 filed Mar. 15, 2013, the disclosure of which is expressly incorporated herein by reference.

FIELD

The invention relates to herbicidal compounds and compositions and to methods for controlling undesirable vegetation.

BACKGROUND

The occurrence of undesirable vegetation, e.g., weeds, is a constant problem facing farmers in crops, pasture, and other settings. Weeds compete with crops and negatively impact crop yield. The use of chemical herbicides is an important tool in controlling undesirable vegetation.

There remains a need for new chemical herbicides that offer a broader spectrum of weed control, selectivity, minimal crop damage, storage stability, ease of handling, higher activity against weeds, and/or a means to address herbicide-tolerance that develops with respect to herbicides currently in use.

SUMMARY OF THE INVENTION

Provided herein are compounds of Formula (I):

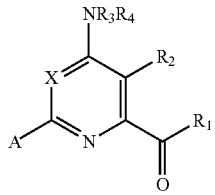

(I)

wherein
X is N or CY, wherein Y is hydrogen, halogen, $C_1$-$C_3$ alkyl, $C_1$-$C_3$ haloalkyl, $C_1$-$C_3$ alkoxy, $C_1$-$C_3$ haloalkoxy, $C_1$-$C_3$ alkoxy, $C_1$-$C_3$ alkylthio or $C_1$-$C_3$ haloalkylthio;

$R^1$ is $OR^{1'}$ or $NR^{1''}R^{1'''}$, wherein $R^{1'}$ is hydrogen, $C_1$-$C_8$ alkyl, or $C_7$-$C_{10}$ arylalkyl, and $R^{1''}$ and $R^{1'''}$ are independently hydrogen, $C_1$-$C_{12}$ alkyl, $C_3$-$C_{12}$ alkenyl, or $C_3$-$C_{12}$ alkynyl;

$R^2$ is halogen, $C_1$-$C_4$ alkyl, $C_1$-$C_4$ haloalkyl, $C_2$-$C_4$ alkenyl, $C_2$-$C_4$ haloalkenyl, $C_2$-$C_4$ alkynyl, $C_1$-$C_4$ alkoxy, $C_1$-$C_4$ haloalkoxy, $C_1$-$C_4$ alkylthio, $C_1$-$C_4$ haloalkylthio, amino, $C_1$-$C_4$ alkylamino, $C_2$-$C_4$ haloalkylamino, formyl, $C_1$-$C_3$ alkylcarbonyl, $C_1$-$C_3$ haloalkylcarbonyl, cyano, or a group of the formula —$CR^{17}$=$CR^{18}$—$SiR^{19}R^{20}R^{21}$, wherein $R^{17}$ is hydrogen, F, or Cl; $R^{18}$ is hydrogen, F, Cl, $C_1$-$C_4$ alkyl, or $C_1$-$C_4$ haloalkyl; and $R^{19}$, $R^{20}$, and $R^{21}$ are independently $C_1$-$C_{10}$ alkyl, $C_3$-$C_6$ cycloalkyl, phenyl, substituted phenyl, $C_1$-$C_{10}$ alkoxy, or OH;

$R^3$ and $R^4$ are independently hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, $C_1$-$C_6$ trialkylsilyl, $C_1$-$C_6$ dialkylphosphonyl, or $R^3$ and $R^4$ taken together with N is a 5- or 6 membered saturated ring, or $R^3$ and $R^4$ taken together represent =$CR^{3'}(R^{4'})$, wherein $R^{3'}$ and $R^{4'}$ are independently hydrogen, $C_1$-$C_6$ alkyl, $C_3$-$C_6$ alkenyl, $C_3$-$C_6$ alkynyl, $C_1$-$C_6$ alkoxy or $C_1$-$C_6$ alkylamino, or, $R^{3'}$ and $R^{4'}$ taken together with =C represent a 5- or 6-membered saturated ring;

A is one of groups Ar1 to Ar24:

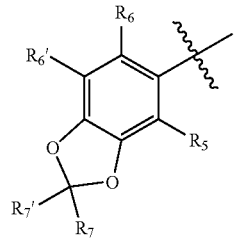

Ar1

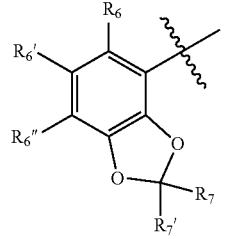

Ar2

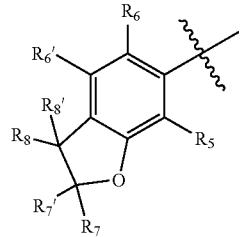

Ar3

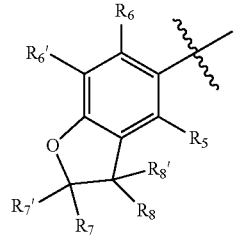

Ar4

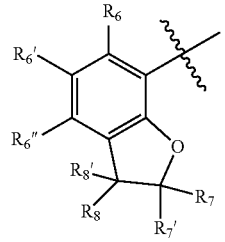

Ar5

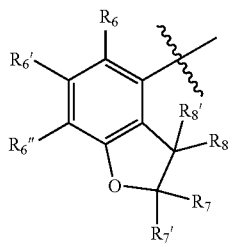 Ar6
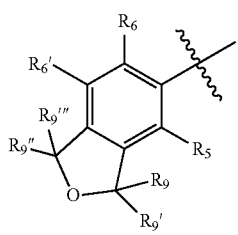 Ar7
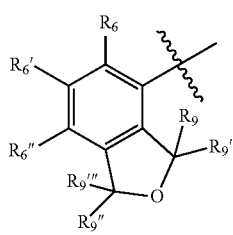 Ar8
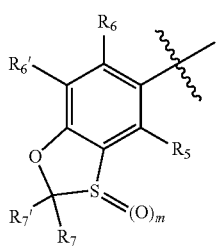 Ar9
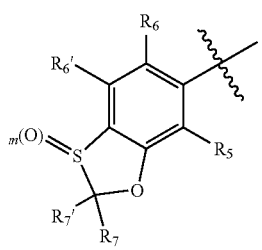 Ar10
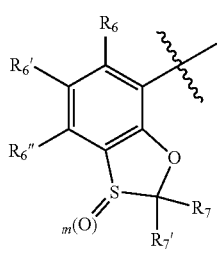 Ar11
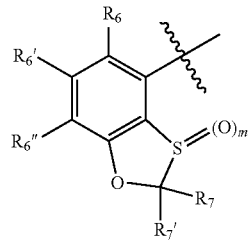 Ar12
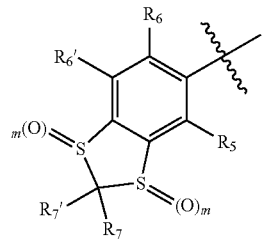 Ar13
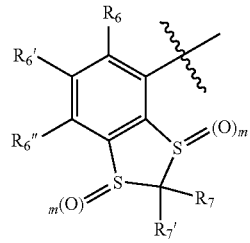 Ar14
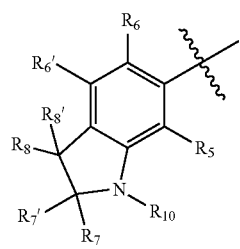 Ar15
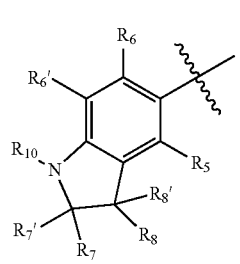 Ar16
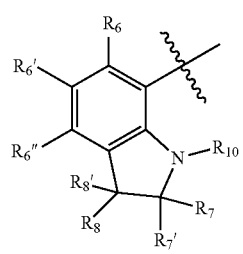 Ar17

Ar18 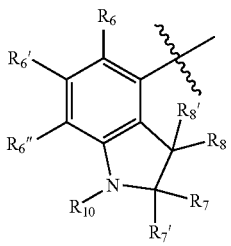

Ar19 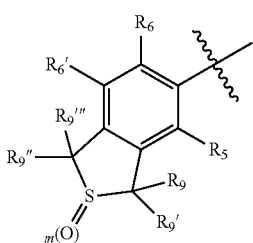

Ar20 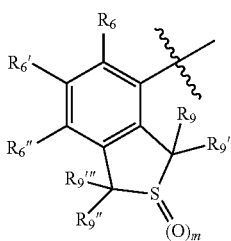

Ar21 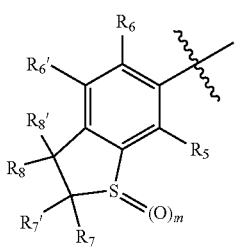

Ar22 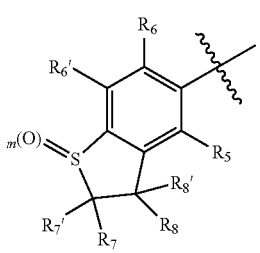

Ar23 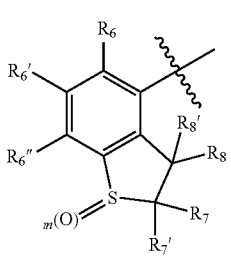

Ar24 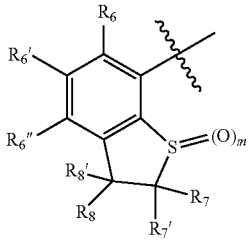

$R^5$ is hydrogen, halogen, $C_1$-$C_4$ alkyl, $C_1$-$C_4$ haloalkyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino, or $C_2$-$C_4$ haloalkylamino.

$R^6$ is hydrogen, halogen, $C_1$-$C_4$ alkyl, $C_1$-$C_4$ haloalkyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino, or $C_2$-$C_4$ haloalkylamino;

$R^{6'}$ is hydrogen or halogen;

$R^{6''}$ is hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino, $C_2$-$C_4$ haloalkylamino, CN or $NO_2$;

$R^7$ and $R^{7'}$ are independently hydrogen, halogen, $C_1$-$C_4$ alkyl, $C_1$-$C_4$ haloalkyl, or $C_1$-$C_3$ alkoxy;

$R^8$ and $R^{8'}$ are independently hydrogen, halogen, $C_1$-$C_4$ alkyl, $C_1$-$C_4$ haloalkyl, or $C_1$-$C_3$ alkoxy;

$R^9$, $R^{9'}$, $R^{9''}$ and $R^{9'''}$ are independently hydrogen, halogen, $C_1$-$C_4$ alkyl, $C_1$-$C_4$ haloalkyl, or $C_1$-$C_3$ alkoxy;

$R^{10}$ is hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, or $C_1$-$C_6$ trialkylsilyl;

m, when present, is 0, 1, or 2; and n, when present, is 0, 1, or 2;

or N-oxide or an agriculturally acceptable salt thereof;

provided A is not

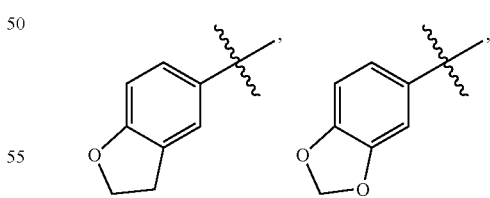

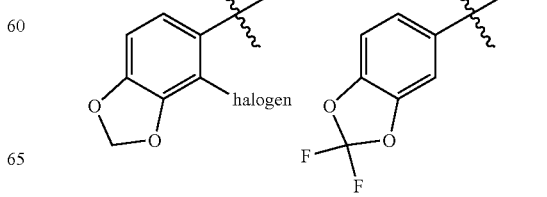

-continued

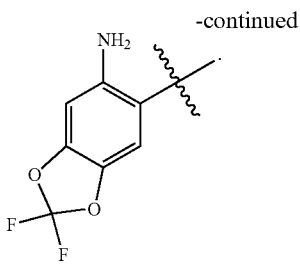

Also provided are methods of controlling undesirable vegetation which comprises applying a compound of Formula (I) or an N-oxide or an agriculturally acceptable salt thereof.

DETAILED DESCRIPTION

Definitions

As used herein, herbicide and herbicidal active ingredient mean a compound that controls undesirable vegetation when applied in an appropriate amount.

As used herein, control of or controlling undesirable vegetation means killing or preventing the vegetation, or causing some other adversely modifying effect to the vegetation e.g., deviations from natural growth or development, regulation, desiccation, retardation, and the like.

As used herein, a herbicidally effective or vegetation controlling amount is an amount of herbicidal active ingredient the application of which controls the relevant undesirable vegetation.

As used herein, applying a herbicide or herbicidal composition means delivering it directly to the targeted vegetation or to the locus thereof or to the area where control of undesired vegetation is desired. Methods of application include, but are not limited to pre-emergently contacting soil or water, post-emergently contacting the undesirable vegetation or area adjacent to the undesirable vegetation.

As used herein, plants and vegetation include, but are not limited to, dormant seeds, germinant seeds, emerging seedlings, plants emerging from vegetative propagules, immature vegetation, and established vegetation.

As used herein, agriculturally acceptable salts and esters refer to salts and esters that exhibit herbicidal activity, or that are or can be converted in plants, water, or soil to the referenced herbicide. Exemplary agriculturally acceptable esters are those that are or can by hydrolyzed, oxidized, metabolized, or otherwise converted, e.g., in plants, water, or soil, to the corresponding carboxylic acid which, depending on the pH, may be in the dissociated or undissociated form.

Suitable salts include those derived from alkali or alkaline earth metals and those derived from ammonia and amines. Preferred cations include sodium, potassium, magnesium, and aminium cations of the formula:

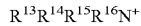

wherein $R^{13}$, $R^{14}$, $R^{15}$ and $R^{16}$ each, independently represents hydrogen or $C_1$-$C_{12}$ alkyl, $C_3$-$C_{12}$ alkenyl or $C_3$-$C_{12}$ alkynyl, each of which is optionally substituted by one or more hydroxy, $C_1$-$C_4$ alkoxy, $C_1$-$C_4$ alkylthio or phenyl groups, provided that $R^{13}$, $R^{14}$, $R^{15}$ and $R^{16}$ are sterically compatible. Additionally, any two $R^{13}$, $R^{14}$, $R^{15}$ and $R^{16}$ together may represent an aliphatic difunctional moiety containing one to twelve carbon atoms and up to two oxygen or sulfur atoms. Salts of the compounds of Formula (I) can be prepared by treatment of compounds of Formula (I) with a metal hydroxide, such as sodium hydroxide, with an amine, such as ammonia, trimethylamine, diethanolamine, 2-methylthiopropylamine, bisallylamine, 2-butoxyethylamine, morpholine, cyclododecylamine, or benzylamine or with a tetraalkylammonium hydroxide, such as tetramethylammonium hydroxide or choline hydroxide. Amine salts are often preferred forms of the compounds of Formula (I) because they are water-soluble and lend themselves to the preparation of desirable aqueous based herbicidal compositions.

Compounds of the Formula (I) include N-oxides. Pyridine N-oxides can be obtained by oxidation of the corresponding pyridines. Suitable oxidation methods are described, for example, in Houben-Weyl, *Methoden der organischen Chemie [Methods in organic chemistry]*, expanded and subsequent volumes to the 4th edition, volume E 7b, p. 565f.

As used herein, unless otherwise specified, acyl refers to formyl, $C_1$-$C_3$ alkylcarbonyl, and $C_1$-$C_3$ haloalkylcarbonyl. $C_1$-$C_6$ acyl refers to formyl, $C_1$-$C_5$ alkylcarbonyl, and $C_1$-$C_5$ haloalkylcarbonyl (the group contains a total of 1 to 6 carbon atoms).

As used herein, alkyl refers to saturated, straight-chained or branched saturated hydrocarbon moieties. Unless otherwise specified, $C_1$-$C_{10}$ alkyl groups are intended. Examples include methyl, ethyl, propyl, 1-methyl-ethyl, butyl, 1-methyl-propyl, 2-methyl-propyl, 1,1-dimethyl-ethyl, pentyl, 1-methyl-butyl, 2-methyl-butyl, 3-methyl-butyl, 2,2-dimethyl-propyl, 1-ethyl-propyl, hexyl, 1,1-dimethyl-propyl, 1,2-dimethyl-propyl, 1-methyl-pentyl, 2-methyl-pentyl, 3-methyl-pentyl, 4-methyl-pentyl, 1,1-dimethyl-butyl, 1,2-dimethyl-butyl, 1,3-dimethyl-butyl, 2,2-dimethyl-butyl, 2,3-dimethyl-butyl, 3,3-dimethyl-butyl, 1-ethyl-butyl, 2-ethyl-butyl, 1,1,2-trimethyl-propyl, 1,2,2-trimethyl-propyl, 1-ethyl-1-methyl-propyl, and 1-ethyl-2-methyl-propyl.

As used herein, "haloalkyl" refers to straight-chained or branched alkyl groups, where in these groups the hydrogen atoms may partially or entirely be substituted with halogen atoms. Unless otherwise specified, $C_1$-$C_8$ groups are intended. Examples include chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2-difluoroethyl, 2,2-dichloro-2-fluoroethyl, 2,2,2-trichloroethyl, pentafluoroethyl, and 1,1,1-trifluoroprop-2-yl.

As used herein, alkenyl refers to unsaturated, straight-chained, or branched hydrocarbon moieties containing a double bond. Unless otherwise specified, $C_2$-$C_8$ alkenyl are intended. Alkenyl groups may contain more than one unsaturated bond. Examples include ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl, and 1-ethyl-2-methyl-2-propenyl. Vinyl refers to a group having the structure —CH=CH$_2$; 1-propenyl refers to a group with the structure -CH=CH—CH$_3$; and 2-propenyl refers to a group with the structure —CH$_2$—CH=CH$_2$.

As used herein, alkynyl represents straight-chained or branched hydrocarbon moieties containing a triple bond. Unless otherwise specified, $C_2$-$C_8$ alkynyl groups are intended. Alkynyl groups may contain more than one unsaturated bond. Examples include $C_2$-$C_6$-alkynyl, such as ethynyl, 1-propynyl, 2-propynyl (or propargyl), 1-butynyl, 2-butynyl, 3-butynyl, 1-methyl-2-propynyl, 1-pentynyl, 2-pentynyl, 3-pentynyl, 4-pentynyl, 3-methyl-1-butynyl, 1-methyl-2-butynyl, 1-methyl-3-butynyl, 2-methyl-3-butynyl, 1,1-dimethyl-2-propynyl, 1-ethyl-2-propynyl, 1-hexynyl, 2-hexynyl, 3-hexynyl, 4-hexynyl, 5-hexynyl, 3-methyl-1-pentynyl, 4-methyl-1-pentynyl, 1-methyl-2-pentynyl, 4-methyl-2-pentynyl, 1-methyl-3-pentynyl, 2-methyl-3-pentynyl, 1-methyl-4-pentynyl, 2-methyl-4-pentynyl, 3-methyl-4-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl, and 1-ethyl-1-methyl-2-propynyl.

As used herein, alkoxy refers to a group of the formula R—O—, where R is alkyl as defined above. Unless otherwise specified, alkoxy groups wherein R is a $C_1$-$C_8$ alkyl group are intended. Examples include methoxy, ethoxy, propoxy, 1-methyl-ethoxy, butoxy, 1-methyl-propoxy, 2-methyl-propoxy, 1,1-dimethyl-ethoxy, pentoxy, 1-methyl-butyloxy, 2-methyl-butoxy, 3-methyl-butoxy, 2,2-dimethyl-propoxy, 1-ethyl-propoxy, hexoxy, 1,1-dimethyl-propoxy, 1,2-dimethyl-propoxy, 1-methyl-pentoxy, 2-methyl-pentoxy, 3-methyl-pentoxy, 4-methyl-penoxy, 1,1-dimethyl-butoxy, 1,2-dimethyl-butoxy, 1,3-dimethyl-butoxy, 2,2-dimethyl-butoxy, 2,3-dimethyl-butoxy, 3,3-dimethyl-butoxy, 1-ethyl-butoxy, 2-ethylbutoxy, 1,1,2-trimethyl-propoxy, 1,2,2-trimethyl-propoxy, 1-ethyl-1-methyl-propoxy, and 1-ethyl-2-methyl-propoxy.

As used herein, haloalkoxy refers to a group of the formula R—O—, where R is haloalkyl as defined above. Unless otherwise specified, haloalkoxy groups wherein R is a $C_1$-$C_8$ alkyl group are intended. Examples include chloromethoxy, bromomethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-chloroethoxy, 1-bromoethoxy, 1-fluoroethoxy, 2-fluoroethoxy, 2,2-difluoroethoxy, 2,2,2-trifluoroethoxy, 2-chloro-2-fluoroethoxy, 2-chloro-2-difluoroethoxy, 2,2-dichloro-2-fluoroethoxy, 2,2,2-trichloroethoxy, pentafluoroethoxy, and 1,1,1-trifluoroprop-2-oxy.

As used herein, alkylthio refers to a group of the formula R—S— where R is alkyl as defined above. Unless otherwise specified, alkylthio groups wherein R is a $C_1$-$C_8$ alkyl group are intended. Examples include methylthio, ethylthio, propylthio, 1-methylethylthio, butylthio, 1-methyl-propylthio, 2-methylpropylthio, 1,1-dimethylethylthio, pentylthio, 1-methylbutylthio, 2-methylbutylthio, 3-methylbutylthio, 2,2-dimethylpropylthio, 1-ethylpropylthio, hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio, and 1-ethyl-2-methylpropylthio.

As used herein, haloalkylthio refers to an alkylthio group as defined above wherein the carbon atoms are partially or entirely substituted with halogen atoms. Unless otherwise specified, haloalkylthio groups wherein R is a $C_1$-$C_8$ alkyl group are intended. Examples include chloromethylthio, bromomethylthio, dichloromethylthio, trichloromethylthio, fluoromethylthio, difluoromethylthio, trifluoromethylthio, chlorofluoromethylthio, dichlorofluoromethylthio, chlorodifluoromethylthio, 1-chloroethylthio, 1-bromoethylthio, 1-fluoroethylthio, 2-fluoroethylthio, 2,2-difluoroethylthio, 2,2,2-trifluoroethylthio, 2-chloro-2-fluoroethylthio, 2-chloro-2-difluoroethylthio, 2,2-dichloro-2-fluoroethylthio, 2,2,2-trichloroethylthio, pentafluoroethylthio, and 1,1,1-trifluoroprop-2-ylthio.

As used herein, aryl, as well as derivative terms such as aryloxy, refers to a phenyl, indanyl or naphthyl group with phenyl being preferred. The term "heteroaryl", as well as derivative terms such as "heteroaryloxy", refers to a 5- or 6-membered aromatic ring containing one or more heteroatoms, viz., N, O or S; these heteroaromatic rings may be fused to other aromatic systems. The aryl or heteroaryl substituents may be unsubstituted or substituted with one or more substituents selected from halogen, hydroxy, nitro, cyano, formyl, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_1$-$C_6$ haloalkoxy, $C_1$-$C_6$ acyl, $C_1$-$C_6$ alkylthio, $C_1$-$C_6$ alkylsulfinyl, $C_1$-$C_6$ alkylsulfonyl, $C_1$-$C_6$ alkoxycarbonyl, $C_1$-$C_6$ carbamoyl, hydroxycarbonyl, $C_1$-$C_6$ alkylcarbonyl, aminocarbonyl, $C_1$-$C_6$ alkylaminocarbonyl, $C_1$-$C_6$ dialkylaminocarbonyl, provided that the substituents are sterically compatible and the rules of chemical bonding and strain energy are satisfied. Preferred substituents include halogen, $C_1$-$C_2$ alkyl and $C_1$-$C_2$ haloalkyl.

As used herein alkylcarbonyl refers to an alkyl group bonded to a carbonyl group. $C_1$-$C_3$ alkylcarbonyl and $C_1$-$C_3$ haloalkylcarbonyl refer to groups wherein a $C_1$-$C_3$ alkyl group is bonded to a carbonyl group (the group contains a total of 2 to 4 carbon atoms).

As used herein, alkoxycarbonyl refers to a group of the formula

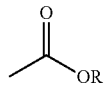

wherein R is alkyl.

As used herein, arylalkyl refers to an alkyl group substituted with an aryl group. $C_7$-$C_{10}$ arylalkyl refers to a group wherein the total number of carbon atoms in the group is 7 to 10.

As used herein alkylamino refers to an amino group substituted with one or two alkyl groups, which may be the same or different.

As used herein haloalkylamino refers to an alkylamino group wherein the alkyl carbon atoms are partially or entirely substituted with halogen atoms.

As used herein, $C_1$-$C_6$ alkylaminocarbonyl refers to a group of the formula RNHC(O)— wherein R is $C_1$-$C_6$ alkyl, and $C_1$-$C_6$ dialkylaminocarbonyl refers to a group of the formula $R_2$NC(O)— wherein each R is independently $C_1$-$C_6$ alkyl.

As used herein alkylcarbamyl refers to a carbamyl group substituted on the nitrogen with an alkyl group.

As used herein alkylsulfonyl refers to a group of the formula

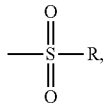

where R is alkyl.

As used herein carbamyl (also referred to as carbamoyl and aminocarbonyl) refers to a group of the formula

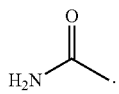

As used herein dialkylphosphonyl refers to a group of the formula

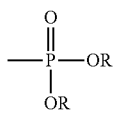

where R is independently alkyl in each occurrence.

As used herein, $C_1$-$C_6$ trialkylsilyl refers to a group of the formula —$SiR_3$ wherein each R is independently a $C_1$-$C_6$ alkyl group (the group contains a total of 3 to 18 carbon atoms).

As used herein Me refers to a methyl group; OMe refers to a methoxy group; i-Pr refers to an isopropyl group.

As used herein, the term "halogen" including derivative terms such as "halo" refers to fluorine, chlorine, bromine and iodine.

As used herein, plants and vegetation include, but are not limited to, germinant seeds, emerging seedlings, plants emerging from vegetative propagules, immature vegetation, and established vegetation.

Compounds of Formula (I)

The invention provides compounds of Formula (I) as defined above and N-oxides and agriculturally acceptable salts thereof.

In some embodiments, the compound is the carboxylic acid or an agriculturally acceptable ester or salt. In some embodiments, the compound is the carboxylic acid or its methyl ester.

In some embodiments, $R^2$ is halogen, $C_2$-$C_4$-alkenyl, $C_2$-$C_4$-haloalkenyl, or $C_1$-$C_4$-alkoxy. In some embodiments, $R^2$ is halogen, $C_2$-$C_4$-alkenyl, or $C_1$-$C_4$-alkoxy. In some embodiments, $R^2$ is Cl, OMe, vinyl, or 1-propenyl. In some embodiments, $R^2$ is Cl. In some embodiments, $R^2$ is OMe. In some embodiments $R^2$ is vinyl or 1-propenyl.

In some embodiments, $R^3$ and $R^4$ are independently hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, or $R^3$ and $R^4$ taken together represent =$CR^{3'}(R^{4'})$, wherein $R^{3'}$ and $R^{4'}$ are independently hydrogen, $C_1$-$C_6$ alkyl, $C_3$-$C_6$ alkenyl, $C_3$-$C_6$ alkynyl, $C_1$-$C_6$ alkoxy, or $C_1$-$C_6$ alkylamino. In some embodiments, $R^3$ and $R^4$ are independently hydrogen, $C_1$-$C_6$ alkyl, $C_1$-$C_6$ haloalkyl, $C_3$-$C_6$ alkenyl, $C_3$-$C_6$ haloalkenyl, formyl, $C_1$-$C_3$ alkylcarbonyl, $C_1$-$C_3$ haloalkylcarbonyl, or $R^3$ and $R^4$ taken together represent =$CR^{3'}(R^{4'})$, wherein $R^{3'}$ and $R^{4'}$ are independently hydrogen, $C_1$-$C_6$ alkyl, $C_1$-$C_6$ alkoxy, or $C_1$-$C_6$ alkylamino. In some embodiments, at least one of $R^3$ and $R^4$ are hydrogen. In some embodiments, $R^3$ and $R^4$ are both hydrogen.

In some embodiments, m, when present, is 0 or 1; and n, when present, is 0 or 1. In certain embodiments, m, when present, is 0; and n, when present, is 0. In certain embodiments, m, when present, is 1; and n, when present, is 1

In some embodiments, X is N, CH, or CF. In some embodiments, X is N. In some embodiments, X is CH. In some embodiments, X is CF.

In some embodiments: Ar is Ar1, Ar3, Ar7, Ar9, Ar10, Ar13, Ar15, Ar16, Ar19, Ar21, or Ar22.

In some embodiments: Ar is Ar2, Ar4, Ar5, Ar6, Ar8, Ar11, Ar12, Ar14, Ar17, Ar18, Ar20, Ar23, or Ar24.

In some embodiments: Ar is Ar1, Ar2, Ar3, Ar4, Ar6, or Ar7.

In some embodiments: Ar is Ar15, Ar16, Ar17, or Ar18.

In some embodiments, $R^5$ is hydrogen, halogen, $C_1$-$C_4$ alkyl, $C_1$-$C_4$ haloalkyl, or $C_1$-$C_3$ alkoxy. In some embodiments, $R^5$ is hydrogen or F. In some embodiments, $R^5$ is hydrogen. In some embodiments, $R^5$ is F.

In some embodiments, $R^6$ is hydrogen or halogen. In some embodiments, $R^6$ is hydrogen or F. In some embodiments, $R^6$ is hydrogen. In some embodiments, $R^6$ is F.

In some embodiments, $R^{6'}$ is hydrogen or halogen. In some embodiments, $R^{6'}$ is hydrogen or F. In some embodiments, $R^{6'}$ is hydrogen. In some embodiments, $R^{6'}$ is F.

In some embodiments, $R^{6''}$ is hydrogen, halogen, $C_1$-$C_4$ alkyl, $C_1$-$C_4$ haloalkyl, cyclopropyl, $C_2$-$C_4$ alkynyl, CN, or $NO_2$. In some embodiments, $R^{6''}$ is hydrogen, halogen, $C_1$-$C_4$ haloalkyl, or cyclopropyl. In some embodiments, $R^{6''}$ is hydrogen or halogen. In some embodiments, $R^{6''}$ is $C_1$-$C_4$ haloalkyl. In some embodiments, $R^{6''}$ is CN. In some embodiments, $R^{6''}$ is $NO_2$.

In some embodiments:
$R^2$ is halogen, $C_2$-$C_4$-alkenyl, $C_2$-$C_4$ haloalkenyl, or $C_1$-$C_4$-alkoxy;
$R^3$ and $R^4$ are both hydrogen; and
X is N, CH or CF.

In some embodiments:
$R^2$ is halogen, $C_2$-$C_4$-alkenyl, or $C_1$-$C_4$-alkoxy;
$R^3$ and $R^4$ are both hydrogen; and
X is N, CH, or CF;
Ar is Ar1, Ar3, Ar7, Ar9, Ar10, Ar13, Ar15, Ar16, Ar19, Ar21, or Ar22;
$R^5$ is hydrogen or F;
$R^6$ is hydrogen or F;
$R^{6'}$ is hydrogen;
$R^7$, $R^{7'}$, $R^8$, $R^{8'}$, $R^9$, $R^{9'}$, $R^{9''}$, and $R^{9'''}$, if applicable to the relevant Ar group, are independently hydrogen or fluorine.

In some embodiments:
$R^2$ is chlorine, methoxy, vinyl, or 1-propenyl;
$R^3$ and $R^4$ are hydrogen; and
X is N, CH, or CF.

In some embodiments:
$R^2$ is chlorine;
$R^3$ and $R^4$ are hydrogen; and
X is N, CH, or CF.

In some embodiments:
$R^2$ is methoxy;
$R^3$ and $R^4$ are hydrogen; and
X is N, CH, or CF.

In some embodiments:
$R^2$ is vinyl or 1-propenyl;
$R^3$ and $R^4$ are hydrogen; and
X is N, CH, or CF.
In some embodiments:
$R^2$ is chlorine, methoxy, vinyl, or 1-propenyl;
$R^3$ and $R^4$ are hydrogen; and
X is N.
In some embodiments:
$R^2$ is chlorine;
$R^3$ and $R^4$ are hydrogen; and
X is CH.

In some embodiments:
$R^2$ is chlorine, methoxy, vinyl, or 1-propenyl;
$R^3$ and $R^4$ are hydrogen; and
X is CF.

Exemplary Compounds

The following Table 1 describes exemplary compounds of the Formula (I) wherein
$R^1$ is $OR^{1'}$;
$R^3$ and $R^4$ are hydrogen; and
$R^{1'}$, $R^2$, X, Ar, m, $R^5$, $R^6$, $R^{6'}$, $R^{6''}$, $R^7$, and $R^{7'}$, $R^8$, $R^{8'}$, and $R^{10}$ are one of the following combinations:

TABLE 1

| C. No. | $R^{1'}$ | $R^2$ | X | Ar | m | $R^5$ | $R^6$ | $R^{6'}$ | $R^{6''}$ | $R^7$ | $R^{7'}$ |
|---|---|---|---|---|---|---|---|---|---|---|---|
| 1 | Me | Cl | CCl | Ar1 | | | | | | F | F |
| 2 | Me | Cl | CCl | Ar1 | | | F | | | F | F |
| 3 | H | Cl | CCl | Ar1 | | | F | | | F | F |
| 4 | Me | Cl | CCl | Ar1 | | F | | | | F | F |
| 5 | H | Cl | CCl | Ar1 | | F | | | | F | F |
| 6 | Me | Cl | CF | Ar1 | | | | | | F | F |
| 7 | H | Cl | CF | Ar1 | | | | | | F | F |
| 8 | Me | Cl | CF | Ar1 | | | | | | Me | Me |
| 9 | Me | Cl | CF | Ar1 | | | F | | | F | F |
| 10 | Me | Cl | CF | Ar1 | | F | | | | F | F |
| 11 | H | Cl | CF | Ar1 | | F | | | | F | F |
| 12 | Me | Cl | CF | Ar1 | | | Cl | | | F | F |
| 13 | H | Cl | CF | Ar1 | | | F | | | F | F |
| 14 | Me | Cl | CF | Ar1 | | | | OMe | | | |
| 15 | H | Cl | CF | Ar1 | | | | OMe | | | |
| 16 | Me | Cl | CF | Ar1 | | F | | | | | |
| 17 | Me | Cl | CF | Ar1 | | | F | | | F | F |
| 18 | H | Cl | CF | Ar1 | | | F | | | F | F |
| 19 | H | Cl | CF | Ar1 | | | | | | Me | Me |
| 20 | Me | Cl | CF | Ar1 | | | | | | Me | |
| 21 | Me | F | CF | Ar1 | | | F | | | F | F |
| 22 | Me | OMe | CF | Ar1 | | | F | | | F | F |
| 23 | H | OMe | CF | Ar1 | | | F | | | F | F |
| 24 | Me | OMe | CF | Ar1 | | | | | | F | F |
| 25 | H | OMe | CF | Ar1 | | | | | | F | F |
| 26 | Me | OMe | CF | Ar1 | | | F | | | | |
| 27 | Me | vinyl | CF | Ar1 | | | F | | | F | F |
| 28 | H | vinyl | CF | Ar1 | | | F | | | F | F |
| 29 | Me | Vinyl | CF | Ar1 | | | | | | F | F |
| 30 | H | vinyl | CF | Ar1 | | | | | | F | F |
| 31 | Me | Vinyl | CF | Ar1 | | | F | | | | |
| 32 | Me | Cl | CH | Ar1 | | | F | | | F | F |
| 33 | Me | Cl | CH | Ar1 | | Cl | | | | F | F |
| 34 | H | Cl | CH | Ar1 | | Cl | | | | F | F |
| 35 | Me | Cl | CH | Ar1 | | Me | | | | F | F |
| 36 | H | Cl | CH | Ar1 | | Me | | | | F | F |
| 37 | Me | Cl | CH | Ar1 | | F | | | | F | F |
| 38 | Me | Cl | CH | Ar1 | | | OMe | | | F | F |
| 39 | H | Cl | CH | Ar1 | | | OMe | | | F | F |
| 40 | Me | Cl | CH | Ar1 | | | Cl | | | F | F |
| 41 | H | Cl | CH | Ar1 | | F | | | | F | F |
| 42 | H | Cl | CH | Ar1 | | | F | | | F | F |
| 43 | Me | Cl | CH | Ar1 | | | | F | | F | F |
| 44 | H | Cl | CH | Ar1 | | | | F | | F | F |
| 45 | Me | Cl | CH | Ar1 | | | F | | | | |
| 46 | Me | Cl | CH | Ar1 | | F | F | | | F | F |
| 47 | Me | Cl | CH | Ar1 | | OMe | | | | F | F |
| 48 | Me | Cl | CH | Ar1 | | F | F | | | | |
| 49 | Me | Cl | CMe | Ar1 | | | | | | F | F |
| 50 | Me | Cl | CMe | Ar1 | | | F | | | F | F |
| 51 | H | Cl | CMe | Ar1 | | | F | | | F | F |
| 52 | H | Cl | CMe | Ar1 | | | | | | F | F |
| 53 | Me | Cl | CMe | Ar1 | | F | | | | F | F |
| 54 | H | Cl | CMe | Ar1 | | F | | | | F | F |
| 55 | Me | Cl | N | Ar1 | | | | | | Me | Me |
| 56 | Me | Cl | N | Ar1 | | | F | | | F | F |
| 57 | H | Cl | N | Ar1 | | | F | | | F | F |
| 58 | Me | Cl | N | Ar1 | | F | | | | F | F |
| 59 | H | Cl | N | Ar1 | | F | | | | F | F |
| 60 | Me | Cl | N | Ar1 | | | | | | F | F |
| 61 | H | Cl | N | Ar1 | | | | | | F | F |

TABLE 1-continued

| C. No. | $R^{1'}$ | $R^2$ | X | Ar | m | $R^5$ | $R^6$ | $R^{6'}$ | $R^{6''}$ | $R^7$ | $R^{7'}$ |
|---|---|---|---|---|---|---|---|---|---|---|---|
| 62 | Me | OMe | N | Ar1 | | | | | | F | F |
| 63 | H | OMe | N | Ar1 | | | | | | F | F |
| 64 | Me | OMe | N | Ar1 | | | F | | | F | F |
| 65 | Me | OMe | N | Ar1 | | F | | | | F | F |
| 66 | H | OMe | N | Ar1 | | F | | | | F | F |
| 67 | Me | OMe | N | Ar1 | | | | | | Me | Me |
| 68 | H | OMe | N | Ar1 | | | F | | | F | F |
| 69 | Me | OMe | N | Ar1 | | | F | | | | |
| 70 | Me | Cl | CCl | Ar2 | | | | | Cl | F | F |
| 71 | Me | Cl | CF | Ar2 | | | | | | | |
| 72 | H | Cl | CF | Ar2 | | | | | | | |
| 73 | Me | Cl | CF | Ar2 | | | | | | F | F |
| 74 | H | Cl | CF | Ar2 | | | | | | F | F |
| 75 | Me | Cl | CF | Ar2 | | | | | Cl | F | F |
| 76 | Me | Cl | CF | Ar2 | | | | | F | F | F |
| 77 | H | Cl | CF | Ar2 | | | | | F | F | F |
| 78 | Me | Cl | CF | Ar2 | | | | | Br | F | F |
| 79 | Me | Cl | CF | Ar2 | | | | | I | F | F |
| 80 | H | Cl | CF | Ar2 | | | | | Br | F | F |
| 81 | H | Cl | CF | Ar2 | | | | | I | F | F |
| 82 | H | Cl | CF | Ar2 | | | | | Cl | F | F |
| 83 | Me | Cl | CF | Ar2 | | | | | F | | |
| 84 | Me | Cl | CH | Ar2 | | | | | | F | F |
| 85 | H | Cl | CH | Ar2 | | | | | | F | F |
| 86 | Me | Cl | CH | Ar2 | | | | | Cl | F | F |
| 87 | H | Cl | CH | Ar2 | | | | | Cl | F | F |
| 88 | Me | Cl | CH | Ar2 | | | | | F | F | F |
| 89 | H | Cl | CH | Ar2 | | | | | F | F | F |
| 90 | Me | Cl | CH | Ar2 | | F | | | | F | F |
| 91 | H | Cl | CH | Ar2 | | F | | | | F | F |
| 92 | Me | Cl | CH | Ar2 | | | | | F | | |
| 93 | Me | Cl | CH | Ar2 | | | | | | | |
| 94 | Me | Cl | CMe | Ar2 | | | | | Cl | F | F |
| 95 | Me | OMe | N | Ar2 | | | | | Cl | F | F |
| 96 | H | OMe | N | Ar2 | | | | | Cl | F | F |
| 97 | Me | OMe | N | Ar2 | | | | | F | | |
| 98 | Me | OMe | N | Ar2 | | | | | | | |
| 99 | Me | OMe | N | Ar2 | | | | | | F | F |
| 100 | Me | Cl | CF | Ar3 | | | | | | | |
| 101 | H | Cl | CF | Ar3 | | | | | | | |
| 102 | Me | Cl | CF | Ar5 | | | | | | | |
| 103 | Me | Cl | CF | Ar7 | | | | | | | |
| 104 | H | Cl | CF | Ar7 | | | | | | | |
| 105 | Me | Cl | CF | Ar9 | 0 | | | | | | |
| 106 | Me | Cl | CH | Ar3 | | | | | | | |
| 107* | Me | Cl | CF | Ar16 | | | | | | | |
| 108** | H | Cl | CF | Ar16 | | | | | | | |

*For compound 107 $R^8$ and $R^{8'}$ are substituted and each is F.
**For compound 108 $R^{10}$ is substituted and is Me.

Methods of Preparing the Compounds

Exemplary procedures to synthesize the compounds of Formula (I) are provided below.

The 4-amino-6-(heterocyclic)picolinic acids of Formula (I) can be prepared in a number of ways. As depicted in Scheme I, the 4-amino-6-chloropicolinates of Formula (II) can be converted to the 4-amino-6-substituted-picolinates of Formula (III), wherein Ar is as herein defined, via Suzuki coupling with a boronic acid or ester, in the presence of a base, such as potassium fluoride, and a catalyst, such as bis(triphenylphosphine)-palladium(II)dichloride, in a polar, protic solvent mixture, such as acetonitrile-water, at a temperature, such as 110° C., e.g., in a microwave reactor (reaction $a_1$). 4-Amino-6-substituted-picolinates of Formula (III) can be transformed into the 5-iodo-4-amino-6-substituted-picolinates of Formula (IV) via a reaction with iodinating reagents, such as periodic acid and iodine, in a polar, protic solvent, such as methyl alcohol (reaction $b_1$). Stille coupling of the 5-iodo-4-amino-6-substituted-picolinates of Formula (IV) with a stannane, such as tetramethyltin, in the presence of a catalyst, such as bis(triphenylphosphine)-palladium(II) dichloride, in a non-reactive solvent, such as 1,2-dichloroethane, at a temperature, such as 120-130° C., e.g., in a microwave reactor, provides 5-(substituted)-4-amino-6-substituted-picolinates of Formula (I-A), wherein $Z_1$ is alkyl, alkenyl, alkynyl, haloalkenyl and alkylthio (reaction $c_1$).

Alternatively, 4-amino-6-chloropicolinates of Formula (II) can be transformed into the 5-iodo-4-amino-6-chloropicolinates of Formula (V) via a reaction with iodinating reagents, such as periodic acid and iodine, in a polar, protic solvent, such as methyl alcohol (reaction $b_2$). Stille coupling of the 5-iodo-4-amino-6-chloropicolinates of Formula (V) with a stannane, such as tetramethyltin, in the presence of a catalyst, such as bis(triphenylphosphine)-palladium(II)dichloride, in a non-reactive solvent, such as 1,2-dichloroethane, at a temperature, such as 120-130° C., e.g., in a microwave reactor, provides 5-(substituted)-4-amino-6-chloropicolinates of Formula (VI), wherein $Z_1$ is alkyl, alkenyl, alkynyl, haloalkenyl and alkylthio (reaction $c_2$). The 5-substituted-4-amino-6-chloropicolinates of Formula (VI) can be converted to the 5-substituted-4-amino-6-substituted-picolinates of Formula (I-A), wherein Ar is as herein defined, via Suzuki coupling with a boronic acid or ester, in the presence of a base, such as potassium fluoride, and a catalyst, such as bis(triphenylphosphine)-palladium(II)dichloride, in a polar, protic solvent mixture, such as acetonitrile-water, at a temperature, such as 110° C., e.g., in a microwave reactor (reaction $a_2$).

Scheme II

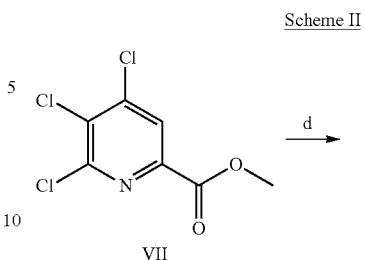

Scheme I

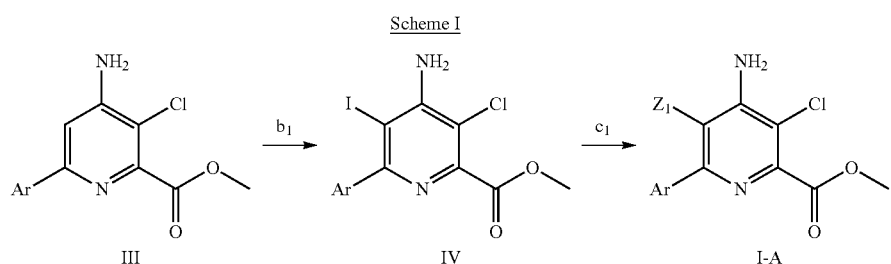

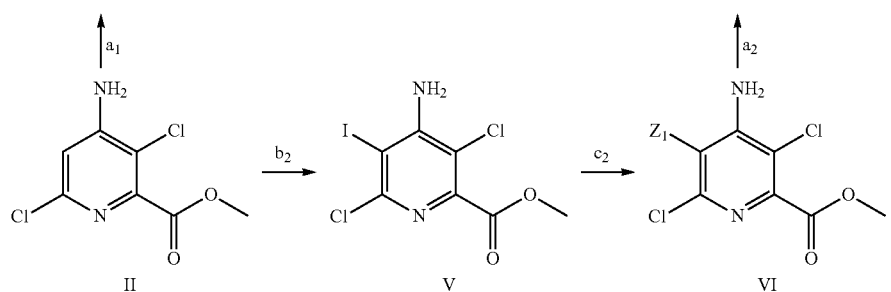

As depicted in Scheme II, the 4,5,6-trichloropicolinate of Formula (VII) can be converted to the corresponding isopropyl ester of Formula (VIII), via a reaction with isopropyl alcohol and concentrated sulfuric acid, e.g., at reflux temperature under Dean-Stark conditions (reaction d). The isopropyl ester of Formula (VIII) can be reacted with a fluoride ion source, such as cesium fluoride, in a polar, aprotic solvent, such as dimethyl sulfoxide (DMSO), at a temperature, such as 80° C., under Dean-Stark conditions, to yield the isopropyl 4,5,6-trifluoropicolinate of Formula (IX) (reaction e). The isopropyl 4,5,6-trifluoropicolinate of Formula (IX) can be aminated with a nitrogen source, such as ammonia, in a polar, aprotic solvent, such as DMSO, to produce a 4-amino-5,6-difluoropicolinate of Formula (X) (reaction f). The fluoro substituent in the 6-position of the 4-amino-5,6-difluoropicolinate of Formula (X) can be exchanged with a chloro substituent by treatment with a chloride source, such as hydrogen chloride, e.g., in dioxane, in a Parr reactor, at a temperature, such as 100° C., to produce a 4-amino-5-fluoro-6-chloro-picolinate of Formula (XI) (reaction g). The 4-amino-5-fluoro-6-chloropicolinate of Formula (XI) can be transesterified to the corresponding methyl ester of Formula (XII) by reaction with titanium(IV) isopropoxide in methyl alcohol at reflux temperature (reaction h).

-continued

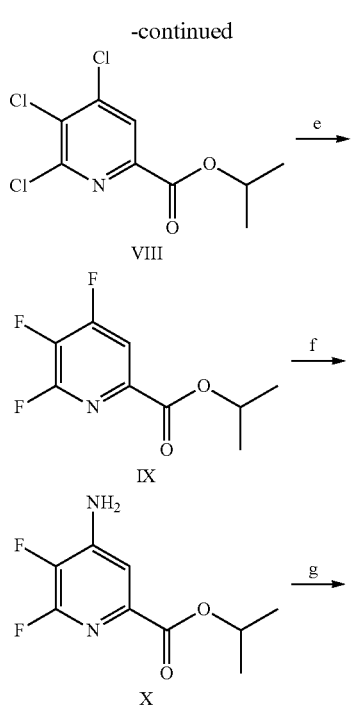

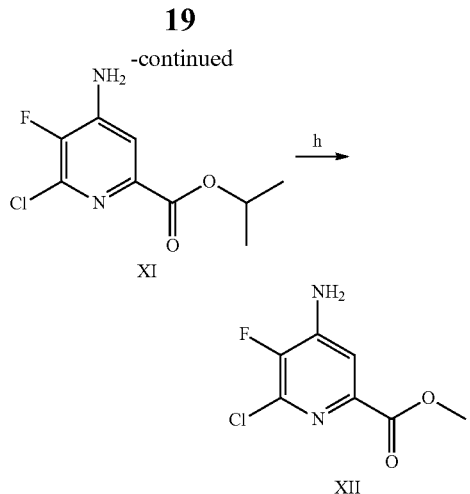

As depicted in Scheme III, the 4-amino-5-fluoro-6-chloropicolinate of Formula (XII) can be transformed into the 3-iodo-4-amino-5-fluoro-6-chloropicolinate of Formula (XIII) via reaction with iodinating reagents, such as periodic acid and iodine, in a polar, protic solvent, such as methyl alcohol (reaction $b_3$). Stille coupling of the 3-iodo-4-amino-5-fluoro-6-chloropicolinates of Formula (XIII) with a stannane, such as tributyl(vinyl)stannane, in the presence of a catalyst, such as bis(triphenylphosphine)-palladium(II)dichloride, in a non-reactive solvent, such as 1,2-dichloroethane, at a temperature, such as 120-130° C., e.g., in a microwave reactor, provides 3-(substituted)-4-amino-5-fluoro-6-chloropicolinates of Formula (XIV), wherein $R^2$ is alkyl, alkenyl, alkynyl, haloalkenyl and alkylthio (reaction $c_3$). Alternatively, the 3-iodo-4-amino-5-fluoro-6-chloropicolinates of Formula (XIII) can be treated with cesium carbonate and a catalytic amount of both copper(I) iodide and 1,10-phenanthroline in the presence of a polar, protic solvent, such as methyl alcohol, at a temperature, such as 65° C., to provide a 3-(substituted)-4-amino-5-fluoro-6-chloropicolinic acids of Formula (XIV), wherein $R^2$ is alkoxy or haloalkoxy (reaction $i_1$), which can be esterified to the methyl esters, e.g., by treatment with hydrogen chloride (gas) and methyl alcohol at 50° C. (reaction $j_1$). The 3-(substituted)-4-amino-5-fluoro-6-chloropicolinates of Formula (XIV) can be converted to the 4-amino-6-substituted-picolinates of Formula (I-B), wherein Ar is as herein defined, via Suzuki coupling with a boronic acid or ester, in the presence of a base, such as potassium fluoride, and a catalyst, such as bis(triphenylphosphine)-palladium(II)dichloride, in a polar, protic solvent mixture, such as acetonitrile-water, at a temperature, such as 110° C., e.g., in a microwave reactor (reaction $a_3$).

Alternatively, the 4-amino-5-fluoro-6-chloropicolinates of Formula (XII) can be converted to the 4-amino-5-fluoro-6-substituted-picolinates of Formula (XV), wherein Ar is as herein defined, via Suzuki coupling with a boronic acid or ester, in the presence of a base, such as potassium fluoride, and a catalyst, such as bis(triphenylphosphine)-palladium(II) dichloride, in a polar, protic solvent mixture, such as acetonitrile-water, at a temperature, such as 110° C., e.g., in a microwave reactor (reaction $a_4$). The 4-amino-5-fluoro-6-substituted-picolinates of Formula (XV) can be transformed into the 3-iodo-4-amino-5-fluoro-6-substituted-picolinates of Formula (XVI) via reaction with iodinating reagents, such as periodic acid and iodine, in a polar, protic solvent, such as methyl alcohol (reaction $b_4$). Stille coupling of the 3-iodo-4-amino-5-fluoro-6-substituted-picolinates of Formula (XVI) with a stannane, such as tributyl(vinyl)stannane, in the presence of a catalyst, such as bis(triphenylphosphine)-palladium(II)dichloride, in a non-reactive solvent, such as 1,2-dichloroethane, at a temperature, such as 120-130° C., e.g., in a microwave reactor, provides 3-(substituted)-4-amino-5-fluoro-6-substituted-picolinates of Formula (I-B), wherein $R^2$ is alkyl, alkenyl, alkynyl, haloalkenyl and alkylthio (reaction $c_4$). Alternatively, the 3-iodo-4-amino-5-fluoro-6-substituted-picolinates of Formula (XVI) can be treated with cesium carbonate and a catalytic amount of both copper(I) iodide and 1,10-phenanthroline in the presence of a polar, protic solvent, such as methyl alcohol, at a temperature, such as 65° C., to provide a 3-(substituted)-4-amino-5-fluoro-6-substituted-picolinic acids of Formula (I-B), wherein $R^2$ is alkoxy or haloalkoxy (reaction $i_2$), which can be esterified to the methyl esters, e.g., by treatment with hydrogen chloride (gas) and methyl alcohol, at a temperature, such as 50° C. (reaction $j_2$).

Scheme III

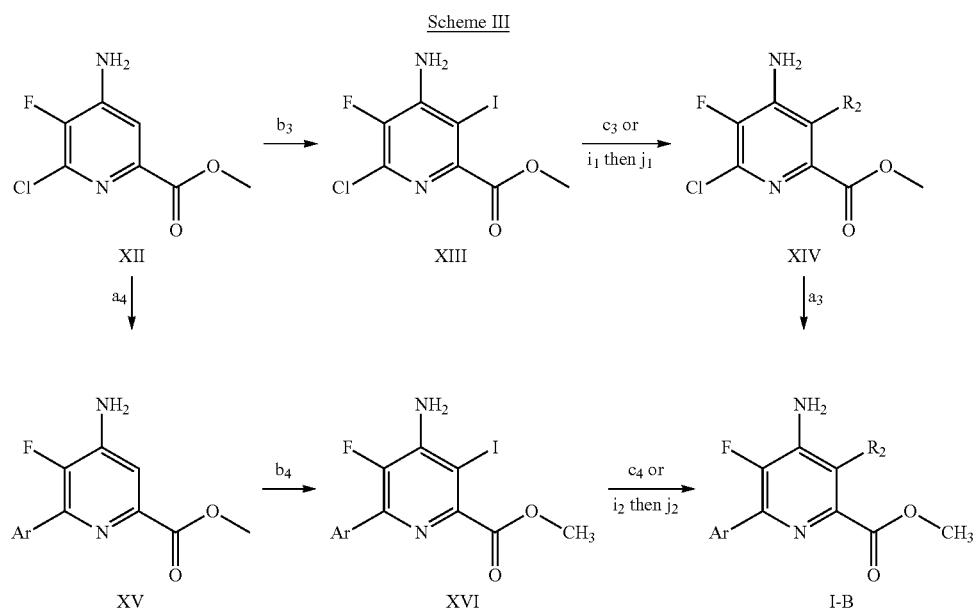

As depicted in Scheme IV, the 4-acetamido-6-(trimethylstannyl)picolinates of Formula (XVII) can be converted to the 4-acetamido-6-substituted-picolinates of Formula (XVIII), wherein Ar is as herein defined, via Stille coupling with an aryl bromide or aryl iodide, in the presence of a catalyst, such as bis(triphenylphosphine)-palladium(II)dichloride, in a solvent, such as 1,2-dichloroethane, e.g., at reflux temperature (reaction k). 4-Amino-6-substituted-picolinates of Formula (I-C), wherein Ar is as herein defined, can be synthesized from 4-acetamido-6-substituted-picolinates of Formula (XVIII) via standard deprotecting methods, such as hydrochloric acid gas in methanol (reaction l).

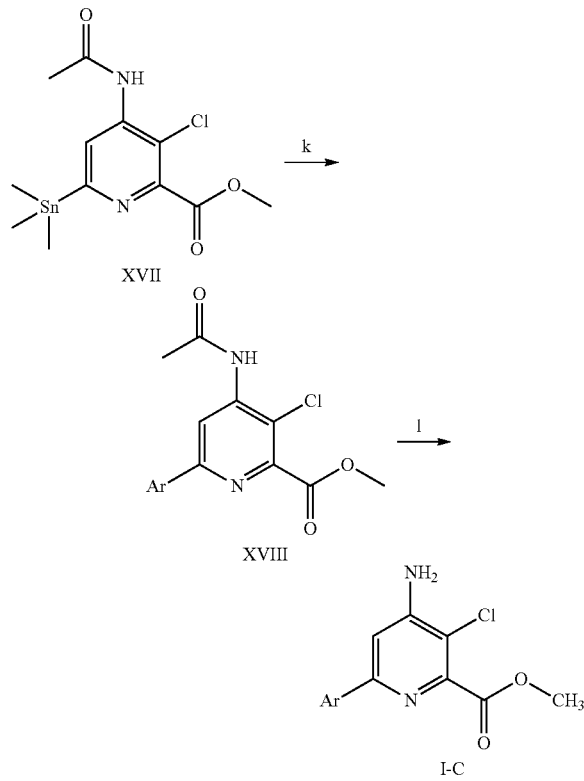

As depicted in Scheme V, 2,4-dichloro-5-methoxypyrimidine (XIX) can be transformed into 2,4-dichloro-5-methoxy-6-vinylpyrimidine (XX) via a reaction with vinyl magnesium bromide, in a polar, aprotic solvent, such as tetrahydrofuran (reaction m). 2,4-Dichloro-5-methoxy-6-vinylpyrimidine (XX) can be transformed into 2,6-dichloro-5-methoxypyrimidine-4-carboxaldehyde (XXI) via treatment with ozone, e.g., in a dichloromethane:methanol solvent mixture (reaction n). 2,6-Dichloro-5-methoxypyrimidine-4-carboxaldehyde (XXI) can be transformed into methyl 2,6-dichloro-5-methoxypyrimidine-4-carboxylate (XXII) via treatment with bromine, e.g., in a methanol:water solvent mixture (reaction o). Methyl 2,6-dichloro-5-methoxypyrimidine-4-carboxylate (XXII) can be transformed into methyl 6-amino-2-chloro-5-methoxypyrimidine-4-carboxylate (XXIII) via treatment with ammonia (e.g., 2 equivalents) in a solvent, such as DMSO (reaction p). Finally, 6-amino-2-substituted-5-methoxypyrimidine-4-carboxylates of Formula (I-D), wherein Ar is as herein defined, can be prepared via Suzuki coupling with a boronic acid or ester, with 6-amino-2-chloro-5-methoxypyrimidine-4-carboxylate (XXIII), in the presence of a base, such as potassium fluoride, and a catalyst, such as bis(triphenylphosphine)-palladium(II)dichloride, in a polar, protic solvent mixture, such as acetonitrile-water, at a temperature, such as 110° C., e.g., in a microwave reactor (reaction $a_5$).

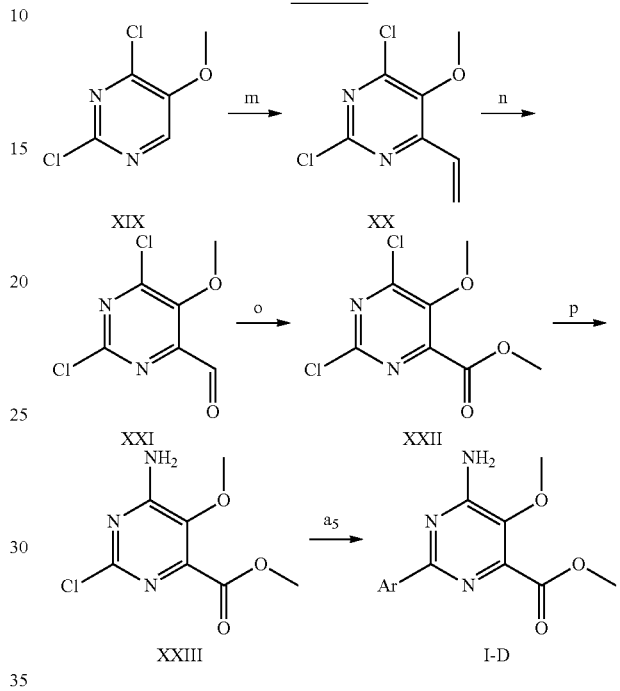

The compounds of Formulae I-A, I-B, I-C, and I-D obtained by any of these processes, can be recovered by conventional means and purified by standard procedures, such as by recrystallization or chromatography. The compounds of Formula (I) can be prepared from compounds of Formulae I-A, I-B, I-C, and I-D using standard methods well known in the art.

Compositions and Methods

In some embodiments, the compounds provided herein are employed in mixtures containing a herbicidally effective amount of the compound along with at least one agriculturally acceptable adjuvant or carrier. Exemplary adjuvants or carriers include those that are not phytotoxic or significantly phytotoxic to valuable crops, e.g., at the concentrations employed in applying the compositions for selective weed control in the presence of crops, and/or do not react or significantly react chemically with the compounds provided herein or other composition ingredients. Such mixtures can be designed for application directly to weeds or their locus or can be concentrates or formulations that are diluted with additional carriers and adjuvants before application. They can be solids, such as, for example, dusts, granules, water dispersible granules, or wettable powders, or liquids, such as, emulsifiable concentrates, solutions, emulsions or suspensions. They can also be provided as a pre-mix or tank-mixed.

Suitable agricultural adjuvants and carriers that are useful in preparing the herbicidal mixtures of the disclosure are well known to those skilled in the art. Some of these adjuvants include, but are not limited to, crop oil concentrate (mineral oil (85%)+emulsifiers (15%)); nonylphenol ethoxylate; benzylcocoalkyldimethyl quaternary ammonium salt; blend of petroleum hydrocarbon, alkyl esters, organic acid, and anionic surfactant; $C_9$-$C_{11}$ alkylpolyglycoside; phosphated alcohol ethoxylate; natural primary alcohol ($C_{12}$-$C_{16}$) ethoxylate; di-sec-butylphenol EO-PO block copolymer; polysiloxane-methyl cap; nonylphenol ethoxylate+urea ammonium nitrate; emulsified methylated seed oil; tridecyl alcohol (synthetic) ethoxylate (8EO); tallow amine ethoxylate (15 EO); PEG(400) dioleate-99.

Liquid carriers that can be employed include water and organic solvents. The organic solvents typically used include, but are not limited to, petroleum fractions or hydrocarbons such as mineral oil, aromatic solvents, paraffinic oils, and the like; vegetable oils such as soybean oil, rapeseed oil, olive oil, castor oil, sunflower seed oil, coconut oil, corn oil, cottonseed oil, linseed oil, palm oil, peanut oil, safflower oil, sesame oil, tung oil and the like; esters of the above vegetable oils; esters of monoalcohols or dihydric, trihydric, or other lower polyalcohols (4-6 hydroxy containing), such as 2-ethylhexyl stearate, n-butyl oleate, isopropyl myristate, propylene glycol dioleate, di-octyl succinate, di-butyl adipate, di-octyl phthalate and the like; esters of mono-, di- and poly-carboxylic acids and the like. Specific organic solvents include toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, methyl alcohol, ethyl alcohol, isopropyl alcohol, amyl alcohol, ethylene glycol, propylene glycol, glycerine, N-methyl-2-pyrrolidinone, N,N-dimethyl alkylamides, dimethyl sulfoxide, liquid fertilizers, and the like. In some embodiments, water is the carrier for the dilution of concentrates.

Suitable solid carriers include talc, pyrophyllite clay, silica, attapulgus clay, kaolin clay, kieselguhr, chalk, diatomaceous earth, lime, calcium carbonate, bentonite clay, Fuller's earth, cottonseed hulls, wheat flour, soybean flour, pumice, wood flour, walnut shell flour, lignin, and the like.

In some embodiments, one or more surface-active agents are utilized in the compositions of the present disclosure. Such surface-active agents are, in some embodiments, employed in both solid and liquid compositions, e.g., those designed to be diluted with carrier before application. The surface-active agents can be anionic, cationic or nonionic in character and can be employed as emulsifying agents, wetting agents, suspending agents, or for other purposes. Surfactants conventionally used in the art of formulation and which may also be used in the present formulations are described, inter alia, in *McCutcheon's Detergents and Emulsifiers Annual*, MC Publishing Corp., Ridgewood, N.J., 1998, and in *Encyclopedia of Surfactants*, Vol. I-III, Chemical Publishing Co., New York, 1980-81. Typical surface-active agents include salts of alkyl sulfates, such as diethanolammonium lauryl sulfate; alkylarylsulfonate salts, such as calcium dodecylbenzenesulfonate; alkylphenol-alkylene oxide addition products, such as nonylphenol-$C_{18}$ ethoxylate; alcohol-alkylene oxide addition products, such as tridecyl alcohol-$C_{16}$ ethoxylate; soaps, such as sodium stearate; alkylnaphthalene-sulfonate salts, such as sodium dibutylnaphthalenesulfonate; dialkyl esters of sulfosuccinate salts, such as sodium di(2-ethylhexyl) sulfosuccinate; sorbitol esters, such as sorbitol oleate; quaternary amines, such as lauryl trimethylammonium chloride; polyethylene glycol esters of fatty acids, such as polyethylene glycol stearate; block copolymers of ethylene oxide and propylene oxide; salts of mono- and dialkyl phosphate esters; vegetable or seed oils such as soybean oil, rapeseed/canola oil, olive oil, castor oil, sunflower seed oil, coconut oil, corn oil, cottonseed oil, linseed oil, palm oil, peanut oil, safflower oil, sesame oil, tung oil and the like; and esters of the above vegetable oils, e.g., methyl esters.

Oftentimes, some of these materials, such as vegetable or seed oils and their esters, can be used interchangeably as an agricultural adjuvant, as a liquid carrier or as a surface active agent.

Other adjuvants commonly used in agricultural compositions include compatibilizing agents, antifoam agents, sequestering agents, neutralizing agents and buffers, corrosion inhibitors, dyes, odorants, spreading agents, penetration aids, sticking agents, dispersing agents, thickening agents, freezing point depressants, antimicrobial agents, and the like. The compositions may also contain other compatible components, for example, other herbicides, plant growth regulants, fungicides, insecticides, and the like and can be formulated with liquid fertilizers or solid, particulate fertilizer carriers such as ammonium nitrate, urea and the like.

The concentration of the active ingredients in the herbicidal compositions of this disclosure is generally from about 0.001 to about 98 percent by weight. Concentrations from about 0.01 to about 90 percent by weight are often employed. In compositions designed to be employed as concentrates, the active ingredient is generally present in a concentration from about 5 to about 98 weight percent, preferably about 10 to about 90 weight percent. Such compositions are typically diluted with an inert carrier, such as water, before application. The diluted compositions usually applied to weeds or the locus of weeds generally contain about 0.0001 to about 1 weight percent active ingredient and preferably contain about 0.001 to about 0.05 weight percent.

The present compositions can be applied to weeds or their locus by the use of conventional ground or aerial dusters, sprayers, and granule applicators, by addition to irrigation or flood water, and by other conventional means known to those skilled in the art.

In some embodiments, the compounds and compositions described herein are applied as a post-emergence application, pre-emergence application, in-water application to flooded paddy rice or water bodies (e.g., ponds, lakes and streams), or burn-down application.

In some embodiments, the compounds and compositions provided herein are utilized to control weeds in crops, including but not limited to citrus, apple, rubber, oil, palm, forestry, direct-seeded, water-seeded and transplanted rice, wheat, barley, oats, rye, sorghum, corn/maize, pastures, grasslands, rangelands, fallowland, turf, tree and vine orchards, aquatics, or row-crops, as well as non-crop settings, e.g., industrial vegetation management (IVM) or rights-of-way. In some embodiments, the compounds and compositions are used to control woody plants, broadleaf and grass weeds, or sedges.

In some embodiments, the compounds and compositions provided herein are utilized to control undesirable vegetation in rice. In certain embodiments, the undesirable vegetation is *Brachiaria platyphylla* (Groseb.) Nash (broadleaf signalgrass, BRAPP), *Digitaria sanguinalis* (L.) Scop. (large crabgrass, DIGSA), *Echinochloa crus-galli* (L.) P. Beauv. (barnyardgrass, ECHCG), *Echinochloa colonum* (L.) LINK (junglerice, ECHCO), *Echinochloa oryzoides* (Ard.) Fritsch (early watergrass, ECHOR), *Echinochloa oryzicola* (Vasinger) Vasinger (late watergrass, ECHPH), *Ischaemum rugosum* Salisb. (saramollagrass, ISCRU), *Leptochloa chinensis* (L.) Nees (Chinese sprangletop, LEFCH), *Leptochloa fascicularis* (Lam.) Gray (bearded sprangletop, LEFFA), *Leptochloa panicoides* (Pres1.) Hitchc. (Amazon sprangletop, LEFPA), *Panicum dichotomiflorum* (L.) Michx. (fall panicum, PANDI), *Paspalum dilatatum* Poir. (dallisgrass, PASDI), *Cyperus difformis* L. (smallflower flatsedge, CYPDI), *Cyperus esculentus* L. (yellow nutsedge, CYPES), *Cyperus iria* L. (rice flatsedge, CYPIR), *Cyperus rotundus* L. (purple nutsedge, CYPRO), *Eleocharis* species (ELOSS), *Fimbristylis miliacea* (L.) Vahl (globe fringerush, FIMMI), *Schoenoplectus juncoides* Roxb. (Japanese bulrush, SCPJU), *Schoenoplectus maritimus* L. (sea clubrush, SCPMA), *Schoenoplectus mucronatus* L. (ricefield bulrush, SCPMU), *Aeschynomene* species, (jointvetch, AESSS), *Alternanthera philoxeroides* (Mart.) Griseb. (alligatorweed, ALRPH), *Alisma plantago-aquatica* L. (common waterplantain, ALSPA), *Amaranthus* species, (pigweeds and amaranths, AMASS), *Ammannia coccinea* Rottb. (redstem, AMMCO), *Eclipta alba* (L.) Hassk. (American false daisy, ECLAL), *Heteranthera limosa* (SW.) Willd./Vahl (ducksalad, HETLI), *Heteranthera reniformis* R. & P. (roundleaf mudplantain, HETRE), *Ipomoea hederacea* (L.) Jacq. (ivyleaf morningglory, IPOHE), *Lindernia dubia* (L.) Pennell (low false pimpernel, LIDDU), *Monochoria korsakowii* Regel & Maack (monochoria, MOOKA), *Monochoria vaginalis* (Burm. F.) C. Presl ex Kuhth (monochoria, MOOVA), *Murdannia nudiflora* (L.) Brenan (doveweed, MUDNU), *Polygonum pensylvanicum* L. (Pennsylvania smartweed, POLPY), *Polygonum persicaria* L. (ladysthumb, POLPE), *Polygonum hydropiperoides* Michx. (mild smartweed, POLHP), *Rotala indica* (Willd.) Koehne (Indian toothcup, ROTIN), *Sagittaria* species, (arrowhead, SAGSS), *Sesbania exaltata* (Raf.) Cory/Rydb. Ex Hill (hemp sesbania, SEBEX), or *Sphenoclea zeylanica* Gaertn. (gooseweed, SPDZE).

In some embodiments, the compounds and compositions provided herein are utilized to control undesirable vegetation in cereals. In certain embodiments, the undesirable vegetation is *Alopecurus myosuroides* Huds. (blackgrass, ALOMY), *Apera spica-venti* (L.) Beauv. (windgrass, APESV), *Avena fatua* L. (wild oat, AVEFA), *Bromus tectorum* L. (downy brome, BROTE), *Lolium multiflorum* Lam. (Italian ryegrass, LOLMU), *Phalaris minor* Retz. (littleseed canarygrass, PHAMI), *Poa annua* L. (annual bluegrass, POAAN), *Setaria pumila* (Poir.) Roemer & J. A. Schultes (yellow foxtail, SETLU), *Setaria viridis* (L.) Beauv. (green foxtail, SETVI), *Cirsium arvense* (L.) Scop. (Canada thistle, CIRAR), *Galium aparine* L. (catchweed bedstraw, GALAP), *Kochia scoparia* (L.) Schrad. (kochia, KCHSC), *Lamium purpureum* L. (purple deadnettle, LAMPU), *Matricaria recutita* L. (wild chamomile, MATCH), *Matricaria matricarioides* (Less.) Porter (pineappleweed, MATMT), *Papaver rhoeas* L. (common poppy, PAPRH), *Polygonum convolvulus* L. (wild buckwheat, POLCO), *Salsola tragus* L. (Russian thistle, SASKR), *Stellaria media* (L.) Vill. (common chickweed, STEME), *Veronica persica* Poir. (Persian speedwell, VERPE), *Viola arvensis* Murr. (field violet, VIOAR), or *Viola tricolor* L. (wild violet, VIOTR).

In some embodiments, the compounds and compostions provided herein are utilized to control undesirable vegetation in range and pasture. In certain embodiments, the undesirable vegetation is *Ambrosia artemisiifolia* L. (common ragweed, AMBEL), *Cassia obtusifolia* (sickle pod, CASOB), *Centaurea maculosa* auct. non Lam. (spotted knapweed, CENMA), *Cirsium arvense* (L.) Scop. (Canada thistle, CIRAR), *Convolvulus arvensis* L. (field bindweed, CONAR), *Euphorbia esula* L. (leafy spurge, EPHES), *Lactuca serriola* L./Torn. (prickly lettuce, LACSE), *Plantago lanceolata* L. (buckhorn plantain, PLALA), *Rumex obtusifolius* L. (broadleaf dock, RUMOB), *Sida spinosa* L. (prickly sida, SIDSP), *Sinapis arvensis* L. (wild mustard, SINAR), *Sonchus arvensis* L. (perennial sowthistle, SONAR), *Solidago* species (goldenrod, SOOSS), *Taraxacum officinale* G. H. Weber ex Wiggers (dandelion, TAROF), *Trifolium repens* L. (white clover, TRFRE), or *Urtica dioica* L. (common nettle, URTDI).

In some embodiments, the compounds and compositions provided herein are utilized to control undesirable vegetation found in row crops. In certain embodiments, the undesirable vegetation is *Alopecurus myosuroides* Huds. (blackgrass, ALOMY), *Avena fatua* L. (wild oat, AVEFA), *Brachiaria platyphylla* (Groseb.) Nash (broadleaf signalgrass, BRAPP), *Digitaria sanguinalis* (L.) Scop. (large crabgrass, DIGSA), *Echinochloa crus-galli* (L.) P. Beauv. (barnyardgrass, ECHCG), *Echinochloa colonum* (L.) Link (junglerice, ECHCO), *Lolium multiflorum* Lam. (Italian ryegrass, LOLMU), *Panicum dichotomiflorum* Michx. (fall *panicum*, PANDI), *Panicum miliaceum* L. (wild-proso millet, PANMI), *Setaria faberi* Herrm. (giant foxtail, SETFA), *Setaria viridis* (L.) Beauv. (green foxtail, SETVI), *Sorghum halepense* (L.) Pers. (Johnsongrass, SORHA), *Sorghum bicolor* (L.) *Moench* ssp. *Arundinaceum* (shattercane, SORVU), *Cyperus esculentus* L. (yellow nutsedge, CYPES), *Cyperus rotundus* L. (purple nutsedge, CYPRO), *Abutilon theophrasti* Medik. (velvetleaf, ABUTH), *Amaranthus* species (pigweeds and amaranths, AMASS), *Ambrosia artemisiifolia* L. (common ragweed, AMBEL), *Ambrosia psilostachya* DC. (western ragweed, AMBPS), *Ambrosia trifida* L. (giant ragweed, AMBTR), *Asclepias syriaca* L. (common milkweed, ASCSY), *Chenopodium album* L. (common lambsquarters, CHEAL), *Cirsium arvense* (L.) Scop. (Canada thistle, CIRAR), *Commelina benghalensis* L. (tropical spiderwort, COMBE), *Datura stramonium* L. (jimsonweed, DATST), *Daucus carota* L. (wild carrot, DAUCA), *Euphorbia heterophylla* L. (wild poinsettia, EPHHL), *Erigeron bonariensis* L. (hairy fleabane, ERIBO), *Erigeron canadensis* L. (Canadian fleabane, ERICA), *Helianthus annuus* L. (common sunflower, HELAN), *Jacquemontia tamnifolia* (L.) Griseb. (smallflower morningglory, IAQTA), *Ipomoea hederacea* (L.) Jacq. (ivyleaf morningglory, IPOHE), *Ipomoea lacunosa* L. (white morningglory, IPOLA), *Lactuca serriola* L./Torn. (prickly lettuce, LACSE), *Portulaca oleracea* L. (common purslane, POROL), *Sida spinosa* L. (prickly *sida*, SIDSP), *Sinapis arvensis* L. (wild mustard, SINAR), *Solanum ptychanthum* Dunal (eastern black nightshade, SOLPT), or *Xanthium strumarium* L. (common cocklebur, XANST).

In some embodiments, application rates of about 1 to about 4,000 grams/hectare (g/ha) are employed in post-emergence operations. In some embodiments, rates of about 1 to about 4,000 g/ha are employed in pre-emergence operations.

In some embodiments, the compounds, compositions, and methods provided herein are used in conjunction with one or more other herbicides to control a wider variety of undesirable vegetation. When used in conjunction with other herbicides, the presently claimed compounds can be formulated with the other herbicide or herbicides, tank-mixed with the other herbicide or herbicides or applied sequentially with the other herbicide or herbicides. Some of the herbicides that can be employed in conjunction with the compounds of the present disclosure include: 4-CPA, 4-CPB, 4-CPP, 2,4-D, 2,4-D choline salt, 2,4-D esters and amines, 2,4-DB, 3,4-DA, 3,4-DB, 2,4-DEB, 2,4-DEP, 3,4-DP, 2,3,6-TBA, 2,4,5-T, 2,4,5-TB, acetochlor, acifluorfen, aclonifen, acrolein, alachlor, allidochlor, alloxydim, allyl alcohol, alorac, ametridione, ametryn, amibuzin, amicarbazone, amidosulfuron, aminocyclopyrachlor, aminopyralid, amiprofos-methyl, amitrole, ammonium sulfamate, anilofos, anisuron, asulam, atraton, atrazine, azafenidin, azimsulfuron, aziprotryne, barban, BCPC, beflubutamid, benazolin, bencarbazone, benfluralin, benfuresate, bensulfuron-methyl, bensulide, benthiocarb, bentazon-sodium, benzadox, benzfendizone, benzipram, benzobicyclon, benzofenap, benzofluor, benzoylprop, benzthiazuron, bicyclopyrone, bifenox, bilanafos, bispyribac-sodium, borax, bromacil, bromobonil, bromobutide, bromofenoxim, bromoxynil, brompyrazon, butachlor, butafenacil, butamifos, butenachlor, buthidazole, buthiuron, butralin, butroxydim, buturon, butylate, cacodylic acid, cafenstrole, calcium chlorate, calcium cyanamide, cambendichlor, carbasulam, carbetamide, carboxazole, chlorprocarb, carfentrazone-ethyl, CDEA, CEPC, chlomethoxyfen, chloramben, chloranocryl, chlorazifop, chlorazine, chlorbromuron, chlorbufam, chloreturon, chlorfenac, chlorfenprop, chlorflurazole, chlorflurenol, chloridazon, chlorimuron, chlornitrofen, chloropon, chlorotoluron, chloroxuron, chloroxynil, chlorpropham, chlorsulfuron, chlorthal, chlorthiamid, cinidon-ethyl, cinmethylin, cinosulfuron, cisanilide, clethodim, cliodinate, clodinafop-propargyl, clofop, clomazone, clomeprop, cloprop, cloproxydim, clopyralid, cloransulam-methyl, CMA, copper sulfate, CPMF, CPPC, credazine, cresol, cumyluron, cyanatryn, cyanazine, cycloate, cyclosulfamuron, cycloxydim, cycluron, cyhalofop-butyl, cyperquat, cyprazine, cyprazole, cypromid, daimuron, dalapon, dazomet, delachlor, desmedipham, desmetryn, di-allate, dicamba, dichlobenil, dichloralurea, dichlormate, dichlorprop, dichlorprop-P, diclofop, diclosulam, diethamquat, diethatyl, difenopenten, difenoxuron, difenzoquat, diflufenican, diflufenzopyr, dimefuron, dimepiperate, dimethachlor, dimethametryn, dimethenamid, dimethenamid-P, dimexano, dimidazon, dinitramine, dinofenate, dinoprop, dinosam, dinoseb, dinoterb, diphenamid, dipropetryn, diquat, disul, dithiopyr, diuron, DMPA, DNOC, DSMA, EBEP, eglinazine, endothal, epronaz, EPTC, erbon, esprocarb, ethalfluralin, ethbenzamide, ethametsulfuron, ethidimuron, ethiolate, ethobenzamid, etobenzamid, ethofumesate, ethoxyfen, ethoxysulfuron, etinofen, etnipromid, etobenzanid, EXD, fenasulam, fenoprop, fenoxaprop, fenoxaprop-P-ethyl, fenoxaprop-P-ethyl+isoxadifen-ethyl, fenoxasulfone, fenteracol, fenthiaprop, fentrazamide, fenuron, ferrous sulfate, flamprop, flamprop-M, flazasulfuron, florasulam, fluazifop, fluazifop-P-butyl, fluazolate, flucarbazone, flucetosulfuron, fluchloralin, flufenacet, flufenican, flufenpyr-ethyl, flumetsulam, flumezin, flumiclorac-pentyl, flumioxazin, flumipropyn, fluometuron, fluorodifen, fluoroglycofen, fluoromidine, fluoronitrofen, fluothiuron, flupoxam, flupropacil, flupropanate, flupyrsulfuron, fluridone, fluorochloridone, fluoroxypyr, flurtamone, fluthiacet, fomesafen, foramsulfuron, fosamine, furyloxyfen, glufosinate, glufosinate-ammonium, glyphosate, halosafen, halosulfuron-methyl, haloxydine, haloxyfop-methyl, haloxyfop-P-methyl, halauxifen-methyl, hexachloroacetone, hexaflurate, hexazinone, imazamethabenz, imazamox, imazapic, imazapyr, imazaquin, imazethapyr, imazosulfuron, indanofan, indaziflam, iodobonil, iodomethane, iodosulfuron, iofensulfuron, ioxynil, ipazine, ipfencarbazone, iprymidam, isocarbamid, isocil, isomethiozin, isononuron, isopolinate, isopropalin, isoproturon, isouron, isoxaben, isoxachlortole, isoxaflutole, isoxapyrifop, karbutilate, ketospiradox, lactofen, lenacil, linuron, MAA, MAMA, MCPA, esters and amines, MCPA-thioethyl, MCPB, mecoprop, mecoprop-P, medinoterb, mefenacet, mefluidide, mesoprazine, mesosulfuron, mesotrione, metam, metamifop, metamitron, metazachlor, metazosulfuron, metflurazon, methabenzthiazuron, methalpropalin, methazole, methiobencarb, methiozolin, methiuron, methometon, methoprotryne, methyl bromide, methyl isothiocyanate, methyldymron, metobenzuron, metobromuron, metolachlor, metosulam, metoxuron, metribuzin, metsulfuron, molinate, monalide, monisouron, monochloroacetic acid, monolinuron, monuron, morfamquat, MSMA, naproanilide, napropamide, napropamide-M, naptalam, neburon, nicosulfuron, nipyraclofen, nitralin, nitrofen, nitrofluorfen, norflurazon, noruron, OCH, orbencarb, orthodichlorobenzene, orthosulfamuron, oryzalin, oxadiargyl, oxadiazon, oxapyrazon, oxasulfuron, oxaziclomefone, oxyfluorfen, paraflufen-ethyl, parafluoron, paraquat, pebulate, pelargonic acid, pendimethalin, penoxsulam, pentachlorophenol, pentanochlor, pentoxazone, perfluidone, pethoxamid, phenisopham, phenmedipham, phenmedipham-ethyl, phenobenzuron, phenylmercury acetate, picloram, picolinafen, pinoxaden, piperophos, potassium arsenite, potassium azide, potassium cyanate, pretilachlor, primisulfuron-methyl, procyazine, prodiamine, profluazol, profluralin, profoxydim, proglinazine, prohexadione-calcium, prometon, prometryn, propachlor, propanil, propaquizafop, propazine, propham, propisochlor, propoxycarbazone, propyrisulfuron, propyzamide, prosulfalin, prosulfocarb, prosulfuron, proxan, prynachlor, pydanon, pyraclonil, pyraflufen, pyrasulfotole, pyrazogyl, pyrazolynate, pyrazosulfuron-ethyl, pyrazoxyfen, pyribenzoxim, pyributicarb, pyriclor, pyridafol, pyridate, pyriftalid, pyriminobac, pyrimisulfan, pyrithiobac-methyl, pyroxasulfone, pyroxsulam, quinclorac, quinmerac, quinoclamine, quinonamid, quizalofop, quizalofop-P-ethyl, rhodethanil, rimsulfuron, saflufenacil, S-metolachlor, sebuthylazine, secbumeton, sethoxydim, siduron, simazine, simeton, simetryn, SMA, sodium arsenite, sodium azide, sodium chlorate, sulcotrione, sulfallate, sulfentrazone, sulfometuron, sulfosate, sulfosulfuron, sulfuric acid, sulglycapin, swep, TCA, tebutam, tebuthiuron, tefuryltrione, tembotrione, tepraloxydim, terbacil, terbucarb, terbuchlor, terbumeton, terbuthylazine, terbutryn, tetrafluoron, thenylchlor, thiazafluoron, thiazopyr, thidiazimin, thidiazuron, thiencarbazone-methyl, thifensulfuron, thiobencarb, tiocarbazil, tioclorim, topramezone, tralkoxydim, triafamone, tri-allate, triasulfuron, triaziflam, tribenuron, tricamba, triclopyr esters and amines, tridiphane, trietazine, trifloxysulfuron, trifluralin, triflusulfuron, trifop, trifopsime, trihydroxytriazine, trimeturon, tripropindan, tritac, tritosulfuron, vernolate and xylachlor.

The compounds and compositions of the present disclosure can generally be employed in combination with known herbicide safeners, such as benoxacor, benthiocarb, brassinolide, cloquintocet (e.g., mexyl), cyometrinil, daimuron, dichlormid, dicyclonon, dimepiperate, disulfoton, fenchlorazole-ethyl, fenclorim, flurazole, fluxofenim, furilazole, harpin proteins, isoxadifen-ethyl, mefenpyr-diethyl, MG 191, MON 4660, naphthalic anhydride (NA), oxabetrinil, 829148 and N-phenylsulfonylbenzoic acid amides, to enhance their selectivity.

The compounds, compositions, and methods described herein be used to control undesirable vegetation on glyphosate-tolerant-, glufosinate-tolerant-, dicamba-tolerant-, phenoxy auxin-tolerant-, pyridyloxy auxin-tolerant-, aryloxyphenoxypropionate-tolerant-, acetyl CoA carboxylase (ACCase) inhibitor-tolerant-, imidazolinone-tolerant-, acetolactate synthase (ALS) inhibitor-tolerant-, 4-hydroxyphenylpyruvate dioxygenase (HPPD) inhibitor-tolerant-, protoporphyrinogen oxidase (PPO) inhibitor-tolerant-, triazine-tolerant-, and bromoxynil-tolerant-crops (such as, but not limited to, soybean, cotton, canola/oilseed rape, rice, cereals, corn, turf, etc), for example, in conjunction with glyphosate, glufosinate, dicamba, phenoxy auxins, pyridyloxy auxins, aryloxyphenoxypropionates, ACCase inhibitors, imidazolinones, ALS inhibitors, HPPD inhibitors, PPO inhibitors, triazines, and bromoxynil. The compositions and methods may be used in controlling undesirable vegetation in crops possessing multiple or stacked traits conferring tolerance to multiple chemistries and/or inhibitors of multiple modes-of-action.

The compounds and compositions provided herein may also be employed to control herbicide resistant or tolerant weeds. Exemplary resistant or tolerant weeds include, but are not limited to, biotypes resistant or tolerant to acetolactate synthase (ALS) inhibitors, photosystem II inhibitors, acetyl CoA carboxylase (ACCase) inhibitors, synthetic auxins, photosystem I inhibitors, 5-enolpyruvylshikimate-3-phosphate (EPSP) synthase inhibitors, microtubule assembly inhibitors, lipid synthesis inhibitors, protoporphyrinogen oxidase (PPO) inhibitors, carotenoid biosynthesis inhibitors, very long chain fatty acid (VLCFA) inhibitors, phytoene desaturase (PDS) inhibitors, glutamine synthetase inhibitors, 4-hydroxyphenyl-pyruvate-dioxygenase (HPPD) inhibitors, mitosis inhibitors, cellulose biosynthesis inhibitors, herbicides with multiple modes-of-action such as quinclorac, and unclassified herbicides such as arylaminopropionic acids, difenzoquat, endothall, and organoarsenicals. Exemplary resistant or tolerant weeds include, but are not limited to, biotypes with resistance or tolerance to multiple herbicides, multiple chemical classes, and multiple herbicide modes-of-action.

The described embodiments and following examples are for illustrative purposes and are not intended to limit the scope of the claims. Other modifications, uses, or combinations with respect to the compositions described herein will be apparent to a person of ordinary skill in the art without departing from the spirit and scope of the claimed subject matter.

Synthesis of Precursors

Preparation 1: Methyl
4-amino-3,6-dichloropicolinate (Head A)

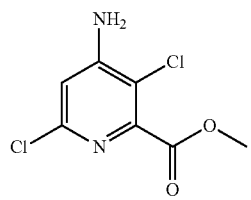

Prepared as described in Fields et al., WO 2001051468 A1.

Preparation 2: Methyl
4-amino-3,6-dichloro-5-fluoropicolinate (Head B)

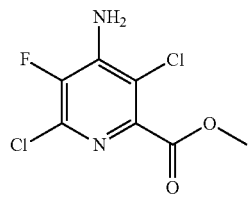

Prepared as described in Fields et al., Tetrahedron Letters 2010, 51, 79-81.

Preparation 3: 2,6-Dichloro-5-methoxy-4-vinyl pyrimidine

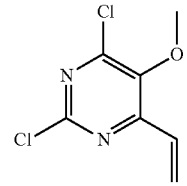

To a solution of commercially available 2,6-dichloro-5-methoxy pyrimidine (100 grams (g), 0.55 moles (mol)) in dry tetrahydrofuran was added, dropwise, 1 molar (M) vinyl magnesium bromide in tetrahydrofuran solvent (124 g, 0.94 mol) over one hour (h) at room temperature. The mixture was then stirred for 4 h at room temperature. Excess Grignard reagent was quenched by addition of acetone (200 milliliters (mL)) while the temperature of the mixture was maintained at a temperature below 20° C. Thereafter, 2,3-dichloro-5,6-dicyano-p-benzoquinone (DDQ; 151 g, 0.67 mol) was added at once and stirred overnight. A yellow solid precipitated out. The solid was filtered and washed with ethyl acetate (500 mL). The filtrate was concentrated under reduced pressure and the resulting crude compound was diluted with ethyl acetate (2 liters (L)). The resulting undissolved, dark, semi-solid was separated by filtration using ethyl acetate. It was further concentrated under reduced pressure to provide a crude compound, which was purified by column chromatography. The compound was eluted with 5% to 10% ethyl acetate in hexane mixture to provide the title compound (70 g, 60%): mp 60-61° C.; $^1$H NMR (CDCl$_3$) δ 3.99 (s, 3H), 5.85 (d, 1H), 6.75 (d, 1H), 6.95 (dd, 1H).

Preparation 4:
2,6-Dichloro-5-methoxy-pyrimidine-4-carbaldehyde

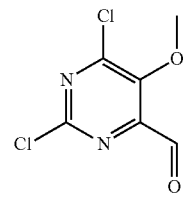

A solution of 2,6-dichloro-5-methoxy-4-vinyl pyrimidine (50 g, 0.24 mol) in dichloromethane:methanol (4:1, 2 L) was cooled to −78° C. Ozone gas was bubbled therethrough for 5 h. The reaction was quenched with dimethyl sulfide (50 mL). The mixture was slowly warmed to room temperature and concentrated under reduced pressure at 40° C. to provide the title compound (50.5 g, 100%); high-performance liquid chromatography (HPLC; 85% acetonitrile buffered with 0.1% volume per volume (v/v) acetic acid).

Preparation 5: Methyl 2,6-dichloro-5-methoxy-pyrimidine-4-carboxylate

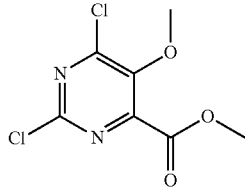

A solution of 2,6-dichloro-5-methoxy-pyrimidine-4-carbaldehyde (50 g, 0.24 mol) in methanol (1 L) and water (60 mL) was prepared. To the solution, sodium bicarbonate (400 g) was added. A 2 M solution of bromine (192 g, 1.2 mol) in methanol/water (600 mL, 9:1) was added dropwise to the pyrimidine solution over 45 minutes (min) at 0° C. while stirring the mixture. The stirring was continued at the same temperature for 1 h. Later, the mixture was stirred at room temperature for 4 h. While stirring, the reaction mixture was thereafter poured onto a mixture of crushed ice (2 L), sodium bisulfite (50 g), and sodium chloride (NaCl; 200 g). The product was extracted with ethyl acetate (1 L×2), and the combined organic layer was dried over sodium sulfate and filtered. Evaporation of the solvent under reduced pressure produced a thick material, which solidified on long standing to afford the title compound (50.8 g, 87%); ESIMS m/z 238 ([M+H]$^+$).

Preparation 6: Methyl 6-amino-2-chloro-5-methoxy-pyrimidine-4-carboxylate (Head C)

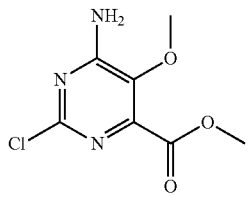

A solution of methyl 2,6-dichloro-5-methoxy-pyrimidine-4-carboxylate (25 g, 0.1 mol) and dimethyl sulfoxide (DMSO) was prepared. To this solution was added, at 0-5° C., a solution of ammonia (2 eq) in DMSO. This mixture was stirred at the same 0-5° C. temperature for 10 to 15 min. Later, the mixture was diluted with ethyl acetate, and the resulting solid was filtered off. The ethyl acetate filtrate was washed with a brine solution and dried over sodium sulfate. Upon concentration, the crude product was obtained. The crude product was stirred in a minimum amount of ethyl acetate and filtered to obtain the pure compound. Additional pure compound was obtained from the filtrate which, after concentration, was purified by flash chromatography. This produced the title compound (11 g, 50%): mp 158° C.; $^1$H NMR (DMSO-d$_6$) δ 3.71 (s, 3H), 3.86 (s, 3H), 7.65 (br s, 1H), 8.01 (br s, 1H).

Preparation 7: Methyl 4-amino-3,6-dichloro-5-iodopicolinate

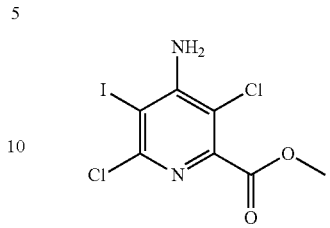

Methyl 4-amino-3,6-dichloropicolinate (10.0 g, 45.2 millimoles (mmol)), periodic acid (3.93 g, 17.2 mmol), and iodine (11.44 g, 45.1 mmol) were dissolved in methanol (30 mL) and stirred at reflux at 60° C. for 27 h. The reaction mixture was concentrated, diluted with diethyl ether, and washed twice with saturated aqueous sodium bisulfate. The aqueous layers were extracted once with diethyl ether, and the combined organic layers were dried over anhydrous sodium sulfate. The product was concentrated and purified by flash chromatography (silica gel, 0-50% ethyl acetate/hexanes) to provide the title compound as a pale yellow solid (12.44 g, 79%): mp 130.0-131.5° C.; $^1$H NMR (400 MHz, CDCl$_3$) δ 5.56 (s, 2H), 3.97 (s, 3H); $^{13}$C NMR (101 MHz, CDCl$_3$) δ 163.80, 153.00, 152.75, 145.63, 112.12, 83.91, 53.21; EIMS m/z 346.

Preparation 8: Methyl 4-amino-3,6-dichloro-5-methylpicolinate (Head D)

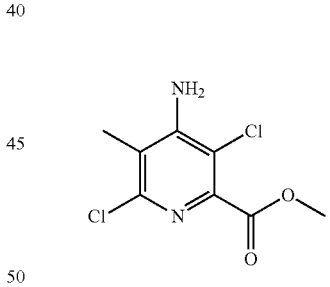

A mixture of methyl 4-amino-3,6-dichloro-5-iodopicolinate (8.1 g, 23.4 mmol), tetramethylstannane (8.35 g, 46.7 mmol), and bis(triphenylphosphine)palladium(II) chloride (2.5 g, 3.5 mmol) in 1,2-dichloroethane (40 mL) was irradiated in a Biotage Initiator microwave at 120° C. for 30 min, with external infrared (IR)-sensor temperature monitoring from the side. The reaction mixture was loaded directly onto a silica gel cartridge and purified by flash chromatography (silica gel, 0-50% ethyl acetate/hexanes) to provide the title compound as an orange solid (4.53 g, 83%): mp 133-136° C.; $^1$H NMR (400 MHz, CDCl$_3$) δ 4.92 (s, 2H), 3.96 (s, 3H), 2.29 (s, 3H); $^{13}$C NMR (101 MHz, CDCl$_3$) δ 164.34, 150.24, 148.69, 143.94, 117.01, 114.60, 53.02, 14.40; ESIMS m/z 236 ([M+H]$^+$), 234 ([M−H]$^−$).

Preparation 9: Methyl 6-amino-2,5-dichloropyrimidine-4-carboxylate (Head E)

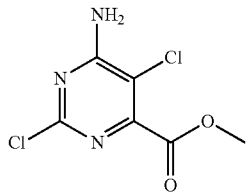

Prepared as described in Epp et al., WO 2007082076 A1.

Preparation 10: Methyl 4-amino-6-chloro-5-fluoro-3-methoxypicolinate (Head F)

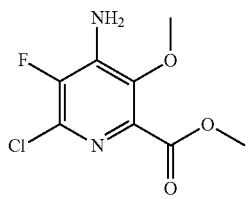

Prepared as described in Epp et al., WO 2013003740 A1.

Preparation 11: Methyl 4-amino-6-chloro-5-fluoro-3-vinylpicolinate (Head G)

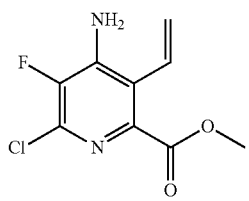

Methyl 4-amino-6-chloro-5-fluoro-3-iodopicolinate (7.05 g, 21.33 mmol, prepared as described in Epp et al., WO 2013003740 A1) and vinyltri-n-butyltin (7.52 mL, 25.6 mmol) were suspended in 1,2-dichloroethane (71.1 mL) and the mixture was degassed with Argon for 10 min. Bis(triphenylphosphine)palladium(II) chloride (1.497 g, 2.133 mmol) was then added and the reaction mixture was stirred at 70° C. overnight (clear orange solution). The reaction was monitored by gas chromatography-mass spectrometry (GC-MS). After 20 h, the reaction mixture was concentrated, adsorbed onto Celite, and purified by column chromatography (SiO$_2$; hexanes/ethyl acetate gradient) to afford the title compound as a light brown solid (3.23 g, 65.7%): mp 99-100° C.; $^1$H NMR (400 MHz, CDCl$_3$) δ 6.87 (dd, J=18.1, 11.6 Hz, 1H), 5.72 (dd, J=11.5, 1.3 Hz, 1H), 5.52 (dd, J=18.2, 1.3 Hz, 1H), 4.79 (s, 2H), 3.91 (s, 3H); $^{19}$F NMR (376 MHz, CDCl$_3$) δ −138.79 (s); EIMS m/z 230.

Preparation 12: Methyl 4-amino-3,5,6-trichloropicolinate (Head H)

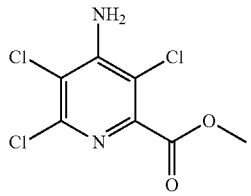

Prepared as described in Finkelstein et al., WO 2006062979 A1.

Preparation 13: Methyl 4-amino-6-bromo-3-chloro-5-fluoropicolinate (Head I)

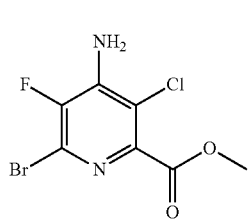

Prepared as described in Arndt et al., US 20120190857 A1.

Preparation 14: Methyl 4-amino-3-chloro-5-fluoro-6-(trimethylstannyl)picolinate (Head J)

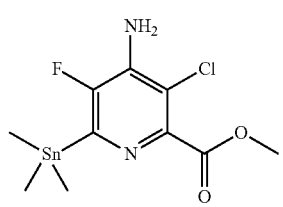

Methyl 4-amino-6-bromo-3-chloro-5-fluoropicolinate (500 mg, 1.8 mmol), 1,1,1,2,2,2-hexamethyldistannane (580 mg, 1.8 mmol) and bis(triphenylphosphine)-palladium(II) chloride (120 mg, 0.18 mmol) were combined in dry dioxane (6 mL), sparged with a stream of nitrogen for 10 min and then heated to 80° C. for 2 h. The cooled mixture was stirred with ethyl acetate (25 mL) and saturated NaCl (25 mL) for 15 min. The organic phase was separated, filtered through diatomaceous earth, dried (Na$_2$SO$_4$) and evaporated. The residue was taken up in ethyl acetate (4 mL), stirred and treated in portions with hexane (15 mL). The milky white solution was decanted from any solids produced, filtered through glass wool and evaporated to give the title compound as an off-white solid (660 mg, 100%): $^1$H NMR (400 MHz, CDCl$_3$) δ 4.63 (d, J=29.1 Hz, 1H), 3.97 (s, 2H), 0.39 (s, 4H); $^{19}$F NMR (376 MHz, CDCl$_3$) δ −130.28; EIMS m/z 366.

Preparation 15: Methyl 4-acetamido-3-chloro-6-(trimethylstannyl)-picolinate (Head K)

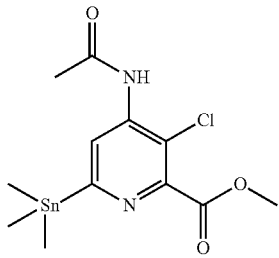

Prepared as described in Balko et al., WO 2003011853 A1.

Preparation 16: Methyl 4-acetamido-3,6-dichloropicolinate (Head L)

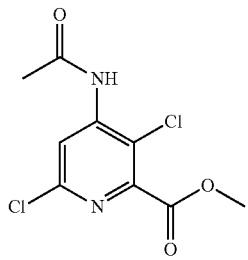 [SMILES: COC(=O)c1nc(Cl)cc(NC(C)=O)c1Cl]

Prepared as described in Fields et al., WO 2001051468 A1.

Preparation 17: Methyl 4-amino-3-chloro-6-iodopicolinate (Head M)

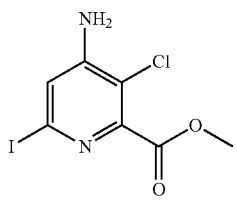

Prepared as described in Balko et al., WO 2007082098 A2.

Preparation 18: Methyl 4-acetamido-3-chloro-6-iodopicolinate (Head N)

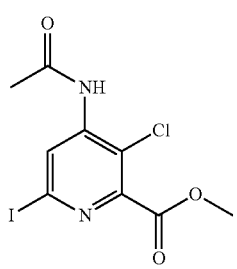 [SMILES: COC(=O)c1nc(I)cc(NC(C)=O)c1Cl]

Prepared as described in Balko et al., WO 2007082098 A2.

Preparation 19: Methyl 4-amino-6-bromo-3,5-difluoropicolinate (Head O)

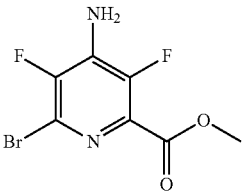

Prepared as described in Fields et al., WO 2001051468 A1.

Preparation 20: Methyl 6-amino-2-chloro-5-vinylpyrimidine-4-carboxylate (Head P)

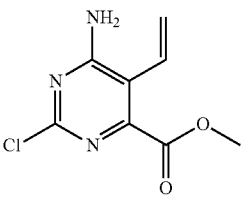

Prepared as described in Epp et al., US20090088322.

Preparation 21: 2,2,5-Trifluoro-6-iodobenzo[d][1,3]dioxole

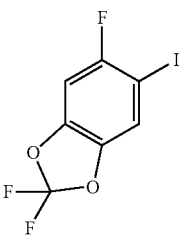 [SMILES: Fc1cc2c(cc1I)OC(F)(F)O2]

2,2,6-Trifluorobenzo[d][1,3]dioxol-5-amine (8.0 g, 42 mmol) was added to concentrated hydrochloric acid (conc. HCl; 200 mL), cooled to 5° C., vigorously stirred and treated dropwise with a solution of sodium nitrite (4.3 g, 63 mmol) in water (10 mL) over 10 min. Stirring was continued for 30 min at 5-10° C. and the mixture was poured cautiously into a solution of sodium iodide (19 g, 130 mmol) in water (200 mL), rapidly stirred with dichloromethane (100 mL). After 20 min the mixture was treated with 10% sodium bisulfite solution (NaHSO$_3$; 20 mL) and stirred for 20 min more. The phases were separated and the aqueous phase was extracted with dichloromethane (75 mL). The combined organic phases were washed with saturated NaCl (30 mL), dried (Na$_2$SO$_4$) and evaporated. The residue was purified by chromatography on silica with hexane to give the title compound as a clear liquid (6 g, 51%): $^1$H NMR (400 MHz, CDCl$_3$) δ 7.41 (d, J=5.0 Hz, 1H), 6.90 (d, J=6.6 Hz, 1H); $^{19}$F NMR (376 MHz, CDCl$_3$) δ −49.63 (s), −95.24 (s); EIMS m/z 302.

Preparation 22: 4,4,5,5-Tetramethyl-2-(2,2,6-trifluorobenzo[d][1,3]dioxol-5-yl)-1,3,2-dioxaborolane

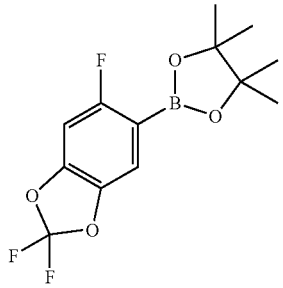 [SMILES: CC1(C)OB(c2cc3c(cc2F)OC(F)(F)O3)OC1(C)C]

2,2,5-Trifluoro-6-iodobenzo[d][1,3]dioxole (1.0 g, 3.3 mmol) was dissolved in dry tetrahydrofuran (10 mL), cooled to 5° C. and treated with isopropylmagnesiumchloride-lithium chloride complex solution (1.3 M; 2.7 mL, 3.5 mmol). The mixture was stirred for 1 h at 5-15° C., treated with 2-isopropoxy-4,4,5,5-tetramethyl-1,3,2-dioxaborolane (720 μL, 660 mg, 3.5 mmol) and stirred for 20 min. The reaction was quenched by addition of saturated ammonium chloride (NH₄Cl; 5 mL) and mixed with ethyl acetate (20 mL) and saturated NaCl (10 mL). The separated organic phase was washed with saturated NaCl (10 mL), dried (Na₂SO₄) and evaporated to give the title compound as a white solid (1.0 g, 100%): $^1$H NMR (400 MHz, CDCl₃) δ 7.37 (d, J=4.3 Hz, 1H), 6.81 (d, J=7.7 Hz, 1H), 1.35 (s, 12H); $^{19}$F NMR (376 MHz, CDCl₃) δ −49.96 (s), −104.21 (s)); EIMS m/z 302.

Preparation 23: 2,2,5-Trifluoro-4-iodobenzo[d][1,3]dioxole

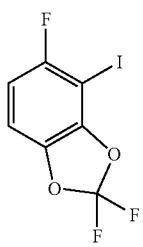

Sec-Butyllithium (1.4 M in cyclohexane; 6.1 mL, 8.5 mmol) was added to dry tetrahydrofuran (15 mL) which had been pre-cooled to −40° C. The solution was cooled to −75° C., treated with 2,2,5-trifluorobenzo[d][1,3]dioxole (1.5 g, 8.5 mmol) and stirred at this temperature for 90 min. This solution was rapidly transferred via cannula into a stirred solution of iodine (2.8 g, 11 mmol) in tetrahydrofuran (25 mL), and the mixture was cooled to −75° C. The mixture was stirred for 1 h during which time the temperature rose to −20° C. The reaction was quenched by addition of saturated NH₄Cl (10 mL) and then combined with 10% NaHSO₃ (15 mL) and ethyl acetate (30 mL). The organic phase was washed with saturated NaCl (10 mL), dried (Na₂SO₄) and evaporated. The material was purified by flash chromatography with hexane to give the title compound as a clear liquid (1.5 g, 58%): $^1$H NMR (400 MHz, CDCl₃) δ 6.97 (dd, J=8.8, 4.0 Hz, 1H), 6.81 (dd, J=11.7, 5.4 Hz, 1H); $^{19}$F NMR (376 MHz, CDCl₃) δ −49.06, −103.15; EIMS m/z 302.

Preparation 24: 5-Bromo-4-chloro-2,2-difluorobenzo[d][1,3]dioxole

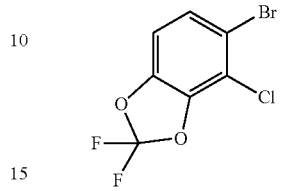

2,2,6,6-Tetramethylpiperidine (2.1 mL, 1.8 g, 12 mmol) was dissolved in dry tetrahydrofuran (15 mL), cooled to −75° C. and treated with n-butyllithium (n-BuLi, 2.5 M; 4.8 mL, 12 mmol), and the mixture was stirred for 30 min at −75° C. 5-Bromo-2,2-difluorobenzo[d][1,3]dioxole (2.0 g, 8.4 mmol) was added, and the mixture was stirred for 2 h at −75° C. 1,1,2-Trichloro-1,2,2-trifluoroethane (2.4 mL, 3.8 g, 20 mmol) was added and stirring was continued for 1.5 h. Saturated NH₄Cl (10 mL) was added, and the mixture was shaken with diethyl ether (30 mL) and water (20 mL). The ether phase was washed with saturated NaCl (10 mL), dried (Na₂SO₄) and evaporated under vacuum. The residue was purified by chromatography on silica with hexane and then repurified by reverse-phase HPLC using 75% acetonitrile to give the title compound as a clear liquid (640 mg, 28%): $^1$H NMR (400 MHz, CDCl₃) δ 7.38 (dd, J=8.5, 5.1 Hz, 1H), 6.90 (dd, J=9.0, 4.7 Hz, 1H); EIMS m/z 332.

Preparation 25: 2-(4-Chloro-2,2-difluorobenzo[d][1,3]dioxol-5-yl)-4,4,5,5-tetramethyl-1,3,2-dioxaborolane

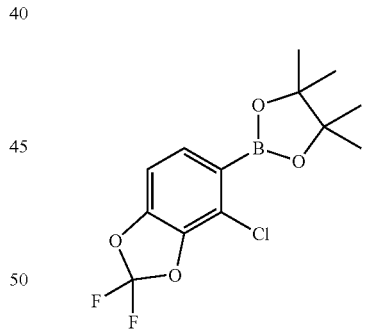

5-Bromo-4-chloro-2,2-difluorobenzo[d][1,3]dioxole (1.0 g, 3.7 mmol) was dissolved in dry tetrahydrofuran (12 mL), cooled to −20 to −30° C. and treated in portions with isopropylmagnesium chloride-lithium chloride complex solution (1.3 M; 3.1 mL, 4.1 mmol). After 90 min at −20 to 0° C., 2-isopropoxy-4,4,5,5-tetramethyl-1,3,2-dioxaborolane (830 μL, 750 mg, 4.1 mmol) was added, and stirring was continued at 0-20° C. for 90 min. The reaction was quenched by addition of saturated NH₄Cl (10 mL), and the mixture was extracted with ethyl acetate (30 mL). The aqueous phase was extracted again with ethyl acetate (15 mL), and the combined organic phases were washed with saturated NaCl (15 mL), dried (Na₂SO₄) and evaporated to give the title compound as a white solid (1.2 g, ca. 100%): $^1$H NMR (400 MHz, CDCl₃) δ

7.52 (d, J=8.1 Hz, 1H), 6.99-6.94 (m, 1H), 1.36 (s, 12H); $^{19}$F NMR (376 MHz, CDCl$_3$) δ −49.62 (s); EIMS m/z 318.

Preparation 26:
4-Fluorobenzo[d][1,3]dioxole-2-thione

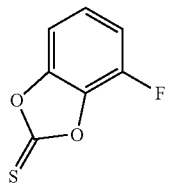 [SMILES: Fc1cccc2oc(=S)oc12]

3-Fluorobenzene-1,2-diol (5.0 g, 39 mmol) and thiophosgene (3.3 mL, 5.0 g, 42 mmol) were combined in chloroform (50 mL), cooled to 10° C. and treated dropwise over 30 min with sodium hydroxide (10% solution; 36 g, 90 mmol) with vigorous stirring. After stirring for 2 h at ambient temperature, the chloroform was removed under vacuum, and the solid formed was collected by filtration and washed with water. The solid was dissolved in ethyl acetate (100 mL), the solution was washed with water (30 mL) and saturated NaCl (30 mL), dried (Na$_2$SO$_4$) and evaporated. The crude solid was purified by chromatography on silica with 0-30% ethyl acetate-hexane to give the title compound (1.5 g, 77%): mp 58-59° C.; $^1$H NMR (400 MHz, CDCl$_3$) δ 7.28 (m, 1H), 7.12 (m, 2H); $^{19}$F NMR (376 MHz, CDCl$_3$) δ −131.32; EIMS m/z 170.

Preparation 27:
5-Bromo-2,2,4-trifluorobenzo[d][1,3]dioxole

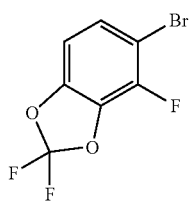

4-Fluorobenzo[d][1,3]dioxole-2-thione (4.8 g, 28 mmol) was dissolved in dichloromethane (75 mL), cooled to −30° C. and treated with hydrogen fluoride (HF)-Pyridine (70 weight percent (wt %) solution; 18 mL, 20 g, 140 mmol). 1,3-Dibromo-5,5-dimethylimidazolidine-2,4-dione (9.7 g, 34 mmol) was added in portions over 30 min. The mixture was stirred for 2 h at −20 to −30° C. and then stirred with 5% NaHSO$_3$ solution (20 mL) for 10 min. The organic phase was separated, dried (Na$_2$SO$_4$), and the dichloromethane was carefully removed by distillation through a 200 millimeter (mm) Vigreux column at atmospheric pressure. The pressure was reduced to ca 150 millimeters of mercury (mmHg) when most of the dichloromethane had been taken overhead. Distillation was continued and the fraction boiling at 45-55° C. was collected to provide the title compound as a clear liquid (3.2 g, 45%): $^1$H NMR (400 MHz, CDCl$_3$) δ 7.28 (dd, J=8.6, 6.2 Hz, 1H), 6.81 (dd, J=8.6, 1.3 Hz, 1H); $^{19}$F NMR (376 MHz, CDCl$_3$) δ −49.25 (s), −126.72 (s); EIMS m/z 254.

Preparation 28: 4,4,5,5-Tetramethyl-2-(2,2,4-trifluorobenzo[d][1,3]dioxol-5-yl)-1,3,2-dioxaborolane

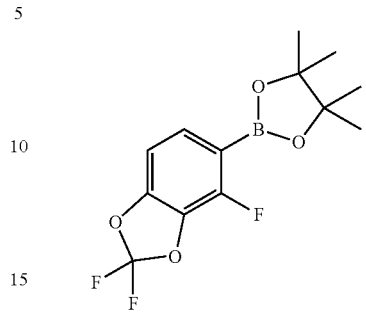

5-Bromo-2,2,4-trifluorobenzo[d][1,3]dioxole (4.0 g, 16 mmol) was dissolved in 20 mL dry tetrahydrofuran, cooled to −20° C. and treated with isopropylmagnesium chloride-lithium chloride complex (1.3 M in tetrahydrofuran; 13 mL, 17 mmol) in portions over 10 min. After stirring for 30 min at −20 to 0° C., 2-isopropoxy-4,4,5,5-tetramethyl-1,3,2-dioxaborolane (3.1 g, 17 mmol) was added, and stirring was continued for 1 h at 10-15° C. After treatment with saturated NH$_4$Cl solution (10 mL), the mixture was diluted with ethyl acetate (50 mL). The organic phase was washed with saturated NaCl (15 mL), dried (Na$_2$SO$_4$) and evaporated to give the title compound as a brown solid (3.5 g, 72%): $^1$H NMR (400 MHz, CDCl$_3$) δ 7.46 (d, J=26.5 Hz, 1H), 6.90 (dd, J=18.5, 4.5 Hz, 1H), 1.35 (s, 12H); $^{19}$F NMR (376 MHz, CDCl$_3$) δ −49.70 (s), −126.00 (s); EIMS m/z 302.

Preparation 29: 2-(2,2-Difluoro-4-methylbenzo[d][1,3]dioxol-5-yl)-5,5-dimethyl-1,3,2-dioxaborinane

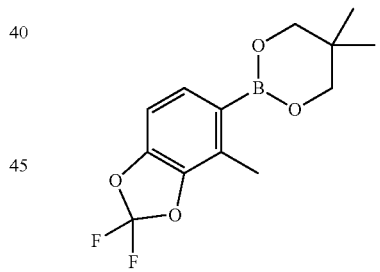

5-Bromo-2,2-difluoro-4-methylbenzo[d][1,3]dioxole (prepared as described in Nakamura, Yuji; Mitani, Shigeru; Tsukuda, Shintar, WO2007069777; 1.0 g, 4.0 mmol) was combined in dry DMSO (10 mL) with 1,1'-bis(diphenylphosphino)ferrocenedichloro-palladium(II) complex with dichloromethane (330 mg, 0.40 mmol), potassium acetate (1.2 g, 12 mmol) and 5,5,5',5'-tetramethyl-2,2'-bi(1,3,2-dioxaborinane) (950 mg, 4.2 mmol), heated to 80° C. for 4 h and then left to stand overnight. The mixture was shaken with ethyl acetate (50 mL) and water (30 mL). The organic phase was washed with water, washed with saturated NaCl, dried (Na$_2$SO$_4$), and evaporated. The residue was purified by chromatography on silica with 5-50% ethyl acetate-hexane to give the title compound (540 mg, 48%): $^1$H NMR (400 MHz, CDCl$_3$) δ 7.55-7.48 (m, 1H), 6.88-6.79 (m, 1H), 5.51-5.47 (m, 1H), 3.83-3.64 (m, 5H), 1.02 (d, J=4.9 Hz, 7H); $^{19}$F NMR (376 MHz, CDCl$_3$) δ-49.91 (d, J=7.1 Hz); EIMS m/z 284.

Preparation 30: 1-Bromo-2-(2-bromo-1,1,2,2-tetrafluoroethoxy)-3-fluorobenzene

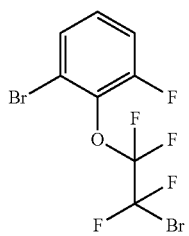

2-Bromo-6-fluorophenol (10.2 g, 53 mmol), potassium carbonate (7.3 g, 53 mmol), 1,2-dibromo-tetrafluoroethane (21 g, 80 mmol) and 1-butanethiol (1.1 g, 12 mmol) were combined in dry N,N-dimethylformamide (75 mL) and heated to 50° C. in a stirred pressure reactor. After cooling, the contents were mixed with 1.0 M sodium hydroxide (NaOH; 100 mL) and extracted three times with diethyl ether (80 mL portions). The combined extracts were washed with water (15 mL), 2.0 M NaOH (45 mL), dried ($Na_2SO_4$) and concentrated by rotary evaporation. The material was purified by silica gel chromatography eluting with hexane to afford the title compound as a clear liquid (15 g, 76%): $^1$H NMR (400 MHz, $CDCl_3$) δ 7.48-7.39 (m, 1H), 7.22-7.14 (m, 2H); EIMS m/z 368.

Preparation 31: 2,2,3,3,7-Pentafluoro-2,3-dihydrobenzofuran

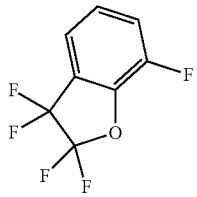

1-Bromo-2-(2-bromo-1,1,2,2-tetrafluoroethoxy)-3-fluorobenzene (14 g, 38 mmol), copper powder (12.2 g, 192 mmol) and 2,2'-bipyridine (610 mg, 3.9 mmol) were combined in dry DMSO (55 mL) and heated to 150° C. for 1.5 h. Vacuum (ca 20 mm) was applied to the reactor and distillate was taken overhead until the pot temperature reached 100° C. The distillate containing the product and DMSO was diluted with 1:1 diethyl ether-pentane (30 mL) and washed (3×5 mL) with water, dried, and distilled at 1 atmosphere (atm) through a 200 mm Vigreux column to remove the bulk of the solvents. Vacuum (ca 20 mmHg) was applied and the fraction boiling at 60-65° C. was collected to afford the title compound as a clear liquid (5.1 g, 64%): $^1$H NMR (400 MHz, $CDCl_3$) δ 7.40-7.31 (m, 2H), 7.25-7.17 (m, 1H); EIMS m/z 210.

Preparation 32: 2,2,3,3,7-Pentafluoro-6-iodo-2,3-dihydrobenzofuran

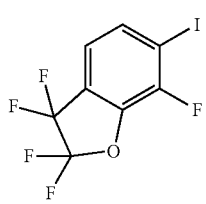

2,2,3,3,7-Pentafluoro-2,3-dihydrobenzofuran (500 mg, 2.4 mmol) was added in portions to a −70° C. solution of lithium diisopropylamide (LDA) prepared in dry tetrahydrofuran (7 mL) from diisopropylamine (380 mg, 3.8 mmol) and 2.5 M n-BuLi (1.4 mL, 3.6 mmol). After 40 min at −70° C. a solution of iodine (1.0 g, 4.0 mmol) in tetrahydrofuran (5 mL) was added over 15 min. After 20 min at −70° C., the mixture was warmed to −20° C. and quenched by addition of saturated $NH_4Cl$. The mixture was treated with 10% $NaHSO_3$ (15 mL), stirred for 10 min and extracted twice with diethyl ether (15 mL portions). The combined extracts were dried ($Na_2SO_4$) and evaporated. The residue was purified by reverse-phase HPLC eluting with 85% acetonitrile-water to afford the title compound (200 mg, 25%): $^1$H NMR (400 MHz, $CDCl_3$) δ 7.25 (dd, J=8.1, 4.8 Hz, 1H), 6.63 (dd, J=8.0, 1.1 Hz, 1H), 4.13 (s, 3H); EIMS m/z 336.

Preparation 33: 5-Bromo-2,2-difluoro-4-methoxybenzo[d][1,3]dioxole

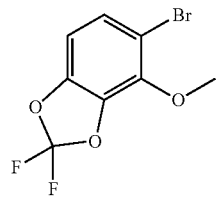

A solution of LDA was prepared from diisopropylamine (4.2 g, 41 mmol) and n-BuLi (2.5 M; 15.4 mL, 38 mmol) in dry tetrahydrofuran (100 mL). The solution was cooled to −70° C. and treated in portions with 5-bromo-2,2-difluorobenzo[d][1,3]dioxole (7.0 g, 30 mmol). After 2 h at −70° C., trimethylborate (4.3 g, 41 mmol) was added in portions, stirred at −70° C. for 1.5 h and then allowed to warm to ambient overnight. The mixture was cooled to −30 to −40° C. and treated carefully with 28% peracetic acid. The mixture was stirred for 30 min at −30° C., warmed to 5-10° C., treated with 10% $NaHSO_3$ (100 mL) solution and stirred for 20 min. The mixture was acidified by addition of 6 M HCl and diluted with saturated NaCl solution (75 mL). The mixture was extracted ethyl acetate (2×100 mL) and the combined extracts were washed with saturated NaCl (50 mL), dried ($Na_2SO_4$) and rotary evaporated. The crude phenol was dissolved in dry DMSO (50 mL), treated with 95% NaH (750 mg, 30 mmol) and stirred for 30 min to produce a clear solution. Methyl iodide (5.0 g, 35 mmol) was added in portions, and the mixture was stirred for 20 h at 20° C. An additional 200 mg NaH were added and stirring was continued for 1 h more. The mixture was poured into water (100 mL) and extracted diethyl ether (2×75 mL). The combined extracts were washed with water (2×20 mL), with saturated NaCl (20 mL), dried ($Na_2SO_4$) and evaporated. The crude material was purified by chromatography on silica with a 0-20% ethyl acetate-hexane gradient to afford the title compound as a clear liquid (2.5 g, 31%): $^1$H NMR (400 MHz, $CDCl_3$) δ 7.25 (d, J=8.5 Hz, 1H), 6.63 (d, J=8.5 Hz, 1H), 4.13 (s, 3H); $^{19}$F NMR (376 MHz, $CDCl_3$) δ −49.66; EIMS m/z 266.

Preparation 34: 2-(2,2-Difluoro-4-methoxybenzo[d][1,3]dioxol-5-yl)-4,4,5,5-tetramethyl-1,3,2-dioxaborolane

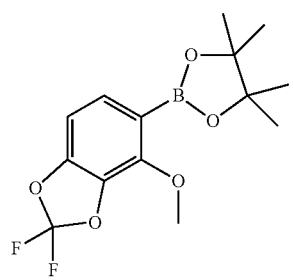 [SMILES: COc1c(B2OC(C)(C)C(C)(C)O2)ccc2c1OC(F)(F)O2]

2-(2,2-Difluoro-4-methoxybenzo[d][1,3]dioxol-5-yl)-4,4,5,5-tetramethyl-1,3,2-dioxaborolane (1.1 g, 4.1 mmol) was dissolved in dry tetrahydrofuran (10 mL), cooled to 0-5° C. and treated in portions with isopropylmagnesium chloride-lithium chloride solution (1.3 M; 3.5 mL, 4.5 mmol). The mixture was stirred for 1 h at 0-5° C., treated with 2-isopropoxy-4,4,5,5-tetramethyl-1,3,2-dioxaborolane (840 mg, 4.5 mmol) and stirred at 20° C. for 90 min. The mixture was treated with saturated NH₄Cl (5 mL) and stirred for 10 min. The mixture was extracted with ethyl acetate (30 mL) and the extract was washed with saturated NaCl (10 mL), dried (Na₂SO₄) and rotary evaporated to give the title compound as an oil which solidified on standing (1.2 g, 93%): $^1$H NMR (400 MHz, CDCl₃) δ 7.42 (d, J=8.0 Hz, 1H), 6.72 (d, J=8.0 Hz, 1H), 4.06 (s, 3H), 1.34 (s, 12H); $^{19}$F NMR (376 MHz, CDCl₃) δ −50.09; EIMS m/z 314.

Preparation 35: 3,5-Difluorobenzene-1,2-diol

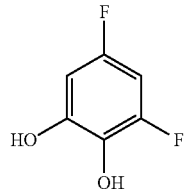

3,5-Difluoro-2-methoxyphenol (1.0 g, 6.3 mmol, prepared as described in Jones, Lyn H.; Randall, Amy; Barba, Oscar; Selby, Matthew D., *Organic & Biomolecular Chemistry* 2007, 5, 3431-3433) was dissolved in dry dichloromethane (11 mL), cooled to −20 to −30° C. and treated in portions with boron tribromide (BBr₃) solution in dichloromethane (1.0 M; 13 mL, 13 mmol). The cooling bath was removed and the mixture was stirred for 20 h at 20° C. The mixture was cooled to −30° C., treated in portions with water (3 mL) and then warmed to 20° C. 6 M HCl (10 mL) and ethyl acetate (30 mL) were added, and the mixture was stirred for 20 min to produce two clear phases. The aqueous phase was extracted with ethyl acetate (20 mL), and the combined organic phases were washed with saturated NaCl (10 mL), dried (Na₂SO₄) and rotary evaporated to give the title compound as an oil which solidified upon standing (720 mg, 78%): $^1$H NMR (400 MHz, CDCl₃) δ 6.51 (ddd, J=9.5, 2.8, 2.1 Hz, 1H), 6.45 (ddd, J=10.3, 8.7, 2.9 Hz, 1H), 5.71 (s, 1H), 5.06 (s, 1H); $^{19}$F NMR (376 MHz, CDCl₃) δ −119.56, −136.16; EIMS m/z 146.

Preparation 36:
4,6-Difluorobenzo[d][1,3]dioxole-2-thione

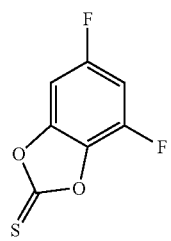 [SMILES: Fc1cc(F)c2oc(=S)oc2c1]

3,5-Difluorobenzene-1,2-diol (670 mg, 4.6 mmol) was stirred in dry chloroform (8 mL), treated with thiophosgene (580 mg, 5.0 mmol), cooled to 5-10° C., and treated dropwise with 10% NaOH solution (4.2 g, 11 mmol) over 45 min. After 30 min, the volatiles were removed by rotary evaporation and the residual solid was collected by filtration and washed with water. The solid was dissolved in ethyl acetate (30 mL), washed with water (2×20 mL), washed with saturated NaCl (1×10 mL), dried (Na₂SO₄), and evaporated. The residue was purified by chromatography on silica with a 0-20% ethyl acetate-hexane gradient to give the title compound (710 mg, 82%): $^1$H NMR (400 MHz, CDCl₃) δ 6.95 (ddd, J=6.8, 2.3, 1.4 Hz, 1H), 6.89 (td, J=9.5, 2.3 Hz, 1H); $^{19}$F NMR (376 MHz, CDCl₃) δ −109.99 (s), −127.93 (s); EIMS m/z 188.

Preparation 37:
2,2,4,6-Tetrafluorobenzo[d][1,3]dioxole

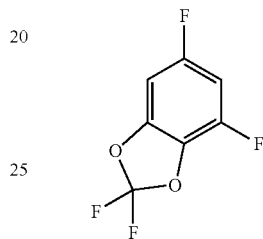

4,6-Difluorobenzo[d][1,3]dioxole-2-thione (9.0 g, 48 mmol) was dissolved in dry dichloromethane (100 mL) in a polyethylene bottle, cooled to −30 to −35° C. and treated with 70% pyridine-hydrogen fluoride complex (68 g, 480 mmol). The mixture was maintained at this temperature and treated in portions with N-iodosuccinimide (32 g, 144 mmol) over 1 h. The mixture was stirred for 3 h as it warmed to 5° C. After cooling to −30° C., the mixture was treated in portions with 20% NaHSO₃ (75 mL) with vigorous stirring. The mixture was filtered through diatomaceous earth to remove dark solids. The separated aqueous phase was extracted with dichloromethane (75 mL), and the combined extracts were washed with water (2×50 mL) and washed with saturated NaCl (1×50 mL). The solvent was removed by atmospheric distillation through a 300 mm Vigreux column. The residue was distilled at 310 mmHg, and the fraction collected at 40-45° C. contained the title compound as a clear liquid (1.3 g, 14%): $^1$H NMR (400 MHz, CDCl₃) δ 6.71 (m, 1H), 6.68 (m, 1H); $^{19}$F NMR (376 MHz, CDCl₃) δ −49.47, −113.41, −131.95; EIMS m/z 194.

Preparation 38:
2,2,4,6-Tetrafluoro-5-iodobenzo[d][1,3]dioxole

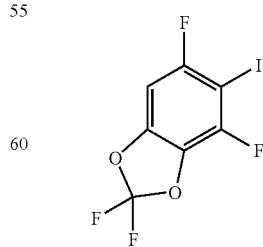

2,2,4,6-Tetrafluorobenzo[d][1,3]dioxole (500 mg, 2.6 mmol) was dissolved in dry tetrahydrofuran (7 mL), cooled to −70° C., treated dropwise with sec-BuLi (1.3 M; 2.1 mL, 2.7 mmol) and stirred for 1 h at −70° C. This mixture was treated dropwise with a solution of iodine (1.1 g, 4.4 mmol) in tetrahydrofuran (5 mL) over 10 min. After 2 h at −70° C., the mixture was treated with saturated NH$_4$Cl, extracted with ethyl ether, dried (Na$_2$SO$_4$) and evaporated. The material was purified by reverse phase HPLC with 85% acetonitrile-water to give the title compound (250 mg; 30%): $^1$H NMR (400 MHz, CDCl$_3$) δ 6.80-6.77 (d, J=8.7 Hz, 1H), 6.77-6.75 (d, J=8.7 Hz, 1H); $^{19}$F NMR (376 MHz, CDCl$_3$) δ −48.72, −99.73, −132.62; EIMS m/z 320.

Preparation 39: 4,6-Difluorobenzo[d][1,3]dioxole

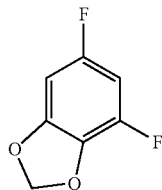 [SMILES: Fc1cc(F)c2c(c1)OCO2]

3,5-Difluorobenzene-1,2-diol (10 g, 69 mmol) was dissolved in dry N,N-dimethylformamide (100 mL), treated with cesium carbonate (56 g, 170 mmol) and stirred for 30 min at 20° C. Bromochloromethane (12 g, 90 mmol) was added and the mixture was heated and stirred at 60° C. for 19 h. After cooling, the mixture was shaken with water (100 mL) and diethyl ether (100 mL). The aqueous phase was extracted again with ether (50 mL). The combined extracts were washed with water (2×20 mL), washed with saturated NaCl (1×10 mL) and dried (Na$_2$SO$_4$). The bulk of the ether was removed by atmospheric distillation through a 300 mm Vigreux column. The pressure was reduced to 75 mmHg and the product was distilled at 70-90° C. to give the title compound as a thick oil (3.0 g, 28%): $^1$H NMR (400 MHz, CDCl$_3$) δ 6.45 (m, 1H), 6.42 (d, J=2.4 Hz, 1H), 6.39 (d, J=2.4 Hz, 1H), 6.02 (s, 2H); $^{19}$F NMR (376 MHz, CDCl$_3$) δ −117.99, −135.90; EIMS m/z 158.

Preparation 40: 4,6-Difluoro-5-iodobenzo[d][1,3]dioxole

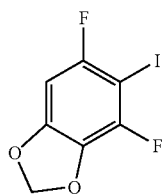 [SMILES: Fc1cc2c(c(F)c1I)OCO2]

4,6-Difluorobenzo[d][1,3]dioxole (300 mg, 1.9 mmol) and N-iodosuccinimide (640 mg, 2.9 mmol) were combined in dry acetonitrile (5 mL), treated with trifluoroacetic acid (430 mg, 3.8 mmol) and stirred for 20 h. The mixture was stirred with a solution of NaHSO$_3$ (100 mg in 2 mL water) and then shaken with ethyl acetate (30 mL) and saturated NaCl (5 mL). The organic phase was washed with saturated NaCl (5 mL), dried (Na$_2$SO$_4$) and evaporated. The material was purified by chromatography on silica with a 0-5% ethyl acetate-hexane gradient to give the title compound as a white solid (410 mg, 76%): mp 65-66° C. $^1$H NMR (400 MHz, CDCl$_3$) δ 6.54 (dd, J=6.9, 1.6 Hz, 1H), 6.07 (s, 2H); $^{19}$F NMR (376 MHz, CDCl$_3$) δ −99.31, −117.98; EIMS m/z 284.

Preparation 41: 4,4,5,5-Tetramethyl-2-(2-methylbenzo[d][1,3]dioxol-5-yl)-1,3,2-dioxaborolane

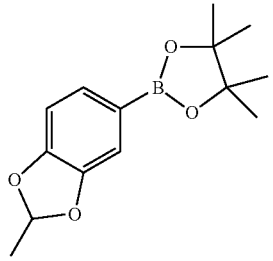

5-Bromo-2-methylbenzo[d][1,3]dioxole (1.0 g, 4.7 mmol, prepared as described in Matyus, Peter; Magyar, Kalman; Pihlavista, Marjo; Gyires, Klara; Haider, Norbert; Wang, Yinghua; Woda, Patrick; Dunkel, Petra; Toth-Sarudy, Eva; Turos, Gyoergy, WO2010029379) was dissolved in dry tetrahydrofuran (10 mL), cooled to −70° C. and treated with n-BuLi (2.5 M; 2.1 mL, 4.7 mmol) over 5 min. After 1 h, 2-isopropoxy-4,4,5,5-tetramethyl-1,3,2-dioxaborolane (1.1 g, 6.0 mmol) was added and the mixture was stirred for 90 min at −70 to −30° C. After addition of saturated NH$_4$Cl (5 mL), the mixture was shaken with ethyl acetate (40 mL) and saturated NaCl (10 mL), dried (Na$_2$SO$_4$) and evaporated. The material was purified by chromatography on silica with a 0-30% ethyl acetate-hexane gradient to give the title compound (730 mg, 59%): $^1$H NMR (400 MHz, CDCl$_3$) δ 7.33 (dd, J=7.7, 1.1 Hz, 1H), 7.18 (d, J=0.9 Hz, 1H), 6.77 (d, J=7.8 Hz, 1H), 6.25 (q, J=5.0 Hz, 1H), 1.66 (d, J=4.9 Hz, 3H), 1.32 (s, 12H); EIMS m/z 262.

Preparation 42: 2-(Benzo[d][1,3]oxathiol-5-yl)-4,4,5,5-tetramethyl-1,3,2-dioxaborolane

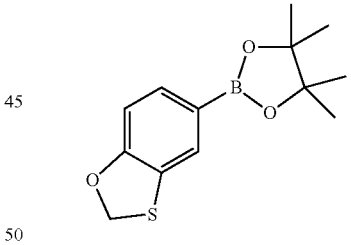

5-Bromobenzo[d][1,3]oxathiole (1.0 g, 4.6 mmol, prepared as described in Cabiddu, Salvatore; Cerioni, Giovanni; Cocco, Maria Teresa; Maccioni, Antonio; Plumitallo, Antonio, *Journal of Heterocyclic Chemistry* 1982, 19, 135-139) was dissolved in dry tetrahydrofuran (12 mL), cooled to −70° C., treated in portions with n-BuLi (2.5 M; 1.9 mL, 4.8 mmol) and stirred at −70° C. for 30 min. 4,4,5,5-Tetramethyl-1,3,2-dioxaborolane (900 mg, 4.8 mmol) was added and stirring was continued for 1.5 h during which the temperature rose to −30° C. The mixture was treated with saturated NH$_4$Cl (5 mL) and extracted with ethyl acetate (2×25 mL). The combined extracts were washed with saturated NaCl (10 mL), dried (Na$_2$SO$_4$) and evaporated to give the title compound which was used without further purification (1.2 g, 99%): $^1$H NMR (400 MHz, CDCl$_3$) δ 7.62 (d, J=1.1 Hz, 1H), 7.48 (dd, J=8.0, 1.3 Hz, 1H), 6.82 (d, J=8.1 Hz, 1H), 5.69 (s, 2H), 1.32 (s, 12H); EIMS m/z 264.

Preparation 43:
2,2-Difluoro-5-methoxy-6-nitrobenzo[d][1,3]dioxole

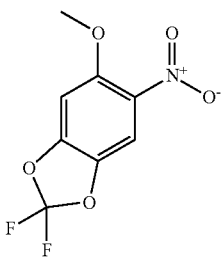 [SMILES: COc1cc2c(cc1[N+](=O)[O-])OC(F)(F)O2]

2,2,5-Trifluoro-6-nitrobenzo[d][1,3]dioxole (2.5 g, 11 mmol) was dissolved in dry methanol (20 mL), treated with 30% sodium methoxide solution (3.1 g, 17 mmol), and stirred at 20° C. for 1 h. After excess methoxide was neutralized by addition of acetic acid, the volatiles were removed by rotary evaporation. The residue was taken up in ethyl acetate (50 mL), washed with saturated NaHCO$_3$ (10 mL), saturated NaCl (10 mL), dried (Na$_2$SO$_4$) and evaporated. The material was purified by chromatography on silica with a 0-30% ethyl acetate-hexane gradient to give the title compound as a white solid (1.8 g, 70%): mp 84-85° C. $^1$H NMR (400 MHz, CDCl$_3$) δ 7.71 (s, 1H), 6.89 (s, 1H), 3.98 (s, 3H); $^{19}$F NMR (376 MHz, CDCl$_3$) δ −49.90 (s); EIMS m/z 233.

Preparation 44:
2,2-Difluoro-6-methoxybenzo[d][1,3]dioxol-5-amine

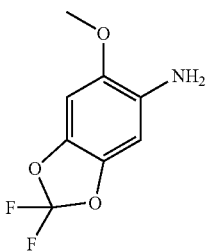

2,2-Difluoro-5-methoxy-6-nitrobenzo[d][1,3]dioxole (1.7 g, 7.3 mmol) was dissolved in ethyl acetate (50 mL) and treated with 5% palladium on carbon (200 mg) and hydrogen at 40-50 pounds per square inch (psi) on a shaker. After 90 min, the catalyst was removed by filtration, the solvent was removed by evaporation, and the product dried under vacuum to give the title compound as a brown solid (1.5 g, qt (quantitative)): $^1$H NMR (400 MHz, CDCl$_3$) δ 6.63 (s, 1H), 6.50 (s, 1H), 3.82 (s, 3H), 3.76 (d, J=23.0 Hz, 2H); $^{19}$F NMR (376 MHz, CDCl$_3$) δ −50.32 (s); EIMS m/z 203.

Preparation 45:
2,2-Difluoro-5-iodo-6-methoxybenzo[d][1,3]dioxole

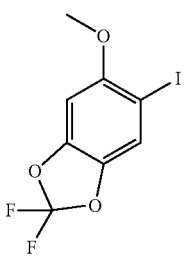

2,2-Difluoro-6-methoxybenzo[d][1,3]dioxol-5-amine (1.4 g, 6.9 mmol) was dissolved in dichloromethane (5 mL) and added in portions to rapidly stirred concentrated HCl (75 mL) to form a loose white slurry. The mixture was cooled to 0-5° C. and treated in portions with sodium nitrite (710 mg, 10 mmol) in water (10 mL). After 40 min, this mixture was poured as a thin stream into a solution of sodium iodide (3.1 g, 21 mmol) in water (75 mL) rapidly stirred with dichloromethane (50 mL). After 45 min, the mixture was stirred with 15% NaHSO$_3$ solution (20 mL) for 10 min. The separated aqueous phase was extracted with dichloromethane (30 mL), and the combined extracts were washed with saturated NaCl (15 mL), dried (Na$_2$SO$_4$) and evaporated. The material was purified by chromatography on silica with a 0-15% ethyl acetate-hexane gradient to afford the title compound as a white solid (1.8 g, 83%): mp 50-51° C.; $^1$H NMR (400 MHz, CDCl$_3$) δ 7.45 (s, 1H), 6.69 (s, 1H), 3.86 (s, 3H); $^{19}$F NMR (376 MHz, CDCl$_3$) δ −49.81 (s); EIMS m/z 314.

Preparation 46: 2-(2,2-Difluoro-6-methoxybenzo[d][1,3]dioxol-5-yl)-4,4,5,5-tetramethyl-1,3,2-dioxaborolane

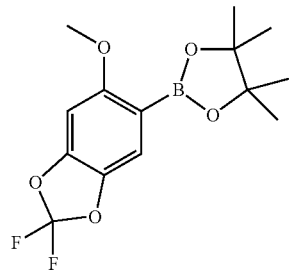 [SMILES: COc1cc2c(cc1B1OC(C)(C)C(C)(C)O1)OC(F)(F)O2]

2,2-Difluoro-5-iodo-6-methoxybenzo[d][1,3]dioxole (1.6 g, 5.0 mmol) was dissolved in dry tetrahydrofuran (15 mL), cooled to 0-5° C. and treated in portions with isopropylmagnesium lithium chloride (1.3 M; 4.1 mL, 5.3 mmol). After 50 min, 2-isopropoxy-4,4,5,5-tetramethyl-1,3,2-dioxaborolane (1.0 g, 5.4 mmol) was added and stirring was continued for 40 min at 15-20° C. The mixture was treated with saturated NH$_4$Cl (10 mL) and then mixed with saturated NaCl (10 mL) and ethyl acetate (20 mL). The organic phase was washed with saturated NaCl (10 mL), dried (Na$_2$SO$_4$) and evaporated to give title compound as a thick oil which was used without further purification (1.4 g, 89%): $^1$H NMR (400 MHz, CDCl$_3$) δ 7.35 (s, 1H), 6.65 (s, 1H), 3.81 (s, 3H), 1.34 (s, 12H); $^{19}$F NMR (376 MHz, CDCl$_3$) δ −50.17 (s); EIMS m/z 314.

Preparation 47: 2-(6-Chloro-2,2-difluorobenzo[d][1,3]dioxol-5-yl)-4,4,5,5-tetramethyl-1,3,2-dioxaborolane

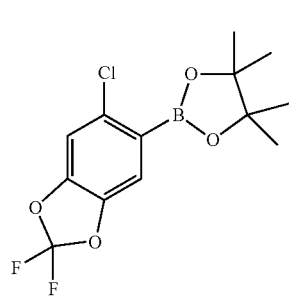 [SMILES: CC1(C)OB(c2cc3c(cc2Cl)OC(F)(F)O3)OC1(C)C]

5-Bromo-6-chloro-2,2-difluorobenzo[d][1,3]dioxole (1.0 g, 3.7 mmol) was dissolved in dry tetrahydrofuran (7 mL), cooled to 0-5° C. and treated in portions with isopropylmagnesium lithium chloride (1.3 M; 3.0 mL, 3.9 mmol). After 30 min, 2-isopropoxy-4,4,5,5-tetramethyl-1,3,2-dioxaborolane (730 mg, 4.0 mmol) was added, and stirring was continued for 45 min at 10-15° C. Saturated NH₄Cl (10 mL) was added and the mixture was shaken with ethyl acetate (20 mL) and saturated NaCl (10 mL). The organic phase was washed with saturated NaCl (10 mL), dried (Na₂SO₄) and evaporated to give the title compound as a white solid (1.2 g, qt): $^1$H NMR (400 MHz, DMSO-d₆) δ 7.64 (s, 1H), 7.53 (s, 1H), 1.30 (s, 12H); $^{19}$F NMR (376 MHz, DMSO-d₆) δ −48.97 (s); EIMS m/z 318.

Preparation 48: 2-(7-Methoxybenzo[d][1,3]dioxol-5-yl)-4,4,5,5-tetramethyl-1,3,2-dioxaborolane

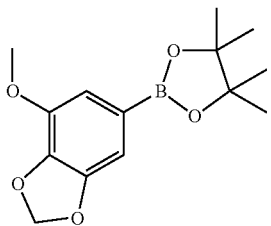 [SMILES: COc1cc(B2OC(C)(C)C(C)(C)O2)cc2c1OCO2]

6-Bromo-4-methoxybenzo[d][1,3]dioxole (1.5 g, 6.5 mmol, prepared according to Shirasaka, Tadashi; Takuma, Yuki; Imaki, Naoshi. *Synthetic Communications* 1990, 20, 1223-1232) was dissolved in dry tetrahydrofuran (25 mL), cooled to 5° C. and treated with isopropylmagnesium lithium chloride (1.3 M; 5.2 mL, 6.8 mmol). After 50 min at 10° C., the temperature was raised to 40° C. and stirred for 5 h. The mixture was cooled to 20° C., treated with 2-isopropoxy-4,4,5,5-tetramethyl-1,3,2-dioxaborolane (1.3 g, 7.1 mmol) and stirred for 3 h. The mixture was treated with saturated NH₄Cl (2 mL), followed by 1 M HCl (8 mL) and ethyl acetate (20 mL), and then was stirred for 10 min. The organic phase was washed with saturated NaCl (10 mL), dried (Na₂SO₄) and evaporated. The product was purified by flash chromatography with dichloromethane to give the title compound as a white solid (600 mg; 33%): mp 86-88° C.; $^1$H NMR (400 MHz, CDCl₃) δ 7.01 (d, J=0.5 Hz, 1H), 6.97 (d, J=0.8 Hz, 1H), 5.98 (s, 2H), 3.93 (s, 4H), 1.33 (s, 12H); EIMS m/z 278.

Preparation 49: 6-Bromo-4-fluorobenzo[d][1,3]dioxole-2-thione

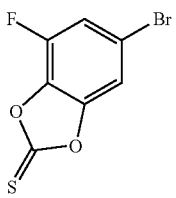

5-Bromo-3-fluorobenzene-1,2-diol (2.0 g, 9.7 mmol, prepared according to Lu, Hejun; Tang, Peng Cho; Chen, Yiqian; Wang, Shenglan; Wang, Hua; Zhang, Lei; Li, Jun, WO 2011140936 A1) was dissolved in chloroform (25 mL), treated with thiophosgene (1.2 g, 11 mmol) and cooled to 0-5° C. Sodium hydroxide (10% aqueous, 8.9 g, 22 mmol) was added dropwise with vigorous stirring over 30 min. After 1 h, the chloroform was removed under vacuum and the pH was adjusted to 2 by addition of 6 M HCl. The solid that was formed was taken up in ethyl acetate (120 mL), washed with saturated NaCl (30 mL), dried (Na₂SO₄) and evaporated. The material was purified by flash chromatography using a 0-30% ethyl acetate-hexane gradient to give the title compound as a tan solid (1.5 g, 62%): mp 41-42° C.; $^1$H NMR (400 MHz, CDCl₃) δ 7.35-7.30 (m, 1H), 7.29 (d, J=1.6 Hz, 1H); $^{19}$F NMR (376 MHz, CDCl₃) δ −128.93; EIMS m/z 248/250.

Preparation 50: 6-Bromo-2,2,4-trifluorobenzo[d][1,3]dioxole

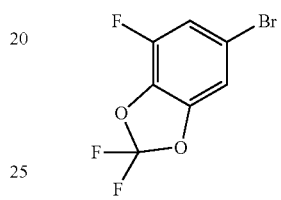

6-Bromo-4-fluorobenzo[d][1,3]dioxole-2-thione (6.9 g, 28 mmol) was dissolved in dry dichloromethane (150 mL), cooled to −40° C. and treated with pyridine hydrofluoride (70% HF by wt; 39 g, 273 mmol). N-Iodosuccinimide (19 g, 84 mmol) was added in portions while keeping the temperature below −30° C. The mixture was stirred for 30 min at −35 to −0° C. and then allowed to warm to 20° C. and stirred for 30 min. Applying external cooling to keep the temperature below 35° C., the mixture was treated in portions with a solution of NaHSO₃ (8 g) in water (50 mL) and stirred for 15 min. The mixture was treated with additional water (200 mL) to dissolve solids. The organic phase was washed with saturated NaCl (30 mL), and dried (Na₂SO₄). The bulk of the solvent was removed by atmospheric distillation through a 7 tray Oldershaw column, and when the pot volume was ca 50 mL, distillation was continued through a 200 mm Vigreux column until the head temperature reached 75° C. After cooling to ambient temperature, the pressure was reduced to 50 mmHg and the product was taken overhead at 75-80° C. through a simple distillation head to give the title compound as a pale pink liquid (5.3 g, 74%): $^1$H NMR (400 MHz, CDCl₃) δ 7.11 (dd, J=9.0, 1.7 Hz, 1H), 7.07 (m, 1H); $^{19}$F NMR (376 MHz, CDCl₃) δ −49.56, −132.65; EIMS m/z 254.

Preparation 51: 4,4,5,5-Tetramethyl-2-(2,2,7-trifluorobenzo[d][1,3]dioxol-5-yl)-1,3,2-dioxaborolane

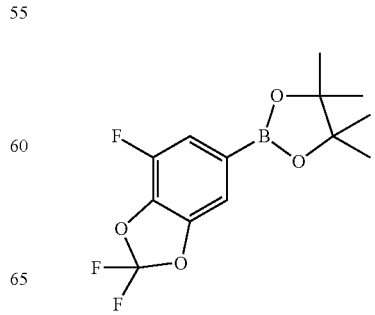

6-Bromo-2,2,4-trifluorobenzo[d][1,3]dioxole (2.0 g, 7.8 mmol) was dissolved in dry tetrahydrofuran (10 mL), cooled to −5 to 0° C. and treated in portions with isopropylmagnesium lithium chloride complex (1.3 M; 6.3 mL, 8.2 mmol). The cooling bath was removed and the mixture was stirred for 30 min. 2-Isopropoxy-4,4,5,5-tetramethyl-1,3,2-dioxaborolane (1.6 g, 8.4 mmol) was added, the mixture was stirred for 1 h and then treated with saturated NH$_4$Cl (5 mL). The mixture was diluted with ethyl acetate (40 mL) and saturated NaCl (10 mL) and the pH was adjusted to 2 by addition of HCl. The organic phase was washed with saturated NaCl (5 mL), dried (Na$_2$SO$_4$) and evaporated to give the title compound which was used without further purification (2 g, 85%): $^1$H NMR (400 MHz, CDCl$_3$) δ 7.36 (d, J=9.8 Hz, 1H), 7.29 (d, J=6.5 Hz, 1H), 1.33 (s, 12H); $^{19}$F NMR (376 MHz, CDCl$_3$) δ −49.79, −136.26; EIMS m/z 302.

Preparation 52: 3-Bromo-6-fluorobenzene-1,2-diol

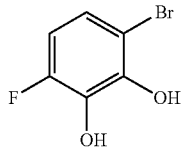

3-Bromo-6-fluoro-2-hydroxybenzaldehyde (9.0 g, 41 mmol, prepared according to Castro, Alfred C.; Depew, Kristopher M.; Grogan, Michael J.; Holson, Edward B.; Hopkins, Brian T.; Johannes, Charles W.; Keaney, Gregg F.; Koney, Nii O.; Liu, Tao; Mann, David A.; Nevalainen, Marta; Peluso, Stephane; Perez, Lawrence Blas; Snyder, Daniel A.; Tibbitts, Thomas T., WO 2008024337 A2) was stirred in 1.0 M NaOH (47 mL) and treated with hydrogen peroxide (6%; 49 g, 86 mmol). External cooling was applied to keep the temperature controlled below 50° C. After 2 h total stirring, the mixture was stirred with a solution of NaHSO$_3$ in 50 mL water and extracted with ethyl acetate (2×75 mL). The combined extracts were washed with saturated NaCl (20 mL), dried (Na$_2$SO$_4$) and evaporated. The catechol derivative, as a dark orange liquid, was carried to the next step without further purification (8.9 g, qt): EIMS m/z 206.

Preparation 53:
4-Bromo-7-fluorobenzo[d][1,3]dioxole-2-thione

3-Bromo-6-fluorobenzene-1,2-diol (8.9 g, 43 mmol) was dissolved in chloroform (100 mL), cooled to 0-5° C. and treated with thiophosgene (5.4 g, 47 mmol). Aqueous sodium hydroxide solution (10 wt %; 40 g, 99 mmol) was added in portions over 30 min with vigorous stirring. Stirring was continued for 60 min at 5-15° C. and then most of the chloroform was removed by rotary evaporation. The pH was adjusted to 2 by addition of 1 M HCl and the precipitated thione was taken up in ethyl acetate (150 mL). The organic phase was washed with water (25 mL), saturated NaCl (25 mL), dried (Na$_2$SO$_4$), and evaporated. The crude product was purified by flash chromatography, eluting with a 0-20% ethyl acetate-hexane gradient to give the title compound as a tan solid (6.2 g, 58%): mp 72-76° C.; 1H NMR (400 MHz, CDCl$_3$) δ 7.40 (dd, J=9.2, 4.1 Hz, 1H), 7.04 (t, J=9.1 Hz, 1H); $^{19}$F NMR (376 MHz, CDCl$_3$) δ −132.68; EIMS m/z 248.

Preparation 54:
4-Bromo-2,2,7-trifluorobenzo[d][1,3]dioxole

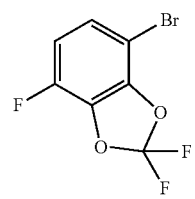 [SMILES: Fc1ccc(Br)c2c1OC(F)(F)O2]

4-Bromo-7-fluorobenzo[d][1,3]dioxole-2-thione (6.1 g, 25 mmol) was dissolved in dry dichloromethane (100 mL), cooled to −30 to −40° C. and treated with pyridine hydrofluoride (70 wt %; 35 g, 245 mmol). N-Iodosuccinimide was added in portions at −25 to −35° C. and the mixture was allowed to warm to 20° C. and stirred for 2 h. The dark mixture was cooled to 0° C. and treated with 15% NaHSO$_3$ solution (30 mL) with stirring. After 20 min, the mixture was diluted with dichloromethane (75 mL) and water (200 mL) to dissolve solids. The organic phase was washed with saturated NaCl (25 mL) and dried (Na$_2$SO$_4$). The solvent was removed by atmospheric distillation through a 450 mm Vigreux column. The product was brought over at 30-40 mmHg at 80-90° C. to give the title compound as a clear liquid (3.0 g, 47%): $^1$H NMR (400 MHz, CDCl$_3$) δ 7.18 (dd, J=9.3, 4.2 Hz, 1H), 6.85 (t, J=9.3 Hz, 1H); $^{19}$F NMR (376 MHz, CDCl$_3$) δ −49.08, −136.17; EIMS m/z 254.

Preparation 55: 4,4,5,5-Tetramethyl-2-(2,2,7-trifluorobenzo[d][1,3]dioxol-4-yl)-1,3,2-dioxaborolane

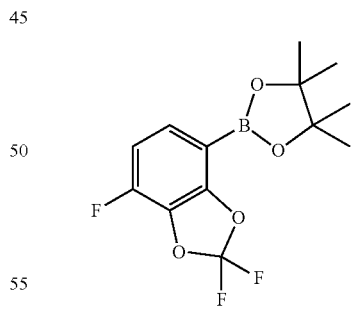

4-Bromo-2,2,7-trifluorobenzo[d][1,3]dioxole (2.0 g, 7.8 mmol) was dissolved in dry tetrahydrofuran (12 ml), cooled to −5° C. and treated in portions with isopropylmagnesium lithium chloride complex (1.3 M; 6.3 mL, 8.2 mmol). The mixture was stirred for 2 h at 5 to 15° C., treated with 2-isopropoxy-4,4,5,5-tetramethyl-1,3,2-dioxaborolane (1.6 g, 8.4 mmol) and stirred for 2 h at 10 to 20° C. The mixture was treated with saturated NH$_4$Cl (5 mL), stirred for 10 min and then shaken with 1 M HCl (10 mL) and ethyl acetate (75 mL). The organic phase was washed with saturated NaCl (10 mL), dried (Na₂SO₄) and evaporated to give the title compound as a white solid (2.3 g, 98%): ¹H NMR (400 MHz, CDCl₃) δ 7.41 (dd, J=8.7, 5.3 Hz, 1H), 6.88 (dd, J=9.5, 8.8 Hz, 1H), 1.36 (s, 12H); ¹⁹F NMR (376 MHz, CDCl₃) δ −49.07, −131.31; EIMS m/z 302.

Preparation 56: (2,2-Difluoro-7-(4,4,5,5-tetramethyl-1,3,2-dioxaborolan-2-yl)benzo[d][1,3]dioxol-4-yl)trimethylsilane

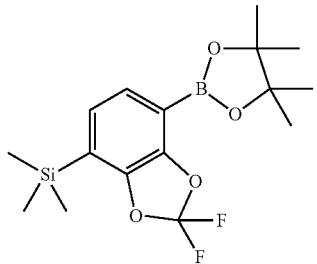

(2,2-Difluorobenzo[d][1,3]dioxol-4-yl)trimethylsilane (5.0 g, 22 mmol, prepared as described in Gorecka, Joanna; Leroux, Frederic; Schlosser, Manfred, *European Journal of Organic Chemistry* 2004, 1, 64-68) was added to a stirred solution of sec-BuLi (1.4 M; 10 mL, 14 mmol) in dry tetrahydrofuran (28 mL) cooled to −75° C. After 2 h at −75° C., 2-isopropoxy-4,4,5,5-tetramethyl-1,3,2-dioxaborolane (4.2 g, 23 mmol) was added, and the mixture was stirred for 90 min at −75° C. The mixture was treated with saturated NH₄Cl (5 mL) and warmed to 20° C. The mixture was combined with water (75 mL), acidified with 6 M HCl and extracted with diethyl ether (100 mL). The organic phase was washed with saturated NaCl (15 mL), dried (Na₂SO₄) and evaporated to give the title compound (estimated purity of 60%) which was used without further purification: ¹H NMR (400 MHz, CDCl₃) δ 7.39 (d, J=7.5 Hz, 1H), 7.07 (d, J=7.5 Hz, 1H), 1.36 (s, 12H), 0.33 (s, 9H); ¹⁹F NMR (376 MHz, CDCl₃) δ −49.33; EIMS m/z 356.

Preparation 57: 4-Bromo-5-fluorobenzene-1,2-diol

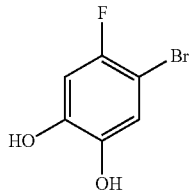

To CH₂Cl₂ (30 mL) in a 50 mL round bottom flask was added 4-bromo-5-fluoro-2-methoxyphenol (2 g, 9.05 mmol). The reaction mixture was cooled to 0° C. in an ice/water bath. Boron tribromide (1.027 mL, 10.86 mmol) was slowly added via syringe over 5 min, and the ice/water bath was removed. The reaction mixture was allowed to warm to room temperature and was stirred for 18 h. The reaction mixture was placed in an ice/water bath and methanol (30 mL) was slowly added via syringe. Upon removal of the ice/water bath, the reaction mixture was allowed to warm to room temperature. The reaction mixture was transferred to a separatory funnel, diluted with ethyl acetate (200 mL) and washed with water (200 mL). The organic layer was dried over Na₂SO₄ and filtered. Concentration of the organic solution gave 4-bromo-5-fluorobenzene-1,2-diol as a dark brown oil (1.8 g, 96%): ¹H NMR (400 MHz, CDCl₃) δ 7.03 (d, J=6.5 Hz, 1H), 6.72 (dd, J=8.3, 3.5 Hz, 1H); ¹⁹F NMR (376 MHz, CDCl₃) δ −115.91 (s); ESIMS m/z 207 ([M+H]⁺), 206 ([M−H]⁻).

Preparation 58: 5-Bromo-6-fluorobenzo[d][1,3]dioxole

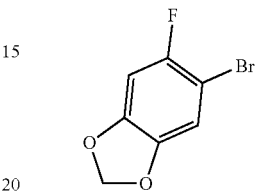

To N,N-dimethylformamide (25 mL) in a 50 mL flask was added 4-bromo-5-fluorobenzene-1,2-diol (2 g, 9.66 mmol), cesium carbonate (4.72 g, 14.49 mmol) and bromochloromethane (1.875 g, 14.49 mmol). The reaction mixture was allowed to stir at room temperature for 1 h and was then heated to an external temperature of 80° C. for 3 h. Upon cooling, the reaction mixture was diluted with Et₂O (75 mL) and washed with water (50 mL) followed by a wash with saturated NaCl solution (50 mL). The organic layer was dried over MgSO₄ and filtered. Concentration of the organic solution gave 5-bromo-6-fluorobenzo[d][1,3]dioxole as a light orange solid (1.8 g, 85%): ¹H NMR (400 MHz, CDCl₃) δ 6.94 (d, J=5.9 Hz, 1H), 6.67 (d, J=7.9 Hz, 1H), 6.00 (s, 2H); ¹⁹F NMR (376 MHz, CDCl₃) δ −113.82 (s); ESIMS m/z 220 ([M+H]⁺), 218 ([M−H]⁻).

Preparation 59: 5-Bromo-2,2-dimethylbenzo[d][1,3]dioxole

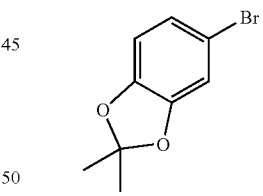

To benzene (50 mL) in a 250 mL round bottom flask was added 4-bromobenzene-1,2-diol (1 g, 5.29 mmol), 2,2-dimethoxypropane (2.204 g, 21.16 mmol), and p-toluene sulfonic acid monohydrate (0.050 g, 0.265 mmol). The flask was fitted with a Dean-Stark trap and heated to reflux for 18 h. Upon cooling, the reaction mixture was transferred to a separatory funnel and washed with 2 N NaOH solution (100 mL) and saturated NaCl solution (100 mL). The organic layer was dried with MgSO₄, filtered, and concentrated to yield 5-bromo-2,2-dimethylbenzo[d][1,3]dioxole as a dark brown oil (767 mg, 63%): ¹H NMR (400 MHz, CDCl₃) δ 6.91-6.85 (m, 2H), 6.62-6.57 (m, 1H), 1.66 (s, 6H); ¹³C NMR (101 MHz, CDCl₃) δ 146.81 (s), 144.25 (s), 123.64 (s), 121.02 (s), 112.05 (s), 109.40 (s), 108.46 (s), 25.83 (s); ESIMS m/z 230 ([M+H]⁺), 228 ([M−H]⁻).

Preparation 60: 2-(2,2-Dimethylbenzo[d][1,3]dioxol-5-yl)-4,4,5,5-tetramethyl-1,3,2-dioxaborolane

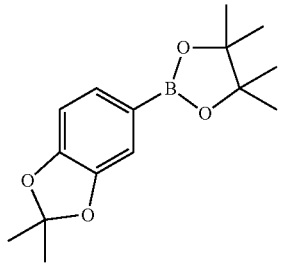

To DMSO (10 mL) was added potassium acetate (1.671 g, 17.03 mmol), 4,4,4',4',5,5,5',5'-octamethyl-2,2'-bi(1,3,2-dioxaborolane) (1.729 g, 6.81 mmol), 5-bromo-2,2-dimethylbenzo[d][1,3]dioxole (1.3 g, 5.68 mmol), and PdCl$_2$(dppf) (0.415 g, 0.568 mmol). The reaction was heated to an external temperature of 80° C. for 18 h. Upon cooling, the reaction mixture was poured into ice water (50 mL). The ice water mixture was transferred to a separatory funnel and two extractions with ethyl acetate (50 mL) were completed. The organic layers were combined, dried over Na$_2$SO$_4$, and filtered. The solution was concentrated onto 5 g of Celite® using ethyl acetate as solvent. The impregnated Celite was loaded onto a Teledyne Isco purification system and purified by silica gel chromatography using 0-30% ethyl acetate:hexanes to yield 2-(2,2-dimethylbenzo[d][1,3]dioxol-5-yl)-4,4,5,5-tetramethyl-1,3,2-dioxaborolane as a red semi-solid (767 mg, 49%): $^1$H NMR (400 MHz, CDCl$_3$) δ 7.31 (dt, J=6.6, 3.3 Hz, 1H), 7.15 (s, 1H), 6.74 (d, J=7.7 Hz, 1H), 1.66 (s, 6H), 1.32 (s, 12H); $^{13}$C NMR (101 MHz, CDCl$_3$) δ 129.21 (s), 113.78 (s), 108.15 (s), 83.59 (s), 25.86 (s), 24.82 (s); ESIMS m/z 277 ([M+H]$^+$), 275 ([M−H]$^−$).

Preparation 61: 2-(6-Fluorobenzo[d][1,3]dioxol-5-yl)-4,4,5,5-tetramethyl-1,3,2-dioxaborolane

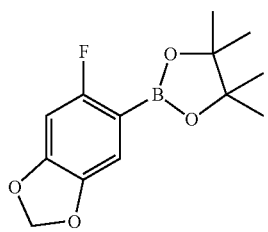 [SMILES: CC1(C)OB(c2cc3c(cc2F)OCO3)OC1(C)C]

2-(6-Fluorobenzo[d][1,3]dioxol-5-yl)-4,4,5,5-tetramethyl-1,3,2-dioxaborolane was prepared as described in Preparation 60 from 5-bromo-6-fluorobenzo[d][1,3]dioxole to afford a brown oil (74%): $^1$H NMR (400 MHz, CDCl$_3$) δ 7.08 (d, J=4.6 Hz, 1H), 6.55 (t, J=6.4 Hz, 1H), 5.97 (d, J=2.1 Hz, 2H), 1.24 (s, 12H); $^{13}$C NMR (101 MHz, CDCl$_3$) δ 131.70, 131.37, 128.34, 113.38, 101.93, 98.12, 97.80, 83.51, 24.80; ESIMS m/z 267 ([M+H]$^+$), 265 ([M−H]$^−$).

Preparation 62: 2-(2,2-Difluorobenzo[d][1,3]dioxol-5-yl)-4,4,5,5-tetramethyl-1,3,2-dioxaborolane

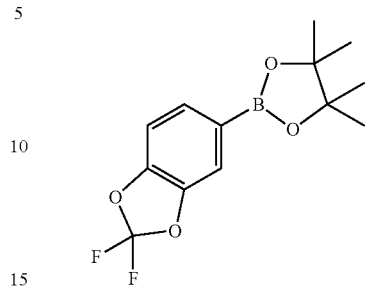

To an oven-dried three-necked round bottom flask under nitrogen was added 5-bromo-2,2-difluorobenzo[d][1,3]dioxole (2.516 g, 10.6 mmol) and anhydrous tetrahydrofuran (26 mL). The solution was cooled to 0° C. Isopropylmagnesium chloride-lithium chloride complex (1.3 M; 10 mL, 13.0 mmol) was added slowly and stirred for 1 h. 2-Isopropoxy-4,4,5,5-tetramethyl-1,3,2-dioxaborolane (2.2 mL, 10.62 mmol) was added, and the reaction mixture was stirred for 1 h. The reaction was quenched with saturated aqueous ammonium chloride and extracted three times with ethyl acetate. The combined organic layers were washed with brine and dried over anhydrous magnesium sulfate. The solution was filtered and concentrated to provide 2-(2,2-difluorobenzo[d][1,3]dioxol-5-yl)-4,4,5,5-tetramethyl-1,3,2-dioxaborolane as a yellow oil (2.54 g, 84%): $^1$H NMR (400 MHz, CDCl$_3$) δ 7.56 (dd, J=8.0, 1.0 Hz, 1H), 7.47 (d, J=0.6 Hz, 1H), 7.06 (dd, J=7.9, 0.4 Hz, 1H), 1.34 (s, 12H); $^{19}$F NMR (376 MHz, CDCl$_3$) δ −50.18; EIMS m/z 284.

Preparation 63: 2-(Benzo[d][1,3]dioxol-4-yl)-4,4,5,5-tetramethyl-1,3,2-dioxaborolane

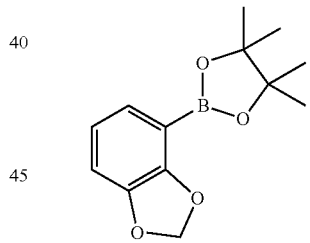

Benzo[d][1,3]dioxole (3.05 g, 25 mmol) was dissolved in tetrahydrofuran (50 mL) and cooled to −108° C. utilizing a tetrahydrofuran/liquid nitrogen bath. sec-Butyllithium (1.4 M in cyclohexane; 19.64 mL, 27.5 mmol) was added dropwise, keeping the temperature below −100° C. The reaction mixture was then stirred at temperatures between −100° C. and −108° C. for 2 h to ensure complete deprotonation. 2-Isopropoxy-4,4,5,5-tetramethyl-1,3,2-dioxaborolane (4.65 g, 25.00 mmol) was then added to the reaction mixture dropwise, keeping the temperature below −100° C. The reaction mixture was then allowed to warm to room temperature and partitioned between diethyl ether and water. The organic phase was extracted with water once again and the aqueous phases combined and acidified to pH 4 with HCl. The product was extracted with diethyl ether and the organic phase was dried and concentrated under vacuum. The product was purified by flash chromatography (silica gel) to provide the title compound as a white solid (2.14 g, 34.5%): $^1$H NMR (300 MHz, CDCl$_3$) δ 7.21 (dd, J=7.6, 1.4 Hz, 1H), 6.90 (dd, J=7.7, 1.5 Hz, 1H), 6.82 (t, J=7.6 Hz, 1H), 6.02 (s, 2H), 1.36 (s, 12H); EIMS m/z 248.

Preparation 64: 2-(2,2-Difluorobenzo[d][1,3]dioxol-4-yl)-4,4,5,5-tetramethyl-1,3,2-dioxaborolane

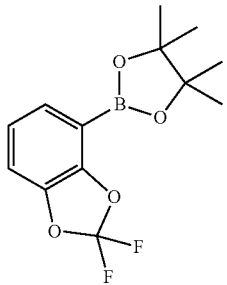 [SMILES: CC1(C)OB(c2cccc3c2OC(F)(F)O3)OC1(C)C]

2,2-Difluorobenzo[d][1,3]dioxole (6 g, 38.0 mmol) was dissolved in tetrahydrofuran (100 mL) and cooled to −75° C. sec-Butyllithium (1.4 M in cyclohexane; 29.8 mL, 41.7 mmol) was added dropwise, keeping the temperature below −65° C. The reaction mixture was then stirred at −75° C. for 1 h to ensure complete deprotonation. 2-Isopropoxy-4,4,5,5-tetramethyl-1,3,2-dioxaborolane (7.06 g, 38.0 mmol) was then added to the reaction mixture dropwise keeping the temperature below −65° C. The reaction mixture was then allowed to warm to room temperature and sit at room temperature for 2 h and was then partitioned between diethyl ether and water. The aqueous phase was acidified to pH 3 with 12 N HCl. The product was extracted with diethyl ether and the organic phase was dried and concentrated under vacuum to provide the title compound as an off-white solid (7.06 g, 65.5%): $^1$H NMR (300 MHz, CDCl$_3$) δ 7.43 (dd, J=7.5, 1.5 Hz, 1H), 7.13 (dd, J=7.9, 1.5 Hz, 1H), 7.05 (t, J=7.7 Hz, 1H), 1.37 (s, 12H); EIMS m/z 284.

Preparation 65: 4-Chloro-2,2-difluorobenzo[d][1,3]dioxole

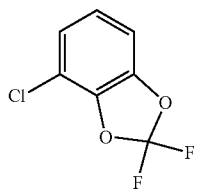 [SMILES: FC1(F)Oc2cccc(Cl)c2O1]

2,2-Difluorobenzo[d][1,3]dioxole (6.3 g, 39.8 mmol) was dissolved in tetrahydrofuran (66 mL) and cooled to −78° C. n-Butyllithium (2.5 M solution in hexanes; 16.74 mL, 41.8 mmol) was added dropwise, keeping the temperature below −70° C. The reaction mixture was then stirred at −78° C. for 1 h to ensure complete deprotonation. 1,2,2-Trifluorotrichloroethane (14.93 g, 80 mmol) was dissolved in tetrahydrofuran (33 mL) and cooled to −65° C. The lithiate was transferred via cannula into the solution of 1,2,2-trifluorotrichloroethane at a rate that allowed the temperature to remain between −60° C. and −65° C. during the addition. The reaction mixture was then allowed to warm to room temperature and partitioned between diethyl ether and water. The organic phase was concentrated and the product was flashed through 100 g of silica gel using hexane as a solvent to provide the title compound as a clear oil (5.74 g, 74.8%): $^1$H NMR (400 MHz, CDCl$_3$) δ 7.08 (dd, J=8.2, 1.4 Hz, 1H), 7.03 (t, J=8.0 Hz, 1H), 6.97 (dd, J=7.9, 1.5 Hz, 1H); EIMS m/z 192.

Preparation 66: 2-(7-Chloro-2,2-difluorobenzo[d][1,3]dioxol-4-yl)-4,4,5,5-tetramethyl-1,3,2-dioxaborolane

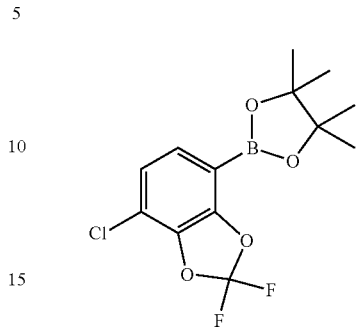

4-Chloro-2,2-difluorobenzo[d][1,3]dioxole (3 g, 15.58 mmol) was dissolved in tetrahydrofuran (50 mL) and cooled to −75° C. N-Butyllithium (2.5 M in hexanes; 6.86 mL, 17.14 mmol) was added dropwise keeping the temperature below −65° C. The reaction mixture was then stirred at −75° C. for 1 h to ensure complete deprotonation. 2-Isopropoxy-4,4,5,5-tetramethyl-1,3,2-dioxaborolane (3.19 g, 17.14 mmol) was then added to the reaction mixture dropwise keeping the temperature below −65° C. The reaction mixture was then allowed to warm to room temperature, added to diethyl ether (200 mL) and extracted with water (2×100 mL). The aqueous phases were combined and acidified to pH 4 with concentrated HCl. The product was extracted with diethyl ether and the organic phase was dried and concentrated under vacuum to provide the title compound as an off-white solid (3.82 g, 77%): $^1$H NMR (400 MHz, CDCl$_3$) δ 7.38 (d, J=8.4 Hz, 1H), 7.06 (d, J=8.4 Hz, 1H), 1.36 (s, 12H); EIMS m/z 318.

Preparation 67: 2-(2,2-Difluorobenzo[d][1,3]dioxol-5-yl)-4,4,5,5-tetramethyl-1,3,2-dioxaborolane

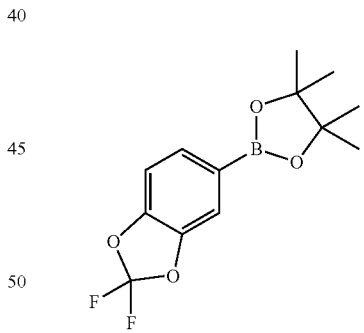

To a solution of 5-bromo-2,2-difluorobenzo[d][1,3]dioxole (1.5 g, 6.3 mmol) in N,N-dimethylformamide (12.7 mL) was added 4,4,4',4',5,5,5',5'-octamethyl-2,2'-bi(1,3,2-dioxaborolane) (1.6 g, 6.3 mmol), potassium acetate (1.9 g, 19.0 mmol), and (1,1'-bis(diphenylphosphino)ferrocene)-dichloropalladium(II) (0.3 g, 0.32 mmol). The reaction mixture was heated at 80° C. for 18 h, then the reaction mixture was diluted with Et$_2$O and washed with water. The organic layers were separated, dried with Na$_2$SO$_4$, filtered, concentrated in vacuo, and purified by silica gel chromatography eluting with 0-100% acetone in hexanes to yield a brown oil (0.9 g, 50%): $^1$H NMR (400 MHz, DMSO-d$_6$) δ 7.55 (d, J=8.0 Hz, 1H), 7.53 (s, 1H), 7.43 (d, J=8.0 Hz, 1H), 1.30 (s, 12H); $^{19}$F NMR (376 MHz, DMSO-d$_6$) δ −49.26 (s); EIMS m/z 284.

Synthesis of Compounds of Formula (I)

Example 1

Methyl 4-amino-3-chloro-6-(1,3-dihydroisobenzofuran-5-yl)-5-fluoropicolinate

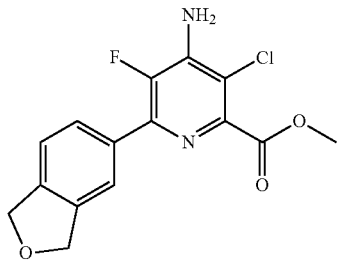 [SMILES: COC(=O)c1nc(-c2ccc3c(c2)COC3)c(F)c(N)c1Cl]

tert-Butyl nitrite (1.3 mL, 11 mmol, 1.5 equiv) was added to a stirred solution of benzoic peroxyanhydride (36 mg, 0.15 mmol, 0.02 equiv), diboron bis(pinoacol) ester (1.9 g, 7.4 mmol, 1.0 equiv), and 1,3-dihydroisobenzofuran-5-amine (1.0 g, 7.4 mmol, 1.0 equiv) in acetonitrile (25 mL) at 23° C. The resulting homogeneous orange/brown solution was stirred at 23° C. for 3 h. Activated charcoal was added and the black mixture was gravity filtered and concentrated by rotary evaporation to afford 1.9 g dark brown oil, which appeared to be consistent with 2-(1,3-dihydroisobenzofuran-5-yl)-4,4,5,5-tetramethyl-1,3,2-dioxaborolane of ~30% purity, by crude $^1$H NMR analysis.

To the crude 2-(1,3-dihydroisobenzofuran-5-yl)-4,4,5,5-tetramethyl-1,3,2-dioxaborolane (estimated to be 570 mg, 2.3 mmol, 1.1 equiv) was added methyl 4-amino-3,6-dichloro-5-fluoropicolinate (500 mg, 2.1 mmol, 1.0 equiv), dichloro[bis(triphenylphosphino)]-palladium(II) (150 mg, 0.21 mmol, 0.10 equiv), and sodium carbonate (240 mg, 2.3 mmol, 1.1 equiv) followed by a 1:1 mixture of water:acetonitrile (7.0 mL) at 23° C. The resulting dark orange/brown mixture was heated to 85° C. and stirred for 4 h. The cooled reaction mixture was diluted with water (150 mL) and extracted with dichloromethane (4×70 mL). The combined organic layers were dried (magnesium sulfate), gravity filtered, and concentrated by rotary evaporation. The residue was purified by reverse phase column chromatography (5% acetonitrile to 100% acetonitrile gradient) to yield the title compound as an orange powder (150 mg, 22%): mp 153-156° C.; IR (neat film) 3468 (m), 3334 (s), 3205 (m), 2952 (m), 2856 (m), 1735 (s), 1623 (s), 1579 (w) cm$^{-1}$; $^1$H NMR (400 MHz, CDCl$_3$) δ 7.81-7.86 (m, 2H), 7.33 (d, J=8 Hz, 1H), 5.16 (br d, J=4 Hz, 1H), 4.89 (br s, 2H), 3.97 (s, 3H); ESIMS m/z 323 [(M+H)$^+$].

Example 2 (Coupling 1)

Methyl 4-amino-6-(benzo[d][1,3]dioxol-4-yl)-3-chloro-5-fluoropicolinate

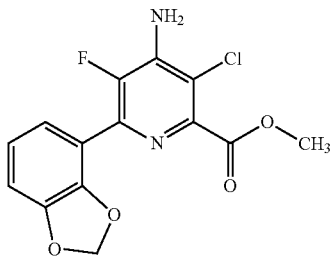 [SMILES: COC(=O)c1nc(-c2cccc3c2OCO3)c(F)c(N)c1Cl]

Methyl 4-amino-3,6-dichloro-5-fluoropicolinate (1.5 g, 6.28 mmol), 2-(benzo[d][1,3]dioxol-4-yl)-4,4,5,5-tetramethyl-1,3,2-dioxaborolane (2.024 g, 8.16 mmol), potassium fluoride (0.875 g, 15.06 mmol; Note: Related examples utilize cesium fluoride) and bis(triphenylphosphine)palladium (II)chloride (0.440 g, 0.628 mmol) were combined in acetonitrile (13 mL) and water (4.5 mL). The reaction mixture was then irradiated in a microwave at 110° C. in a capped vial for 20 min, with external IR-sensor temperature monitoring from the side of the vessel. The cooled reaction mixture was partitioned between ethyl acetate and water. The organic phase was dried and concentrated onto 1.2 g of silica gel. This mixture was applied to the top of a silica gel column and the product was eluted with a 7-60% hexane/ethyl acetate gradient solvent system to provide the title compound as a white solid (1.4 g, 68.7%): mp 146-148° C.; $^1$H NMR (400 MHz, CDCl$_3$) δ 7.16-7.09 (m, 1H), 6.98-6.85 (m, 2H), 6.01 (s, 2H), 4.91 (br s, 2H), 3.98 (s, 3H); ESIMS m/z 325 ([M+H]$^+$).

The preparation method used in this example is referred to in Table 2 as "Coupling 1".

Example 3 (Coupling 2)

Methyl 4-amino-3-chloro-6-(2,2,4-trifluorobenzo-[d][1,3]dioxol-5-yl)picolinate

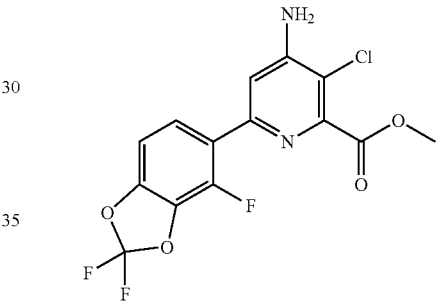

Methyl 4-acetamido-3,6-dichloropicolinate (600 mg, 2.3 mmol), cesium fluoride (690 mg, 4.5 mmol), 4,4,5,5-tetramethyl-2-(2,2,4-trifluorobenzo[d][1,3]dioxol-5-yl)-1,3,2-dioxaborolane (980 mg, 3.0 mmol) and bis(triphenylphosphine)palladium(II) chloride (110 mg, 0.16 mmol) were combined in 1:1 acetonitrile-water (6 mL) and heated at 115° C. for 30 min via microwave (Biotage Initiator), with external IR-sensor temperature monitoring from the side of the vessel. The mixture was shaken with water (10 mL) and ethyl acetate (25 mL). The organic phase was washed with saturated NaCl (5 mL), dried over Na$_2$SO$_4$ and evaporated. The residue was purified by chromatography on silica with 5-30% ethyl acetate-hexane to give a solid which was further purified by reverse-phase high-performance liquid chromatography eluting with 70/30/0.10 v/v/v acetonitrile/water/acetic acid to give 250 mg of the amide. This material was dissolved in methanol (10 mL), treated carefully with acetyl chloride (2 mL) and heated at reflux for 1 h. After cooling, the volatiles were removed under vacuum and the residue was stirred with ethyl acetate (15 mL) and saturated NaHCO$_3$ (5 mL) solution for 15 min. The organic phase was washed with saturated NaCl solution (5 mL), dried over Na$_2$SO$_4$ and evaporated under vacuum to give the title compound as a white solid (195 mg, 24%): mp 153-155° C.; $^1$H NMR (400 MHz, CDCl$_3$) δ 7.77 (dd, J=8.6, 7.1 Hz, 1H), 7.14 (d, J=1.9 Hz, 1H), 6.97 (dd, J=8.6, 0.9 Hz, 1H), 4.87 (s, 2H), 4.00 (s, 3H); $^{19}$F NMR (376 MHz, CDCl$_3$) δ −49.37 (s), −138.91 (s); ESIMS m/z 361 ([M+H]$^+$), 359 ([M−H]$^-$).

The preparation method used in this example is referred to in Table 2 as "Coupling 2".

Example 4 (Coupling 3)

Methyl 4-amino-3-chloro-6-(2,3-dihydrobenzofuran-6-yl)-5-fluoropicolinate

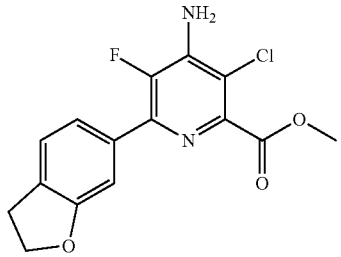 [SMILES: COC(=O)c1nc(-c2ccc3c(c2)OCC3)c(F)c(N)c1Cl]

3,3',3''-Phosphinetriyltribenzenesulfonate (0.209 g, 0.418 mmol), potassium fluoride (0.365 g, 6.28 mmol), methyl 4-amino-3-chloro-6-(2,3-dihydrobenzofuran-6-yl)-5-fluoropicolinate, diacetoxypalladium (0.047 g, 0.209 mmol), and 2-(2,3-dihydrobenzofuran-6-yl)-4,4,5,5-tetramethyl-1,3,2-dioxaborolane (0.541 g, 2.196 mmol) were combined in a 5-mL microwave vial. Water (Ratio: 3.00, Volume: 3 mL) and acetonitrile (Ratio: 1.000, Volume: 1 mL) were combined and then added to the microwave vial. The reaction vial was capped and placed on a Biotage Initiator microwave reactor for 6 min at 150° C., with external IR-sensor temperature monitoring from the side of the vessel. Upon cooling, the product precipitated as a solid. Additional material was present in the acetonitrile mixture. The solids were washed with water and dried to yield methyl 4-amino-3-chloro-6-(2,3-dihydrobenzofuran-6-yl)-5-fluoropicolinate as a white solid (250 mg, 37%): mp 150-154° C.; $^1$H NMR (400 MHz, CDCl$_3$) δ 7.42 (dt, J=7.7, 1.6 Hz, 1H), 7.33 (s, 1H), 7.28 (s, 1H), 4.88 (s, 2H), 4.62 (q, J=8.4 Hz, 2H), 3.98 (d, J=3.0 Hz, 3H), 3.31-3.18 (m, 2H); $^{13}$C NMR (101 MHz, CDCl$_3$) δ 164.99, 160.32, 147.23, 144.65, 140.38, 140.24, 134.32, 134.26, 128.69, 124.76, 121.43, 121.37, 114.64, 109.71, 109.65, 71.39, 52.90, 29.69; ESIMS m/z 233 ([M+H]$^+$), 231 ([M−H]$^−$).

The preparation method used in this example is referred to in Table 2 as "Coupling 3".

Example 5 (Coupling 4)

Methyl 4-amino-3-chloro-6-(2,2,5-trifluorobenzo[d][1,3]dioxol-4-yl)picolinate

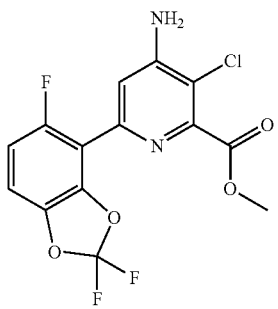 [SMILES: COC(=O)c1nc(-c2c(F)ccc3c2OC(F)(F)O3)cc(N)c1Cl]

Methyl 4-acetamido-3-chloro-6-(trimethylstannyl)picolinate (710 mg, 1.8 mmol) and 2,2,5-trifluoro-4-iodobenzo[d][1,3]dioxole (500 mg, 1.7 mmol) were combined in dry N,N-dimethylformamide (7 mL) and deaereated with a stream of nitrogen for 25 min. Bis(triphenylphosphine)-palladium(II) chloride (120 mg, 0.17 mmol) and cuprous iodide (32 mg, 0.17 mmol) were added and the mixture was heated to 80° C. for 5 h. The mixture was combined with ethyl acetate (30 mL) and water (15 mL) and the separated organic phase was washed with water (10 mL), saturated NaCl (10 mL), dried and evaporated. The residue was purified by chromatography on silica with 0-50% ethyl acetate-hexane gradient to give 115 mg of the amide intermediate. This material was dissolved in methanol (25 mL), treated with acetyl chloride (3-4 mL) and heated to 60° C. for 2 h. The volatiles were removed under vacuum and the residue was stirred with saturated NaHCO$_3$ (10 mL) and ethyl acetate (20 mL) for 30 min. The organic phase was separated, washed with saturated NaCl (5 mL), dried (Na$_2$SO$_4$), evaporated to give the title compound as a white solid (130 mg, 20%): $^1$H NMR (400 MHz, DMSO-d$_6$) δ 7.52 (dd, J=8.9, 4.0 Hz, 1H), 7.22 (dd, J=11.0, 9.0 Hz, 1H), 7.06 (d, J=1.4 Hz, 1H), 6.99 (s, 2H), 3.88 (s, 3H); $^{19}$F NMR (376 MHz, DMSO-d$_6$) δ −48.09, −121.60; ESIMS m/z 361 ([M+H]$^+$), 359 ([M−H]$^−$).

The preparation method used in this example is referred to in Table 2 as "Coupling 4".

Example 6 (Coupling 5)

Methyl 4-amino-5-fluoro-3-methoxy-6-(2,2,6-trifluorobenzo[d][1,3]dioxol-5-yl)picolinate

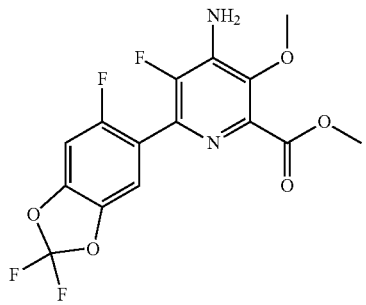 [SMILES: COC(=O)c1nc(-c2cc3c(cc2F)OC(F)(F)O3)c(F)c(N)c1OC]

To a mixture of methyl 4-amino-6-chloro-5-fluoro-3-methoxypicolinate (300 mg, 1.279 mmol) in acetonitrile (1 mL) and water (3 mL) was added potassium fluoride (149 mg, 2.56 mmol), palladium(II) acetate (28.7 mg, 0.128 mmol) and tris(3-sulfonatophenyl)phosphine tetrahydrate, sodium salt (150 mg, 0.256 mmol). The reaction mixture was then heated at 120° C. for 20 min in a microwave reactor. The cooled reaction mixture was then diluted with dichloromethane and washed with water. The phases were separated and the organics were concentrated. The residue was purified by reverse phase chromatography (100 g C18) eluted with 50/50 acetonitrile-water (0.1% trifluoroacetic acid) to provide the title compound as an off-white solid (251 mg, 52.5%).

The preparation method used in this example is referred to in Table 2 as "Coupling 5".

Example 7

Methyl 4-amino-6-(7-bromo-2,2-difluorobenzo[d][1,3]dioxol-4-yl)-3-chloro-5-fluoropicolinate

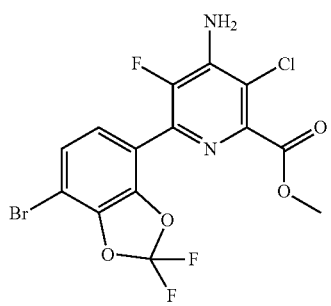 [SMILES: COC(=O)c1nc(-c2ccc(Br)c3c2OC(F)(F)O3)c(F)c(N)c1Cl]

Methyl 4-amino-3-chloro-6-(2,2-difluoro-7-(trimethylsilyl)benzo[d][1,3]dioxol-4-yl)-5-fluoropicolinate (400 mg, 0.92 mmol) was stirred in 1,2-dichloroethane (5 mL), treated with bromine (1.0 g, 6.5 mmol) and stirred at 20-25° C. for 4 h. The solution was stirred with 10% NaHSO₃ solution (30 mL) and extracted with ethyl acetate (35 mL). The organic phase was washed with saturated NaCl (5 mL), dried (Na₂SO₄) and evaporated to give the title compound as a white solid (370 mg, 92%): mp 168-170° C.; $^1$H NMR (400 MHz, CDCl₃) δ 7.35 (m, 1H), 5.02 (s, 1H), 3.99 (s, 3H); $^{19}$F NMR (376 MHz, CDCl₃) δ −49.23, −137.58; ESIMS m/z 439 ([M+H]⁺), 437 ([M−H]⁻).

Example 8

Methyl 4-amino-3-chloro-6-(2,2-difluoro-7-iodo-benzo-[d][1,3]dioxol-4-yl)-5-fluoropicolinate

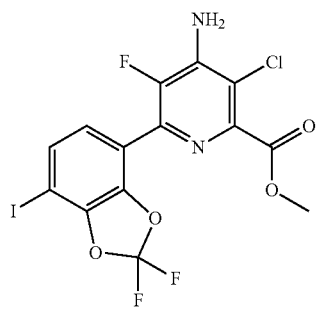 [SMILES: COC(=O)c1nc(-c2ccc(I)c3c2OC(F)(F)O3)c(F)c(N)c1Cl]

Methyl 4-amino-3-chloro-6-(2,2-difluoro-7-(trimethylsilyl)benzo[d][1,3]dioxol-4-yl)-5-fluoropicolinate (400 mg, 0.92 mmol) in 1,2-dichloroethane (5 mL) was treated with iodine monochloride (900 mg, 5.5 mmol) and stirred for 20 h at 20° C. The mixture was combined with 10 wt % NaHSO₃ solution (30 mL) and ethyl acetate (30 mL). The aqueous phase was extracted with ethyl acetate (15 mL), and the combined organic phases were washed with saturated NaCl (10 mL), dried (Na₂SO₄) and evaporated to give the title compound as a white solid (430 mg, 96%): mp 156-159° C.; $^1$H NMR (400 MHz, CDCl₃) δ 7.50 (d, J=8.6 Hz, 1H), 7.23 (d, J=8.6 Hz, 1H), 5.02 (s, 2H), 3.99 (s, 3H); $^{19}$F NMR (376 MHz, CDCl₃) δ −49.22, −137.49; ESIMS m/z 487 ([M+H]⁺), 485 ([M−H]⁻).

Example 9 (Hydrolysis)

4-Amino-6-(benzo[d][1,3]dioxol-4-yl)-3-chloro-5-fluoropicolinic acid

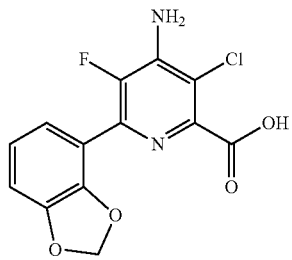 [SMILES: Nc1c(F)c(-c2cccc3c2OCO3)nc(C(=O)O)c1Cl]

To a reaction vessel containing methyl 4-amino-6-(benzo[d][1,3]dioxol-4-yl)-3-chloro-5-fluoropicolinate (0.150 g, 0.462 mmol) was added methanol (9.24 mL) and 2 N sodium hydroxide (0.924 mL, 1.848 mmol). The reaction mixture was stirred overnight at room temperature, neutralized to pH 3 with 2 N HCl, and concentrated under a stream of nitrogen. The precipitate that formed was filtered off, washed with water, and dried to provide the title compound as a white solid (0.107 g, 74.6%): mp 171-173° C.; $^1$H NMR (400 MHz, DMSO-d₆) δ 7.08-7.00 (m, 2H), 6.99-6.93 (m, 2H), 6.93 (br s, 2H), 6.06 (s, 2H); ESIMS m/z 311.2 ([M+H]⁺), 309.1 ([M−H]⁻).

The preparation method used in this example is referred to in Table 2 as "Hydrolysis"

TABLE 2

Compound Number, Structure, Preparation and Appearance

| C. No. | Structure | Appearance | Prepared as described in Example: | Precursor(s) |
|---|---|---|---|---|
| 1 | 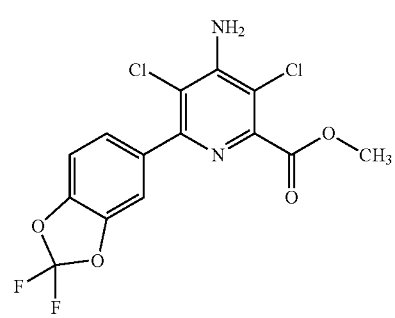 [SMILES: COC(=O)c1nc(-c2ccc3c(c2)OC(F)(F)O3)c(Cl)c(N)c1Cl] | Off-White Solid | Coupling 1 | Head H; 2-(2,2-difluorobenzo[d][1,3]dioxol-5-yl)-4,4,5,5-tetramethyl-1,3,2-dioxaborolane |

TABLE 2-continued

Compound Number, Structure, Preparation and Appearance

| C. No. | Structure | Appearance | Prepared as described in Example: | Precursor(s) |
|---|---|---|---|---|
| 2 | 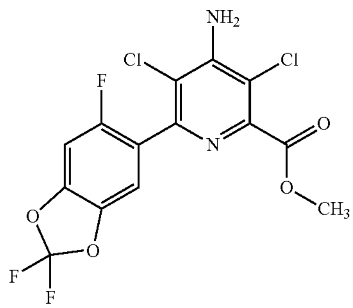 [SMILES: COC(=O)c1nc(-c2cc3c(cc2F)OC(F)(F)O3)c(Cl)c(N)c1Cl] | White Solid | Coupling 1 | Head H; 4,4,5,5-tetramethyl-2-(2,2,6-trifluoro-1,3-benzodioxol-5-yl)-1,3,2-dioxaborolane |
| 3 | 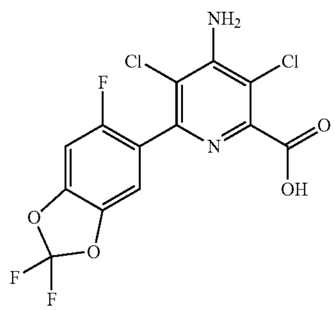 [SMILES: Nc1c(Cl)c(C(=O)O)nc(-c2cc3c(cc2F)OC(F)(F)O3)c1Cl] | Gum | Hydrolysis | Compound 2 |
| 4 | 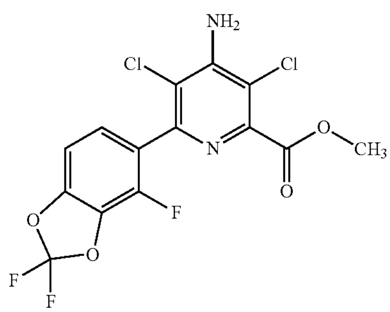 [SMILES: COC(=O)c1nc(-c2ccc3c(c2F)OC(F)(F)O3)c(Cl)c(N)c1Cl] | White Solid | Coupling 1 | Head H; 4,4,5,5-tetramethyl-2-(2,2,4-trifluorobenzo[d][1,3]dioxol-5-yl)-1,3,2-dioxaborolane |
| 5 | 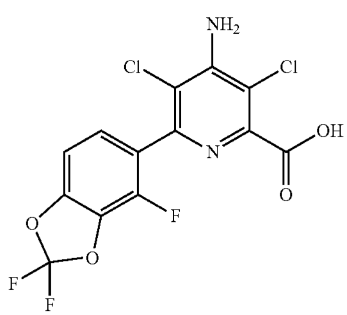 [SMILES: Nc1c(Cl)c(C(=O)O)nc(-c2ccc3c(c2F)OC(F)(F)O3)c1Cl] | White Solid | Hydrolysis | Compound 4 |
| 6 | 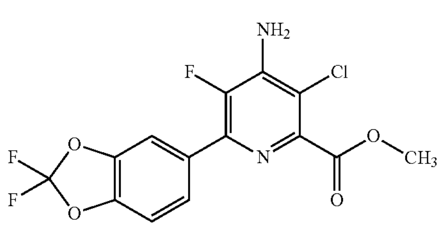 [SMILES: COC(=O)c1nc(-c2ccc3c(c2)OC(F)(F)O3)c(F)c(N)c1Cl] | White Solid | Coupling 1 | Head B; (2,2-difluorobenzo[d][1,3]dioxol-5-yl)boronic acid |

TABLE 2-continued

Compound Number, Structure, Preparation and Appearance

| C. No. | Structure | Appearance | Prepared as described in Example: | Precursor(s) |
|---|---|---|---|---|
| 7 | 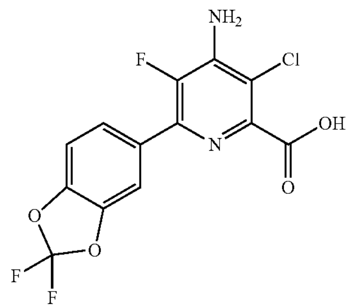 [SMILES: Nc1c(F)c(-c2ccc3c(c2)OC(F)(F)O3)nc(C(=O)O)c1Cl] | White Solid | Hydrolysis | Compound 6 |
| 8 | 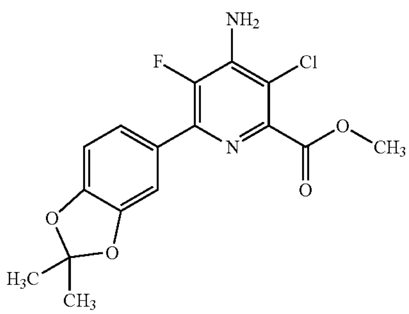 | Yellow Semi-Solid | Coupling 3 | Head B; 2-(2,2-dimethylbenzo[d]3[1,]dioxol-5-yl)-4,4,5,5-tetramethyl-1,3,2-dioxaborolane |
| 9 | 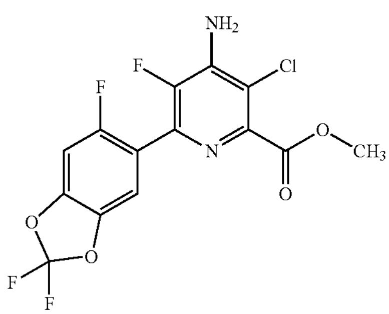 [SMILES: COC(=O)c1nc(-c2cc3c(cc2F)OC(F)(F)O3)c(F)c(N)c1Cl] | White Solid | Coupling 1 | Head B; 4,4,5,5-tetramethyl-2-(2,2,6-trifluorobenzo[d][1,3]dioxol-5-yl)-1,3,2-dioxaborolane |
| 10 | 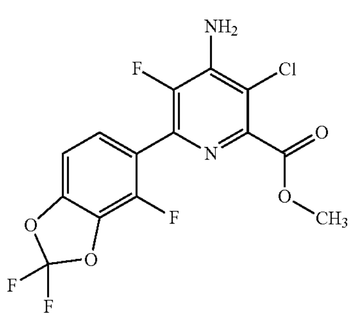 [SMILES: COC(=O)c1nc(-c2ccc3c(c2F)OC(F)(F)O3)c(F)c(N)c1Cl] | White Solid | Coupling 1 | Head B; 4,4,5,5-tetramethyl-2-(2,2,4-trifluoro-1,3-benzodioxol-5-yl)-1,3,2-dioxaborolane |

TABLE 2-continued

Compound Number, Structure, Preparation and Appearance

| C. No. | Structure | Appearance | Prepared as described in Example: | Precursor(s) |
|---|---|---|---|---|
| 11 | 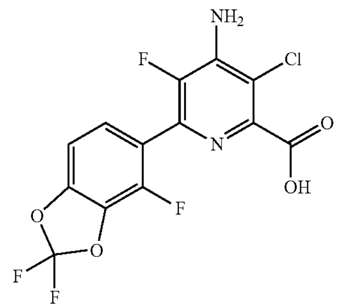 [SMILES: Nc1c(F)c(-c2ccc3c(c2F)OC(F)(F)O3)nc(C(=O)O)c1Cl] | White Solid | Hydrolysis | Compound 10 |
| 12 | 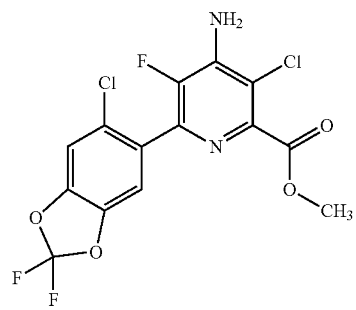 [SMILES: COC(=O)c1nc(-c2cc3c(cc2Cl)OC(F)(F)O3)c(F)c(N)c1Cl] | White Solid | Coupling 1 | Head B; 2-(6-chloro-2,2-difluoro-1,3-benzodioxol-5-yl)-4,4,5,5-tetramethyl-1,3,2-dioxaborolane |
| 13 | 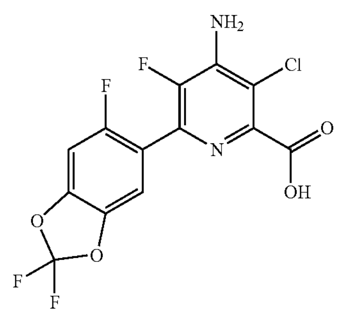 [SMILES: Nc1c(F)c(-c2cc3c(cc2F)OC(F)(F)O3)nc(C(=O)O)c1Cl] | White Solid | Hydrolysis | Compound 9 |
| 14 | 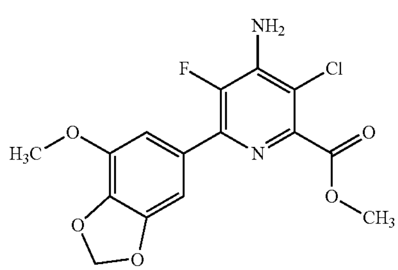 | White Solid | Coupling 1 | Head B; 2-(7-methoxy-1,3-benzodioxol-5-yl)-4,4,5,5-tetramethyl-1,3,2-dioxaborolane |
| 15 | 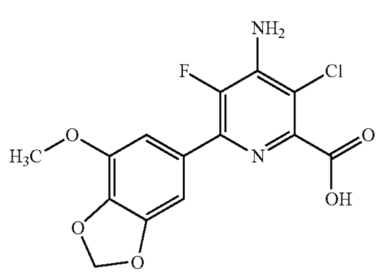 [SMILES: COc1cc(-c2nc(C(=O)O)c(Cl)c(N)c2F)cc2c1OCO2] | White Solid | Hydrolysis | Compound 14 |

TABLE 2-continued

Compound Number, Structure, Preparation and Appearance

| C. No. | Structure | Appearance | Prepared as described in Example: | Precursor(s) |
|---|---|---|---|---|
| 16 | 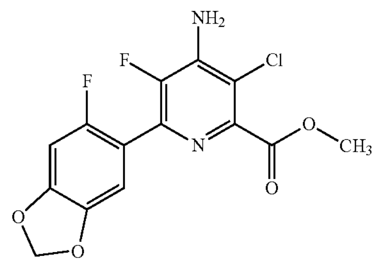 [SMILES: COC(=O)c1nc(-c2cc3c(cc2F)OCO3)c(F)c(N)c1Cl] | Tan Solid | Coupling 3 | Head B; 2-(6-fluorobenzo[d][1,3]dioxol-5-yl)-4,4,5,5-tetramethyl-1,3,2-dioxaborolane |
| 17 | 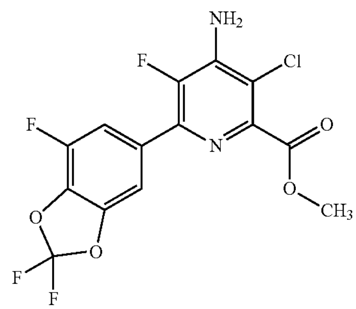 [SMILES: COC(=O)c1nc(-c2cc(F)c3c(c2)OC(F)(F)O3)c(F)c(N)c1Cl] | White Solid | Coupling 1 | Head B; 4,4,5,5-tetramethyl-2-(2,2,7-trifluoro-1,3-benzodioxol-5-yl)-1,3,2-dioxaborolane |
| 18 | 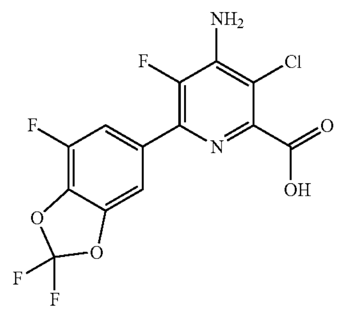 [SMILES: Nc1c(F)c(-c2cc(F)c3c(c2)OC(F)(F)O3)nc(C(=O)O)c1Cl] | White Solid | Hydrolysis | Compound 17 |
| 19 | 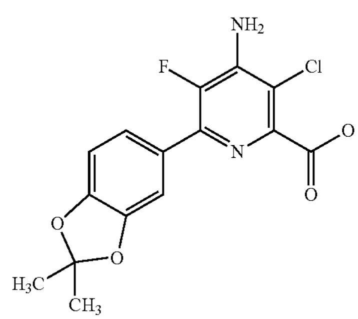 [SMILES: CC1(C)Oc2ccc(-c3nc(C(=O)O)c(Cl)c(N)c3F)cc2O1] | Brown Solid | Hydrolysis | Compound 8 |
| 20 | 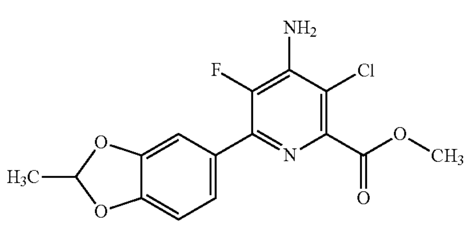 | White Solid | Coupling 1 | Head B; 4,4,5,5-tetramethyl-2-(2-methylbenzo[d][1,3]dioxol-5-yl)-1,3,2-dioxaborolane |

TABLE 2-continued

Compound Number, Structure, Preparation and Appearance

| C. No. | Structure | Appearance | Prepared as described in Example: | Precursor(s) |
|---|---|---|---|---|
| 21 | 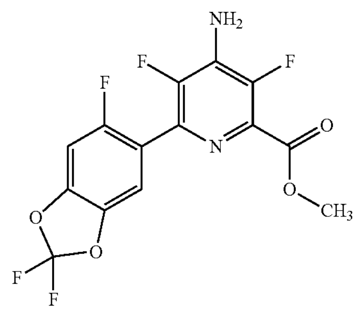 [SMILES: COC(=O)c1nc(-c2cc3c(cc2F)OC(F)(F)O3)c(F)c(N)c1F] | White Solid | Coupling 1 | Head O; 4,4,5,5-tetramethyl-2-(2,2,6-trifluorobenzo[d][1,3]dioxol-5-yl)-1,3,2-dioxaborolane |
| 22 | 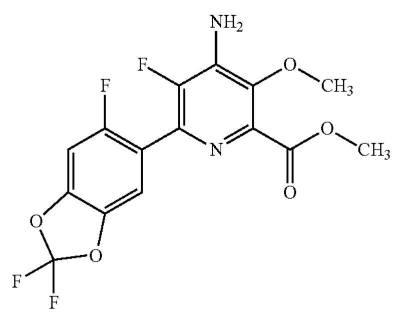 [SMILES: COC(=O)c1nc(-c2cc3c(cc2F)OC(F)(F)O3)c(F)c(N)c1OC] | Tan Solid | Coupling 5 | Head F; 4,4,5,5-tetramethyl-2-(2,2,6-trifluorobenzo[d]3[1,]dioxol-5-yl)-1,3,2-dioxaborolane |
| 23 | 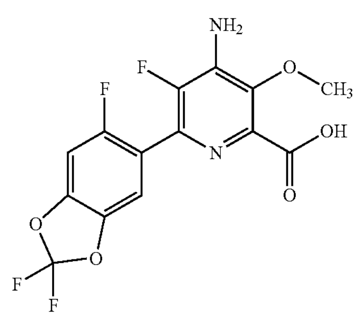 [SMILES: COc1c(C(=O)O)nc(-c2cc3c(cc2F)OC(F)(F)O3)c(F)c1N] | Tan Solid | Hydrolysis | Compound 22 |
| 24 | 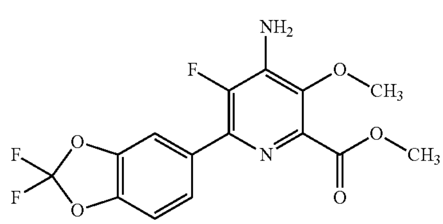 [SMILES: COC(=O)c1nc(-c2ccc3c(c2)OC(F)(F)O3)c(F)c(N)c1OC] | Off-White Solid | Coupling 1 | Head F; 2-(2,2-difluorobenzo[d][1,3]dioxol-5-yl)-4,4,5,5-tetramethyl-1,3,2-dioxaborolane |
| 25 | 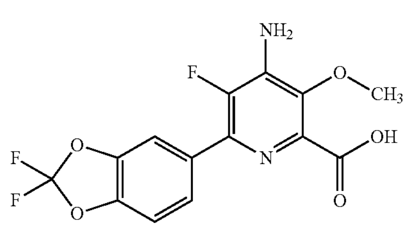 [SMILES: COc1c(C(=O)O)nc(-c2ccc3c(c2)OC(F)(F)O3)c(F)c1N] | Tan Solid | Hydrolysis | Compound 24 |

TABLE 2-continued

Compound Number, Structure, Preparation and Appearance

| C. No. | Structure | Appearance | Prepared as described in Example: | Precursor(s) |
|---|---|---|---|---|
| 26 | 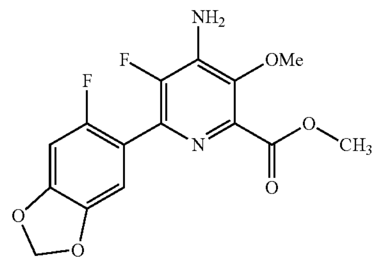 [SMILES: COC(=O)c1nc(-c2cc3c(cc2F)OCO3)c(F)c(N)c1OC] | Tan Solid | Coupling 3 | Head F; 2-(6-fluorobenzo[d][1,3]dioxol-5-yl)-4,4,5,5-tetramethyl-1,3,2-dioxaborolane |
| 27 | 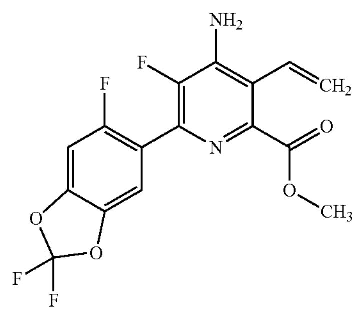 [SMILES: C=Cc1c(C(=O)OC)nc(-c2cc3c(cc2F)OC(F)(F)O3)c(F)c1N] | Tan Solid | Coupling 1 | Head G; 4,4,5,5-tetramethyl-2-(2,2,6-trifluoro-1,3-benzodioxol-5-yl)-1,3,2-dioxaborolane |
| 28 | 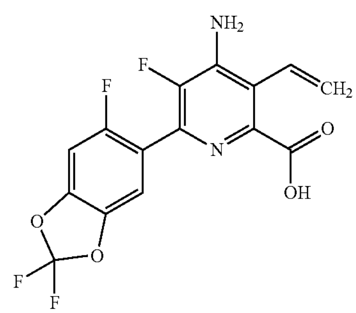 [SMILES: C=Cc1c(C(=O)O)nc(-c2cc3c(cc2F)OC(F)(F)O3)c(F)c1N] | White Solid | Hydrolysis | Compound 27 |
| 29 | 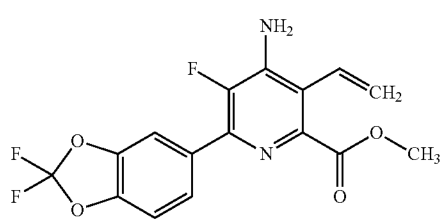 [SMILES: C=Cc1c(C(=O)OC)nc(-c2ccc3c(c2)OC(F)(F)O3)c(F)c1N] | Off-White Solid | Coupling 1 | Head G; 2-(2,2-difluorobenzo[d][1,3]dioxol-5-yl)-4,4,5,5-tetramethyl-1,3,2-dioxaborolane |
| 30 | 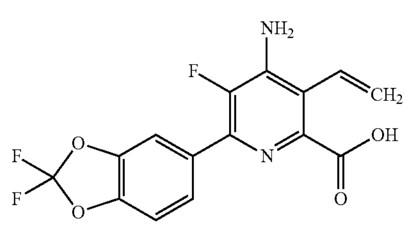 [SMILES: C=Cc1c(C(=O)O)nc(-c2ccc3c(c2)OC(F)(F)O3)c(F)c1N] | Brown Solid | Hydrolysis | Compound 29 |

TABLE 2-continued

Compound Number, Structure, Preparation and Appearance

| C. No. | Structure | Appearance | Prepared as described in Example: | Precursor(s) |
|---|---|---|---|---|
| 31 | 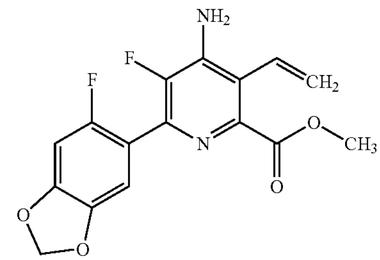 [SMILES: C=Cc1c(C(=O)OC)nc(-c2cc3c(cc2F)OCO3)c(F)c1N] | Tan Solid | Coupling 3 | Head G; 2-(6-fluorobenzo[d][1,3]dioxol-5-yl)-4,4,5,5-tetramethyl-1,3,2-dioxaborolane |
| 32 | 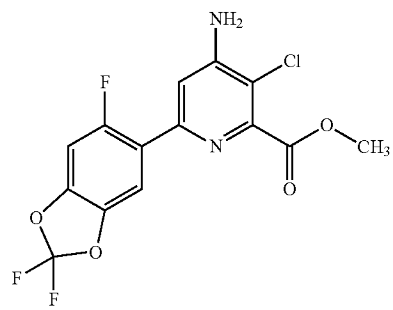 [SMILES: COC(=O)c1nc(-c2cc3c(cc2F)OC(F)(F)O3)cc(N)c1Cl] | Orange Solid | Coupling 1 | Head L; 4,4,5,5-tetramethyl-2-(2,2,6-trifluorobenzo[d][1,3]dioxol-5-yl)-1,3,2-dioxaborolane |
| 33 | 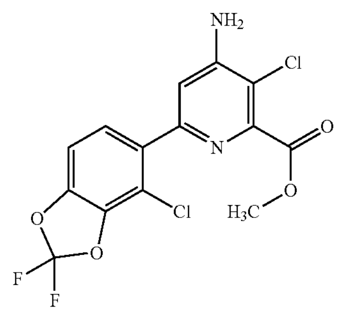 [SMILES: COC(=O)c1nc(-c2ccc3c(c2Cl)OC(F)(F)O3)cc(N)c1Cl] | White Solid | Coupling 1 | Head M; 2-(4-chloro-2,2-difluorobenzo[d][1,3]dioxol-5-yl)-4,4,5,5-tetramethyl-1,3,2-dioxaborolane |
| 34 | 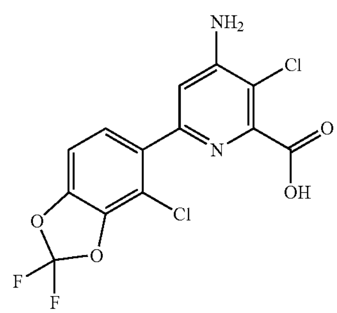 [SMILES: Nc1cc(-c2ccc3c(c2Cl)OC(F)(F)O3)nc(C(=O)O)c1Cl] | White Solid | Hydrolysis | Compound 33 |
| 35 | 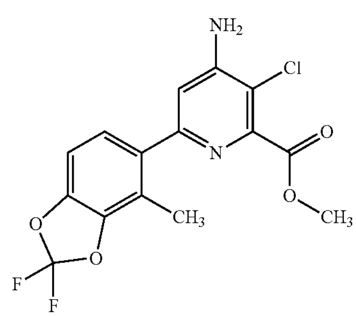 [SMILES: COC(=O)c1nc(-c2ccc3c(c2C)OC(F)(F)O3)cc(N)c1Cl] | White Solid | Coupling 1 | Head M; 2-(2,2-difluoro-4-methyl-1,3-benzodioxol-5-yl)-5,5-dimethyl-1,3,2-dioxaborinane |

TABLE 2-continued

Compound Number, Structure, Preparation and Appearance

| C. No. | Structure | Appearance | Prepared as described in Example: | Precursor(s) |
|---|---|---|---|---|
| 36 | 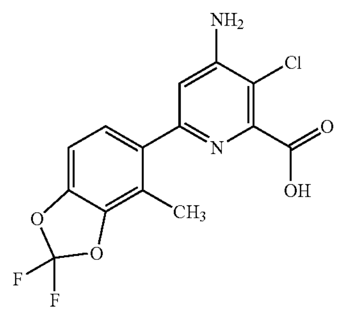 [SMILES: Cc1c(-c2cc(N)c(Cl)c(C(=O)O)n2)ccc2c1OC(F)(F)O2] | White Solid | Hydrolysis | Compound 35 |
| 37 | 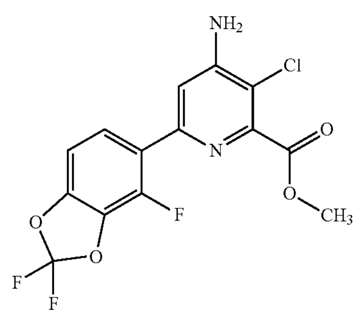 [SMILES: COC(=O)c1nc(-c2ccc3c(c2F)OC(F)(F)O3)cc(N)c1Cl] | White Solid | Coupling 2 | As described |
| 38 | 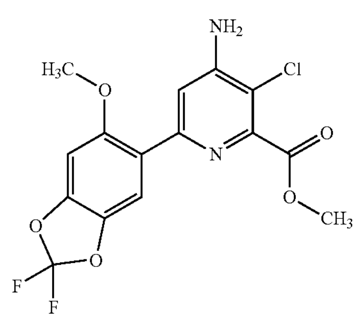 [SMILES: COC(=O)c1nc(-c2cc3c(cc2OC)OC(F)(F)O3)cc(N)c1Cl] | White Solid | Coupling 1 | Head A; 2-(2,2-difluoro-6-methoxy-1,3-benzodioxol-5-yl)-4,4,5,5-tetramethyl-1,3,2-dioxaborolane |
| 39 | 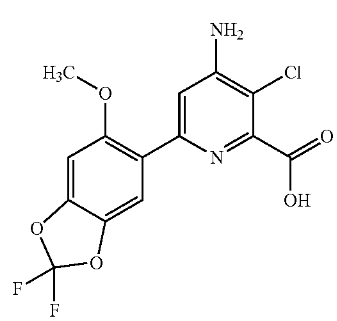 [SMILES: COc1cc2c(cc1-c1cc(N)c(Cl)c(C(=O)O)n1)OC(F)(F)O2] | White Solid | Hydrolysis | Compound 38 |

TABLE 2-continued

Compound Number, Structure, Preparation and Appearance

| C. No. | Structure | Appearance | Prepared as described in Example: | Precursor(s) |
|---|---|---|---|---|
| 40 | 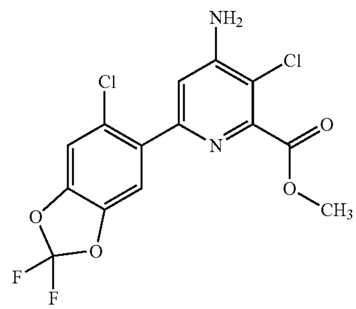 [SMILES: COC(=O)c1nc(-c2cc3c(cc2Cl)OC(F)(F)O3)cc(N)c1Cl] | White Solid | Coupling 1 | Head A; 2-(6-chloro-2,2-difluoro-1,3-benzodioxol-5-yl)-4,4,5,5-tetramethyl-1,3,2-dioxaborolane |
| 41 | 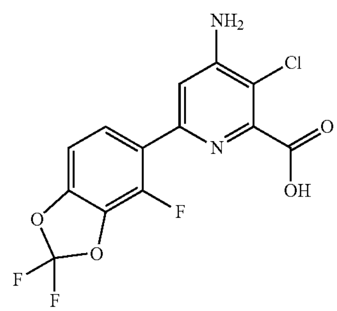 [SMILES: Nc1cc(-c2ccc3c(c2F)OC(F)(F)O3)nc(C(=O)O)c1Cl] | White Solid | Hydrolysis | Compound 37 |
| 42 | 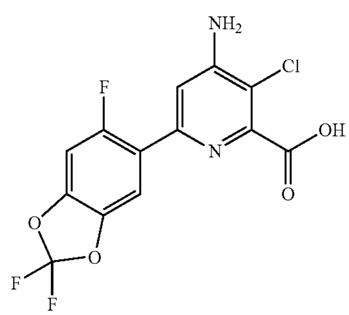 [SMILES: Nc1cc(-c2cc3c(cc2F)OC(F)(F)O3)nc(C(=O)O)c1Cl] | White Solid | Hydrolysis | Compound 32 |
| 43 | 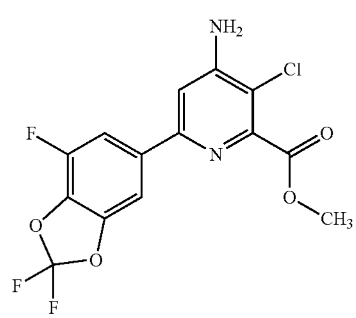 [SMILES: COC(=O)c1nc(-c2cc(F)c3c(c2)OC(F)(F)O3)cc(N)c1Cl] | White Solid | Coupling 1 | Head A; 4,4,5,5-tetramethyl-2-(2,2,7-trifluoro-1,3-benzodioxol-5-yl)-1,3,2-dioxaborolane |

TABLE 2-continued

Compound Number, Structure, Preparation and Appearance

| C. No. | Structure | Appearance | Prepared as described in Example: | Precursor(s) |
|---|---|---|---|---|
| 44 | 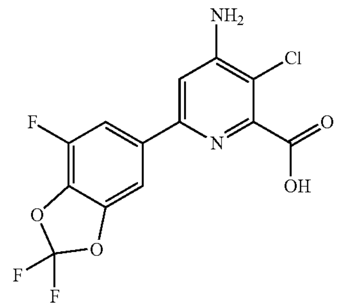 [SMILES: Nc1cc(-c2cc(F)c3c(c2)OC(F)(F)O3)nc(C(=O)O)c1Cl] | White Solid | Hydrolysis | Compound 43 |
| 45 | 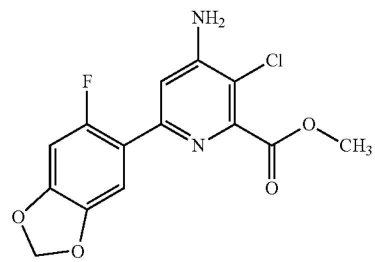 [SMILES: COC(=O)c1nc(-c2cc3c(cc2F)OCO3)cc(N)c1Cl] | Light Yellow Solid | Coupling 1 | Head L; 2-(6-fluorobenzo[d][1,3]dioxol-5-yl)-4,4,5,5-tetramethyl-1,3,2-dioxaborolane |
| 46 | 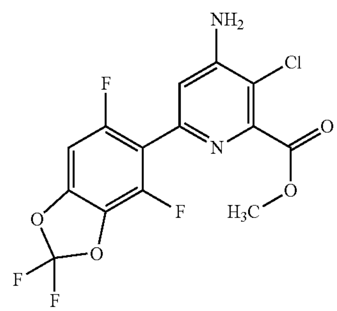 [SMILES: COC(=O)c1nc(-c2c(F)cc3c(c2F)OC(F)(F)O3)cc(N)c1Cl] | Foam | Coupling 4 | Head K; 2,2,4,6-tetrafluoro-5-iodobenzo[d][1,3]dioxole |
| 47 | 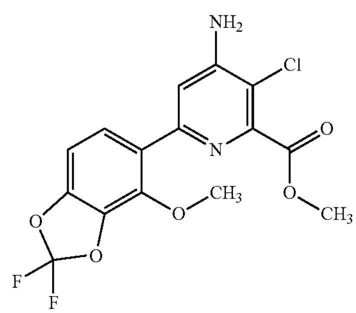 [SMILES: COC(=O)c1nc(-c2ccc3c(c2OC)OC(F)(F)O3)cc(N)c1Cl] | White Solid | Coupling 1 | Head A; 2-(2,2-difluoro-4-methoxybenzo[d][1,3]dioxol-5-yl)-4,4,5,5-tetramethyl-1,3,2-dioxaborolane |
| 48 | 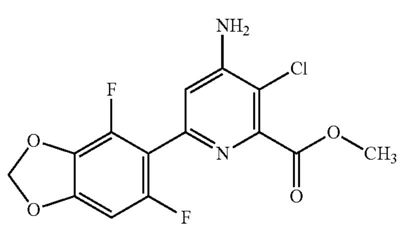 [SMILES: COC(=O)c1nc(-c2c(F)cc3c(c2F)OCO3)cc(N)c1Cl] | White Solid | Coupling 4 | Head K; 4,6-difluoro-5-iodobenzo[d][1,3]dioxole |

TABLE 2-continued

Compound Number, Structure, Preparation and Appearance

| C. No. | Structure | Appearance | Prepared as described in Example: | Precursor(s) |
|---|---|---|---|---|
| 49 | 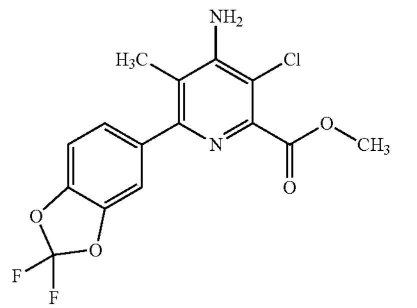 [SMILES: COC(=O)c1nc(-c2ccc3c(c2)OC(F)(F)O3)c(C)c(N)c1Cl] | White Solid | Coupling 1 | Head D; 2-(2,2-difluorobenzo[d][1,3]dioxol-5-yl)-4,4,5,5-tetramethyl-1,3,2-dioxaborolane |
| 50 | 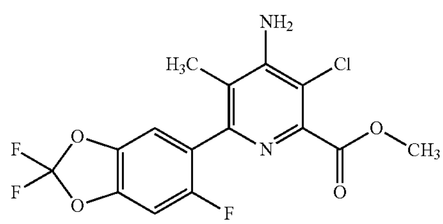 [SMILES: COC(=O)c1nc(-c2cc3c(cc2F)OC(F)(F)O3)c(C)c(N)c1Cl] | White Solid | Coupling 1 | Head D; 4,4,5,5-tetramethyl-2-(2,2,6-trifluorobenzo[d][1,3]dioxol-5-yl)-1,3,2-dioxaborolane |
| 51 | 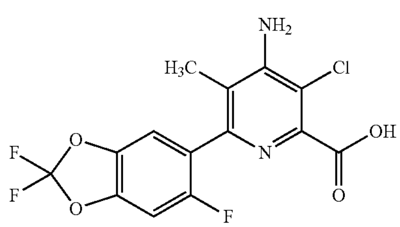 [SMILES: Cc1c(-c2cc3c(cc2F)OC(F)(F)O3)nc(C(=O)O)c(Cl)c1N] | White Solid | Hydrolysis | Compound 50 |
| 52 | 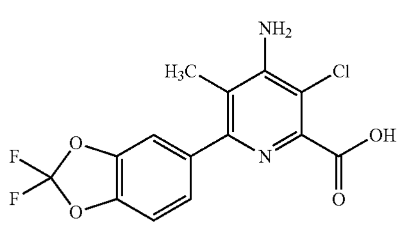 [SMILES: Cc1c(-c2ccc3c(c2)OC(F)(F)O3)nc(C(=O)O)c(Cl)c1N] | Off-White Solid | Hydrolysis | Compound 1 |
| 53 | 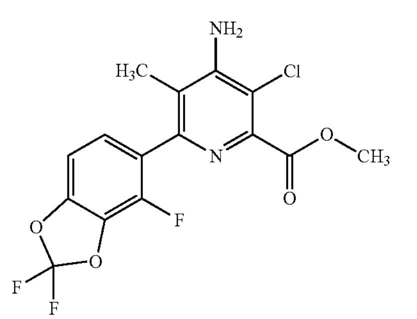 [SMILES: COC(=O)c1nc(-c2ccc3c(c2F)OC(F)(F)O3)c(C)c(N)c1Cl] | White Flaky Solid | Coupling 1 | Head D; 4,4,5,5-tetramethyl-2-(2,2,4-trifluorobenzo[d]3[1,]dioxol-5-yl)-1,3,2-dioxaborolane |

TABLE 2-continued

Compound Number, Structure, Preparation and Appearance

| C. No. | Structure | Appearance | Prepared as described in Example: | Precursor(s) |
|---|---|---|---|---|
| 54 | 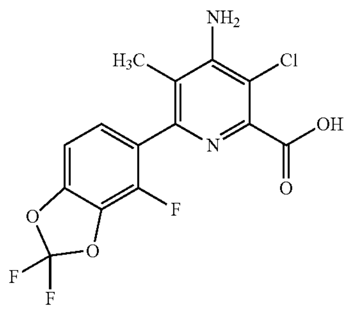 [SMILES: Cc1c(-c2ccc3c(c2F)OC(F)(F)O3)nc(C(=O)O)c(Cl)c1N] | White Solid | Hydrolysis | Compound 53 |
| 55 | 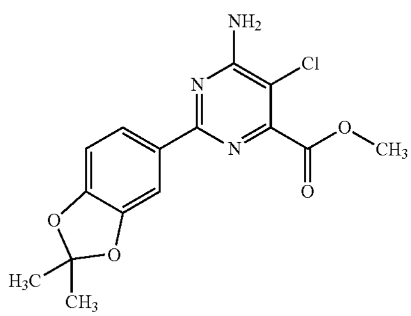 | Dark Brown Solid | Coupling 3 | Head E; 2-(2,2-dimethylbenzo[d]3[1,]dioxol-5-yl)-4,4,5,5-tetramethyl-1,3,2-dioxaborolane |
| 56 | 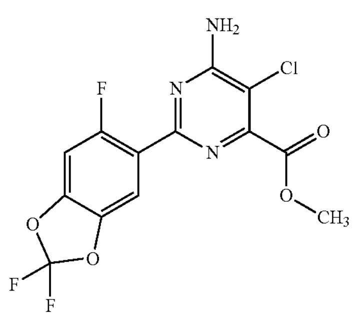 [SMILES: COC(=O)c1nc(-c2cc3c(cc2F)OC(F)(F)O3)nc(N)c1Cl] | White Solid | Coupling 1 | Head E; 4,4,5,5-tetramethyl-2-(2,2,6-trifluoro-1,3-benzodioxol-5-yl)-1,3,2-dioxaborolane |
| 57 | 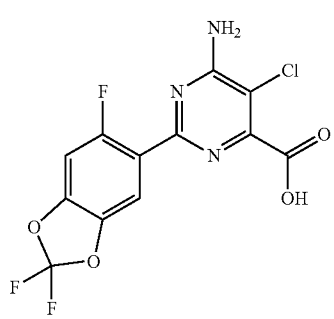 [SMILES: Nc1nc(-c2cc3c(cc2F)OC(F)(F)O3)nc(C(=O)O)c1Cl] | White Solid | Hydrolysis | Compound 56 |

TABLE 2-continued

Compound Number, Structure, Preparation and Appearance

| C. No. | Structure | Appearance | Prepared as described in Example: | Precursor(s) |
|---|---|---|---|---|
| 58 | 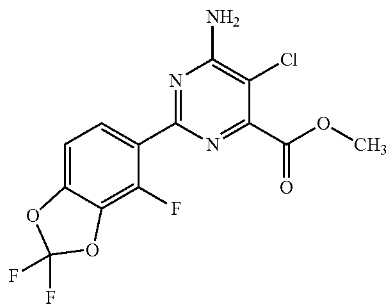 [SMILES: COC(=O)c1nc(-c2ccc3c(c2F)OC(F)(F)O3)nc(N)c1Cl] | White Solid | Coupling 1 | Head E; 4,4,5,5-tetramethyl-2-(2,2,4-trifluorobenzo[d]3]dioxol-5-yl)-1[1,,3,2-dioxaborolane |
| 59 | 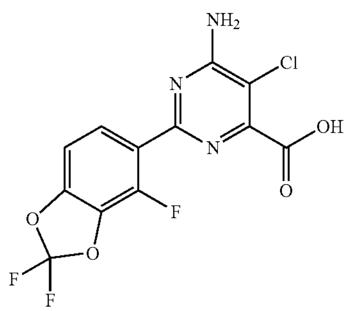 [SMILES: Nc1nc(-c2ccc3c(c2F)OC(F)(F)O3)nc(C(=O)O)c1Cl] | White Solid | Hydrolysis | Compound 58 |
| 60 | 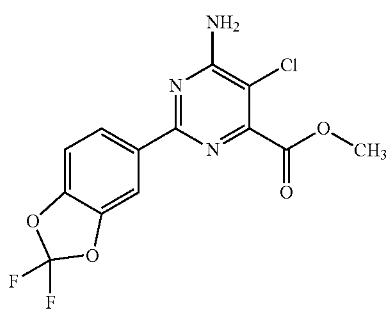 [SMILES: COC(=O)c1nc(-c2ccc3c(c2)OC(F)(F)O3)nc(N)c1Cl] | White Solid | Coupling 1 | Head E; 2-(2,2-difluorobenzo[d][1,3]dioxol-5-yl)-4,4,5,5-tetramethyl-1,3,2-dioxaborolane |
| 61 | 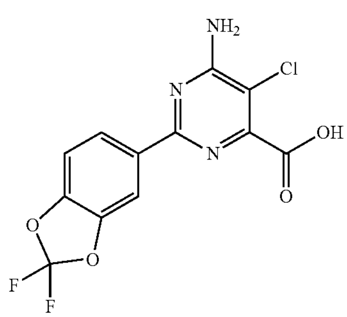 [SMILES: Nc1nc(-c2ccc3c(c2)OC(F)(F)O3)nc(C(=O)O)c1Cl] | White Solid | Hydrolysis | Compound 60 |

TABLE 2-continued

Compound Number, Structure, Preparation and Appearance

| C. No. | Structure | Appearance | Prepared as described in Example: | Precursor(s) |
| --- | --- | --- | --- | --- |
| 62 | 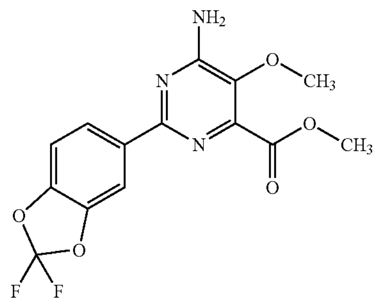 [SMILES: COC(=O)c1nc(-c2ccc3c(c2)OC(F)(F)O3)nc(N)c1OC] | White Solid | Coupling 1 | Head C; 2-(2,2-difluorobenzo[d][1,3]dioxol-5-yl)-4,4,5,5-tetramethyl-1,3,2-dioxaborolane |
| 63 | 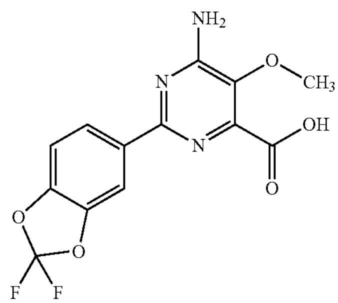 [SMILES: COc1c(N)nc(-c2ccc3c(c2)OC(F)(F)O3)nc1C(=O)O] | White Solid | Hydrolysis | Compound 62 |
| 64 | 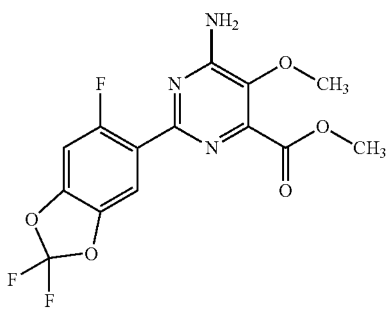 [SMILES: COC(=O)c1nc(-c2cc3c(cc2F)OC(F)(F)O3)nc(N)c1OC] | Tan Solid | Coupling 5 | Head C; 4,4,5,5-tetramethyl-2-(2,2,6-trifluorobenzo[d][1,3]dioxol-5-yl)-1,3,2-dioxaborolane |
| 65 | 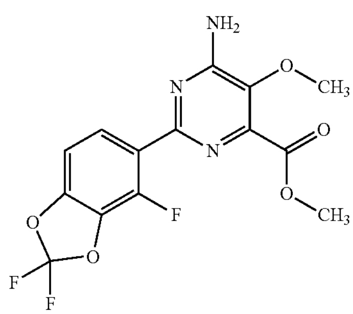 [SMILES: COC(=O)c1nc(-c2ccc3c(c2F)OC(F)(F)O3)nc(N)c1OC] | Tan Solid | Coupling 1 | Head C; 4,4,5,5-tetramethyl-2-(2,2,4-trifluoro-1,3-benzodioxol-5-yl)-1,3,2-dioxaborolane |
| 66 | 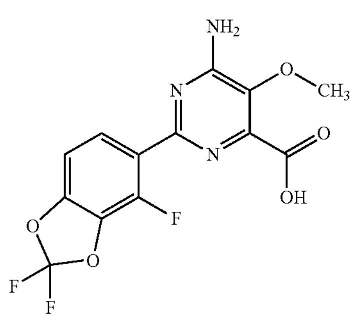 [SMILES: COc1c(N)nc(-c2ccc3c(c2F)OC(F)(F)O3)nc1C(=O)O] | White Solid | Hydrolysis | Compound 65 |

TABLE 2-continued

Compound Number, Structure, Preparation and Appearance

| C. No. | Structure | Appearance | Prepared as described in Example: | Precursor(s) |
|---|---|---|---|---|
| 67 | 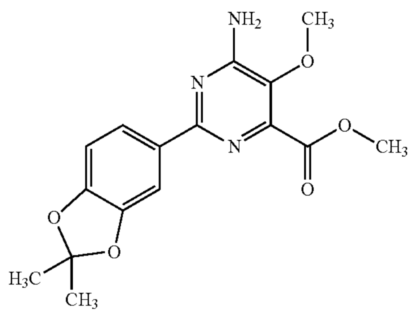 | Dark Brown Solid | Coupling 3 | Head C; 2-(2,2-dimethylbenzo[d][1,3]dioxol-5-yl)-4,4,5,5-tetramethyl-1,3,2-dioxaborolane |
| 68 | 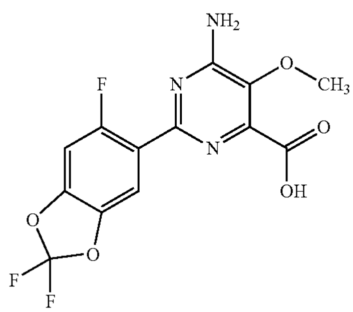 [SMILES: COc1c(N)nc(-c2cc3c(cc2F)OC(F)(F)O3)nc1C(=O)O] | White Solid | Hydrolysis | Compound 64 |
| 69 | 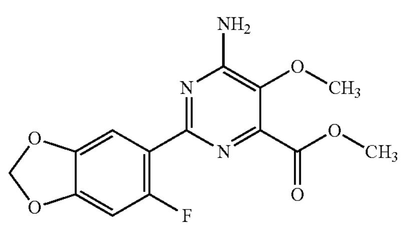 [SMILES: COC(=O)c1nc(-c2cc3c(cc2F)OCO3)nc(N)c1OC] | White Solid | Coupling 1 | Head C; 2-(2,2-dimethylbenzo[d][1,3]dioxol-5-yl)-4,4,5,5-tetramethyl-1,3,2-dioxaborolane |
| 70 | 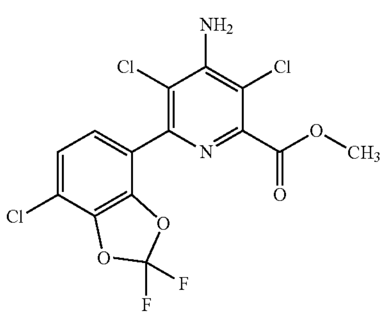 [SMILES: COC(=O)c1nc(-c2ccc(Cl)c3c2OC(F)(F)O3)c(Cl)c(N)c1Cl] | White Solid | Coupling 1 | Head H; 2-(7-chloro-2,2-difluorobenzo[d]3[1,]dioxol-4-yl)-4,4,5,5-tetramethyl-1,3,2-dioxaborolane |
| 71 | 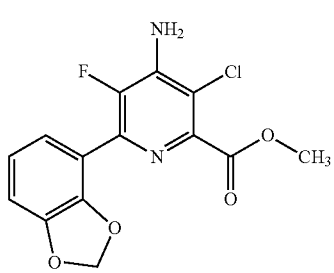 [SMILES: COC(=O)c1nc(-c2cccc3c2OCO3)c(F)c(N)c1Cl] | Off-White Solid | Coupling 1 | As described |

TABLE 2-continued

Compound Number, Structure, Preparation and Appearance

| C. No. | Structure | Appearance | Prepared as described in Example: | Precursor(s) |
|---|---|---|---|---|
| 72 | 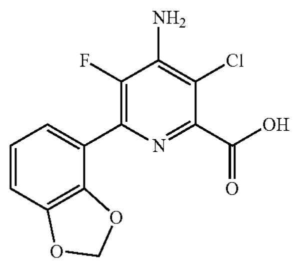 [SMILES: Nc1c(F)c(-c2cccc3c2OCO3)nc(C(=O)O)c1Cl] | White Solid | Hydrolysis | As described |
| 73 | 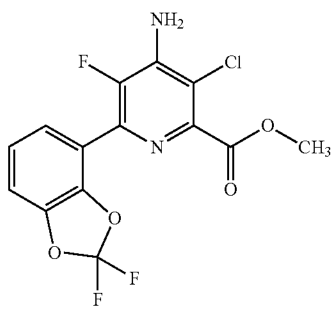 [SMILES: COC(=O)c1nc(-c2cccc3c2OC(F)(F)O3)c(F)c(N)c1Cl] | White Solid | Coupling 1 | Head B; 2-(2,2-difluorobenzo[d][1,3]dioxol-4-yl)-4,4,5,5-tetramethyl-1,3,2-dioxaborolane |
| 74 | 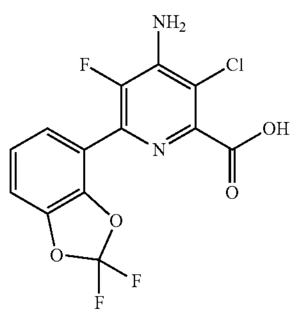 [SMILES: Nc1c(F)c(-c2cccc3c2OC(F)(F)O3)nc(C(=O)O)c1Cl] | White Solid | Hydrolysis | Compound 73 |
| 75 | 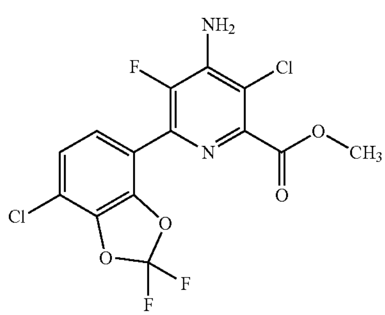 [SMILES: COC(=O)c1nc(-c2ccc(Cl)c3c2OC(F)(F)O3)c(F)c(N)c1Cl] | White Solid | Coupling 1 | Head B; 2-(7-chloro-2,2-difluorobenzo[d][1,3]dioxol-4-yl)-4,4,5,5-tetramethyl-1,3,2-dioxaborolane |
| 76 | 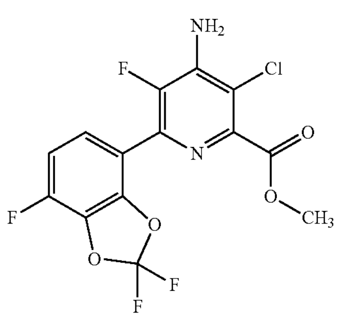 [SMILES: COC(=O)c1nc(-c2ccc(F)c3c2OC(F)(F)O3)c(F)c(N)c1Cl] | White Solid | Coupling 1 | Head B; 4,4,5,5-tetramethyl-2-(2,2,7-trifluoro-1,3-benzodioxol-4-yl)-1,3,2-dioxaborolane |

TABLE 2-continued

Compound Number, Structure, Preparation and Appearance

| C. No. | Structure | Appearance | Prepared as described in Example: | Precursor(s) |
|---|---|---|---|---|
| 77 | 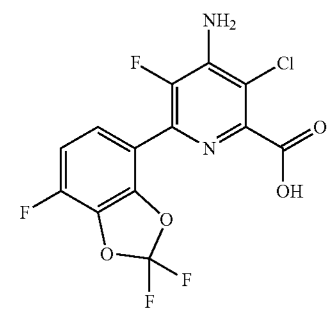 | White Solid | Hydrolysis | Compound 76 |
| 78 | 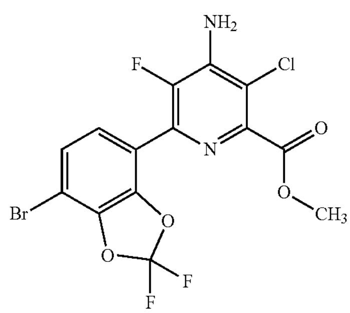 [SMILES: COC(=O)c1nc(-c2ccc(Br)c3c2OC(F)(F)O3)c(F)c(N)c1Cl] | White Solid | 7 | As described |
| 79 | 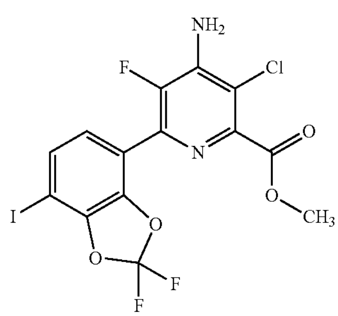 [SMILES: COC(=O)c1nc(-c2ccc(I)c3c2OC(F)(F)O3)c(F)c(N)c1Cl] | White Solid | 8 | As described |
| 80 | 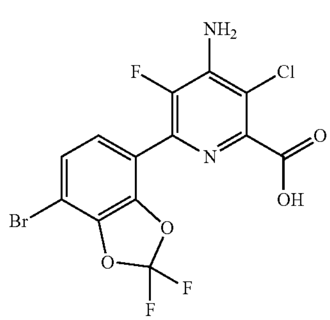 [SMILES: Nc1c(F)c(-c2ccc(Br)c3c2OC(F)(F)O3)nc(C(=O)O)c1Cl] | White Solid | Hydrolysis | Compound 78 |

TABLE 2-continued

Compound Number, Structure, Preparation and Appearance

| C. No. | Structure | Appearance | Prepared as described in Example: | Precursor(s) |
|---|---|---|---|---|
| 81 | 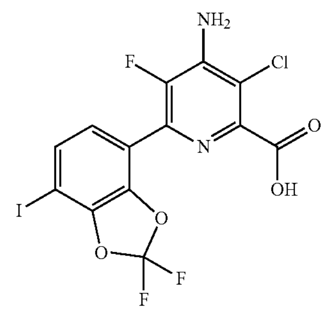 [SMILES: Nc1c(F)c(-c2ccc(I)c3c2OC(F)(F)O3)nc(C(=O)O)c1Cl] | White Solid | Hydrolysis | Compound 79 |
| 82 | 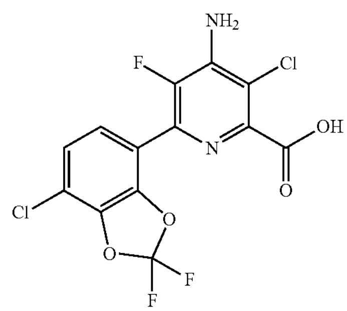 [SMILES: Nc1c(F)c(-c2ccc(Cl)c3c2OC(F)(F)O3)nc(C(=O)O)c1Cl] | White Solid | Hydrolysis | Compound 75 |
| 83 | 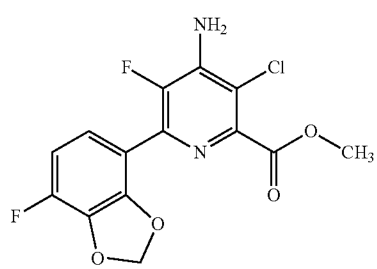 [SMILES: COC(=O)c1nc(-c2ccc(F)c3c2OCO3)c(F)c(N)c1Cl] | White Solid | Coupling 1 | Head B; 2-(7-fluorobenzo[d][1,3]dioxol-4-yl)-4,4,5,5-tetramethyl-1,3,2-dioxaborolane |
| 84 | 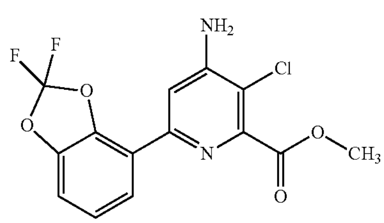 [SMILES: COC(=O)c1nc(-c2cccc3c2OC(F)(F)O3)cc(N)c1Cl] | White Solid | Coupling 1 | Head A; (2,2-difluorobenzo[d][1,3]dioxol-4-yl)boronic acid |
| 85 | 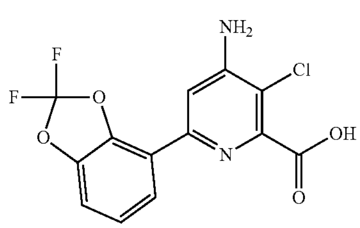 [SMILES: Nc1cc(-c2cccc3c2OC(F)(F)O3)nc(C(=O)O)c1Cl] | White Solid | Hydrolysis | Compound 84 |

TABLE 2-continued

Compound Number, Structure, Preparation and Appearance

| C. No. | Structure | Appearance | Prepared as described in Example: | Precursor(s) |
|---|---|---|---|---|
| 86 | 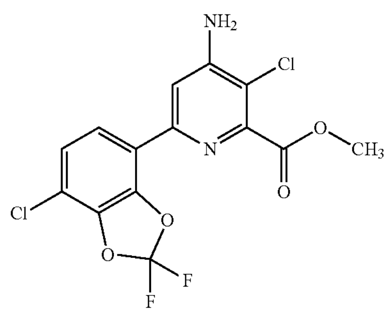 [SMILES: COC(=O)c1nc(-c2ccc(Cl)c3c2OC(F)(F)O3)cc(N)c1Cl] | White Solid | Coupling 1 | Head A; 2-(7-chloro-2,2-difluorobenzo[d][1,3]dioxol-4-yl)-4,4,5,5-tetramethyl-1,3,2-dioxaborolane |
| 87 | 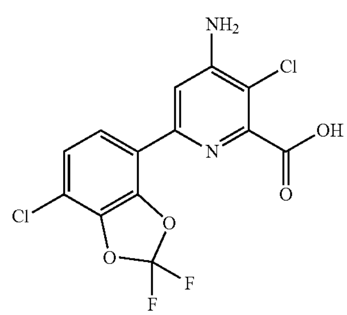 [SMILES: Nc1cc(-c2ccc(Cl)c3c2OC(F)(F)O3)nc(C(=O)O)c1Cl] | White Solid | Hydrolysis | Compound 86 |
| 88 | 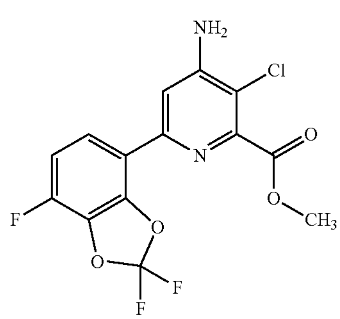 [SMILES: COC(=O)c1nc(-c2ccc(F)c3c2OC(F)(F)O3)cc(N)c1Cl] | White Solid | Coupling 1 | Head A; 4,4,5,5-tetramethyl-2-(2,2,7-trifluoro-1,3-benzodioxol-4-yl)-1,3,2-dioxaborolane |
| 89 | 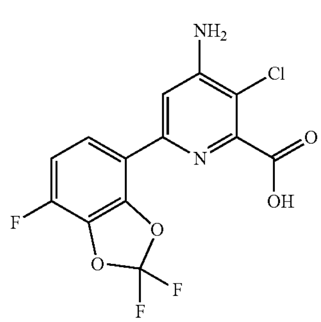 [SMILES: Nc1cc(-c2ccc(F)c3c2OC(F)(F)O3)nc(C(=O)O)c1Cl] | White Solid | Hydrolysis | Compound 88 |

TABLE 2-continued

Compound Number, Structure, Preparation and Appearance

| C. No. | Structure | Appearance | Prepared as described in Example: | Precursor(s) |
|---|---|---|---|---|
| 90 | 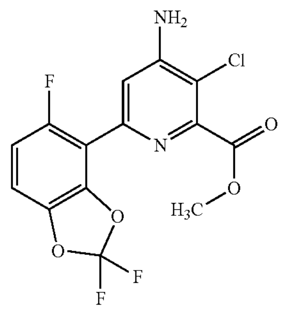 [SMILES: COC(=O)c1nc(-c2c(F)ccc3c2OC(F)(F)O3)cc(N)c1Cl] | White Solid | Coupling 4 | Head K; 2,2,5-trifluoro-4-iodobenzo[d][1,3]dioxole |
| 91 | 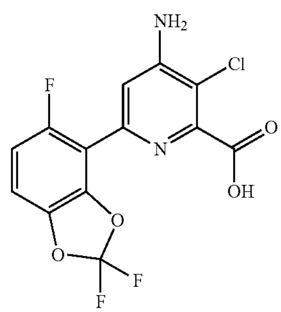 [SMILES: Nc1cc(-c2c(F)ccc3c2OC(F)(F)O3)nc(C(=O)O)c1Cl] | White Solid | Hydrolysis | Compound 90 |
| 92 | 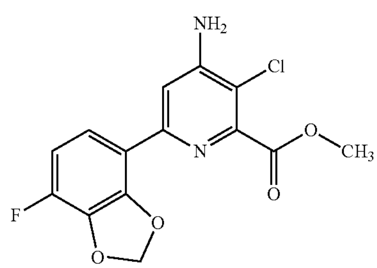 [SMILES: COC(=O)c1nc(-c2ccc(F)c3c2OCO3)cc(N)c1Cl] | Brown Solid | Coupling 1 | Head M; 2-(7-fluorobenzo[d][1,3]dioxol-4-yl)-4,4,5,5-tetramethyl-1,3,2-dioxaborolane |
| 93 | 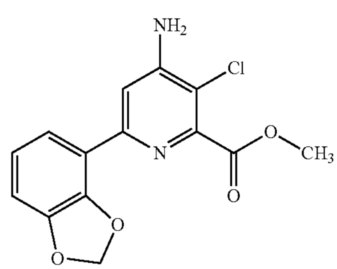 [SMILES: COC(=O)c1nc(-c2cccc3c2OCO3)cc(N)c1Cl] | Clear Glass | Coupling 1 | Head M; 2-(benzo[d][1,3]dioxol-4-yl)-4,4,5,5-tetramethyl-1,3,2-dioxaborolane |
| 94 | 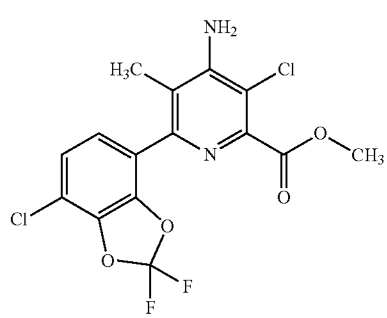 [SMILES: COC(=O)c1nc(-c2ccc(Cl)c3c2OC(F)(F)O3)c(C)c(N)c1Cl] | White Solid | Coupling 1 | Head D 2-(7-chloro-2,2-difluorobenzo[d][1,3]dioxol-4-yl)-4,4,5,5-tetramethyl-1,3,2-dioxaborolane |

TABLE 2-continued

Compound Number, Structure, Preparation and Appearance

| C. No. | Structure | Appearance | Prepared as described in Example: | Precursor(s) |
|---|---|---|---|---|
| 95 | 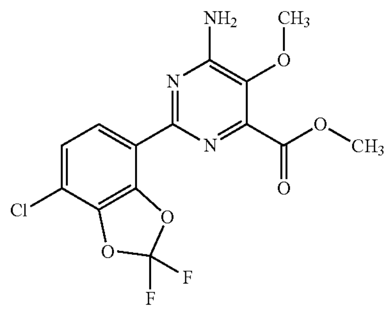 [SMILES: COC(=O)c1nc(-c2ccc(Cl)c3c2OC(F)(F)O3)nc(N)c1OC] | Off-White Solid | Coupling 1 | Head C; 2-(7-chloro-2,2-difluorobenzo[d][1,3]dioxol-4-yl)-4,4,5,5-tetramethyl-1,3,2-dioxaborolane |
| 96 | 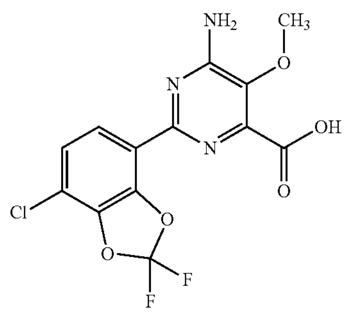 [SMILES: COc1c(N)nc(-c2ccc(Cl)c3c2OC(F)(F)O3)nc1C(=O)O] | White Solid | Hydrolysis | Compound 75 |
| 97 | 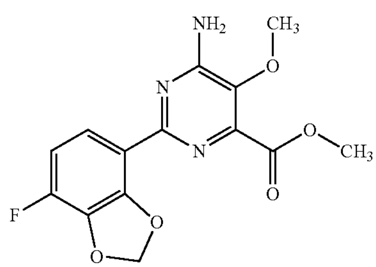 [SMILES: COC(=O)c1nc(-c2ccc(F)c3c2OCO3)nc(N)c1OC] | Light Yellow Solid | Coupling 1 | Head C; 2-(7-fluorobenzo[d][1,3]dioxol-4-yl)-4,4,5,5-tetramethyl-1,3,2-dioxaborolane |
| 98 | 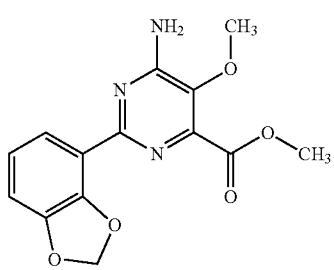 [SMILES: COC(=O)c1nc(-c2cccc3c2OCO3)nc(N)c1OC] | White Solid | Coupling 1 | Head C; 2-(benzo[d][1,3]dioxol-4-yl)-4,4,5,5-tetramethyl-1,3,2-dioxaborolane |
| 99 | 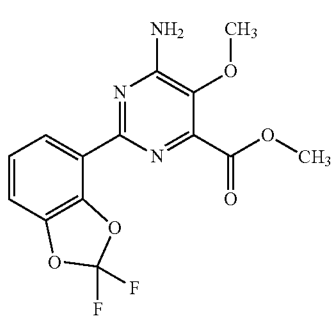 [SMILES: COC(=O)c1nc(-c2cccc3c2OC(F)(F)O3)nc(N)c1OC] | White Solid | Coupling 1 | Head C; 2-(2,2-difluorobenzo[d][1,3]dioxol-4-yl)-4,4,5,5-tetramethyl-1,3,2-dioxaborolane |

TABLE 2-continued

Compound Number, Structure, Preparation and Appearance

| C. No. | Structure | Appearance | Prepared as described in Example: | Precursor(s) |
|---|---|---|---|---|
| 100 | 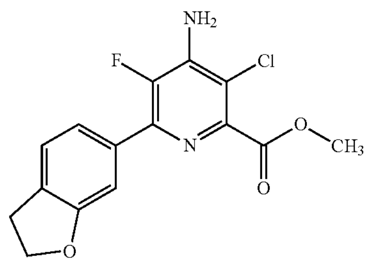 [SMILES: COC(=O)c1nc(-c2ccc3c(c2)OCC3)c(F)c(N)c1Cl] | White Solid | Coupling 3 | As described |
| 101 | 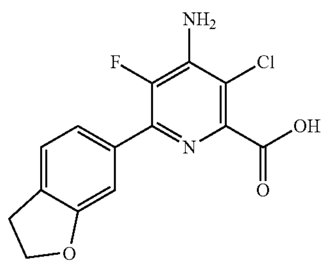 [SMILES: Nc1c(F)c(-c2ccc3c(c2)OCC3)nc(C(=O)O)c1Cl] | White Solid | Hydrolysis | Compound 100 |
| 102 | 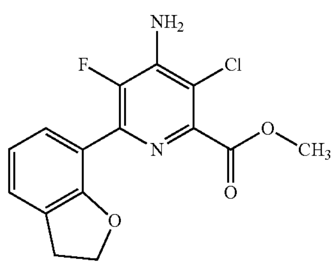 | White Solid | Coupling 1 | Head B; 2-(2,3-dihydrobenzofuran-7-yl)-4,4,5,5-tetramethyl-1,3,2-dioxaborolane |
| 103 | 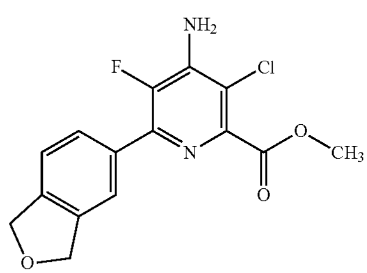 [SMILES: COC(=O)c1nc(-c2ccc3c(c2)COC3)c(F)c(N)c1Cl] | Orange Powder | 1 | As described |
| 104 | 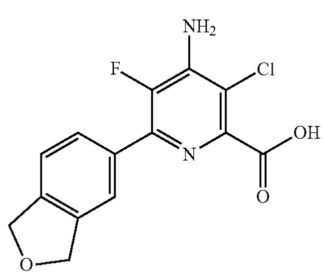 [SMILES: Nc1c(F)c(-c2ccc3c(c2)COC3)nc(C(=O)O)c1Cl] | Orange Powder | Hydrolysis | Compound 103 |

TABLE 2-continued

Compound Number, Structure, Preparation and Appearance

| C. No. | Structure | Appearance | Prepared as described in Example: | Precursor(s) |
|---|---|---|---|---|
| 105 | 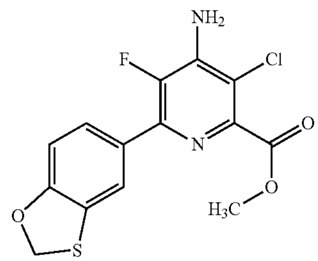 [SMILES: COC(=O)c1nc(-c2ccc3c(c2)SCO3)c(F)c(N)c1Cl] | Tan Solid | Coupling 1 | Head B; 2-(benzo[d][1,3]oxathiol-5-yl)-4,4,5,5-tetramethyl-1,3,2-dioxaborolane |
| 106 | 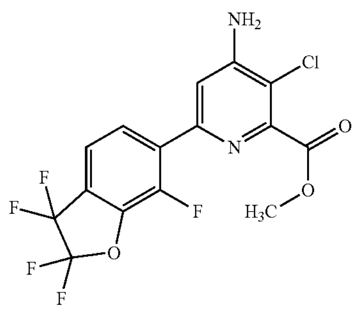 [SMILES: COC(=O)c1nc(-c2ccc3c(c2F)OC(F)(F)C3(F)F)cc(N)c1Cl] | White Solid | Coupling 4 | Head K; 2,2,3,3,7-pentafluoro-6-iodo-2,3-dihydrobenzofuran |
| 107 | 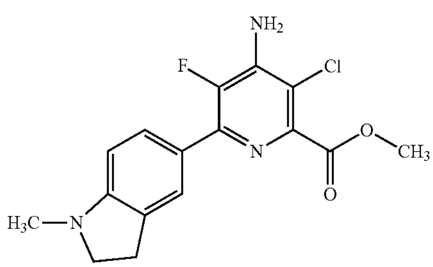 | Pale Yellow Powder | Coupling 1 | Head B; 1-methyl-5-(4,4,5,5-tetramethyl-1,3,2-dioxaborolan-2-yl)indoline |
| 108 | 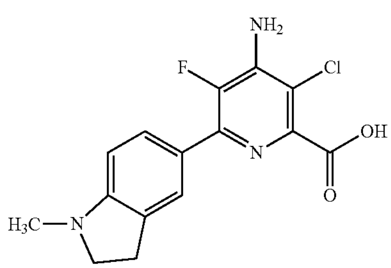 [SMILES: CN1CCc2cc(-c3nc(C(=O)O)c(Cl)c(N)c3F)ccc21] | Yellow Powder | Hydrolysis | Compound 107 |

TABLE 3

Analytical Data for Compounds in Table 1

| C. No. | MP (° C.) | $^1$H NMR |
|---|---|---|
| 1 | 141-144 | $^1$H NMR (CDCl$_3$) δ 7.41 (ddd, J = 5.0, 2.1, 1.1 Hz, 2H), 7.13 (dd, J = 8.3, 0.4 Hz, 1H), 5.35 (s, 2H), 3.97 (s, 3H) |
| 2 | 161-163 | $^1$H NMR (400 MHz, CDCl$_3$) δ 7.14 (d, J = 5.5 Hz, 1H), 6.92 (d, J = 8.2 Hz, 1H), 5.36 (s, 2H), 3.97 (s, 3H) |
| 3 | 145-146 (dec) | $^1$H NMR (400 MHz, DMSO-d$_6$) δ 7.68 (d, J = 8.7 Hz, 1H), 7.58 (d, J = 5.7 Hz, 1H), 7.08 (s, 2H) |
| 4 | | $^1$H NMR (DMSO-d$_6$) δ 3.87 (s, 3H), 7.22 (s, 2H), 7.33 (dd, J = 8.4, 6.4 Hz, 1H), 7.43 (d, J = 8.5 Hz, 1H) |
| 5 | | $^1$H NMR (DMSO-d$_6$) δ 7.12 (s, 2H), 7.33 (dd, J = 8.4, 6.4 Hz, 1H), 7.44 (d, J = 8.5 Hz, 1H), 13.81 (s, 1H) |

TABLE 3-continued

Analytical Data for Compounds in Table 1

| C. No. | MP (° C.) | ¹H NMR |
|---|---|---|
| 6 | 137-139 | ¹H NMR (400 MHz, DMSO-$d_6$) δ 7.78 (s, 1H), 7.68 (d, J = 8.5 Hz, 1H), 7.55 (d, J = 8.5 Hz, 1H), 7.05 (s, 2H), 3.88 (s, 3H) |
| 7 | 143-144 | ¹H NMR (400 MHz, DMSO-$d_6$) δ 13.52 (s, 1H), 7.82 (s, 1H), 7.75-7.67 (m, 1H), 7.54 (d, J = 8.6 Hz, 1H), 6.92 (s, 2H) |
| 8 |  | ¹H NMR (400 MHz, CDCl$_3$) δ 7.41 (dt, J = 8.2, 1.7 Hz, 1H), 7.34 (t, J = 1.5 Hz, 1H), 6.80 (d, J = 8.2 Hz, 1H), 4.85 (s, 2H), 3.98 (s, 3H), 1.70 (s, 6H) |
| 9 | 151-153 | ¹H NMR (400 MHz, CDCl$_3$) δ 7.31 (d, J = 5.5 Hz, 1H), 6.93 (dd, J = 8.3, 5.1 Hz, 1H), 4.97 (s, 2H), 3.98 (s, 3H) |
| 10 | 91-93 | ¹H NMR (400 MHz, CDCl$_3$) δ 7.35 (dd, J = 8.4, 6.2 Hz, 1H), 7.01 (dd, J = 8.4, 0.8 Hz, 1H), 4.98 (s, 2H), 3.98 (d, J = 4.0 Hz, 3H) |
| 11 | 142-143 (dec) | ¹H NMR (400 MHz, DMSO-$d_6$) δ 13.70 (s, 1H), 7.49-7.40 (m, 1H), 7.05 (s, 1H). |
| 12 | 146-148 | ¹H NMR (400 MHz, CDCl$_3$) δ 7.20 (s, 1H), 7.18 (s, 1H), 4.99 (s, 2H), 3.97 (s, 3H). |
| 13 | 161-162 (dec) | ¹H NMR (400 MHz, DMSO-$d_6$) δ 7.70 (d, J = 9.0 Hz, 1H), 7.62 (d, J = 5.7 Hz, 1H), 7.00 (s, 2H) |
| 14 | 153-155 | ¹H NMR (400 MHz, CDCl$_3$) δ 7.21-7.16 (m, 1H), 7.13 (t, J = 1.6 Hz, 1H), 6.03 (s, 2H), 4.88 (s, 2H), 3.99 (s, 3H), 3.96 (s, 3H) |
| 15 | 173-174 (dec) | ¹H NMR (400 MHz, DMSO-$d_6$) δ 13.51 (s, 1H), 7.14 (s, 1H), 7.05 (s, 1H), 6.86 (s, 2H), 6.08 (s, 2H), 3.88 (s, 3H) |
| 16 |  | ¹H NMR (400 MHz, CDCl$_3$) δ 7.01 (d, J = 5.8 Hz, 1H), 6.67 (d, J = 9.2 Hz, 1H), 6.04 (d, J = 12.7 Hz, 2H), 4.92 (s, 2H), 3.98 (s, 3H) |
| 17 | 135-137 | ¹H NMR (400 MHz, CDCl$_3$) δ 7.62 (m, 1H), 7.57 (d, J = 0.7 Hz, 1H), 4.95 (s, 2H), 4.00 (s, 3H) |
| 18 | 157-159 | ¹H NMR (400 MHz, DMSO-$d_6$) δ 13.34 (s, 1H), 7.73 (s, 1H), 7.68 (m, 1H), 6.97 (s, 2H) |
| 19 |  | ¹H NMR (400 MHz, DMSO-$d_6$) δ 7.32-7.25 (m, 1H), 7.21 (s, 1H), 6.89 (d, J = 8.2 Hz, 1H), 1.67 (s, 6H) |
| 20 | 101-103 | ¹H NMR (400 MHz, CDCl$_3$) δ 7.44 (dt, J = 8.2, 1.7 Hz, 1H), 7.38 (t, J = 1.5 Hz, 1H), 6.84 (d, J = 8.3 Hz, 1H), 6.32 (q, J = 4.9 Hz, 1H), 4.86 (s, 2H), 3.98 (s, 3H), 1.69 (d, 4.9 hz, 3H) |
| 21 | 231-232 | ¹H NMR (400 MHz, DMSO-$d_6$) δ 7.70 (d, J = 9.0 Hz, 1H), 7.60 (d, J = 5.7 Hz, 1H), 6.95 (s, 2H), 3.86 (s, 3H) |
| 22 | 147 | ¹H NMR (400 MHz, acetone-$d_6$) δ 7.48 (d, J = 5.6 Hz, 1H), 7.39 (d, J = 8.8 Hz, 1H), 6.01 (s, 2H), 3.93 (s, 3H), 3.90 (s, 3H) |
| 23 | 156 | ¹H NMR (400 MHz, acetone-$d_6$) δ 7.62 (d, J = 5.6 Hz, 1H), 7.40 (d, J = 8.9 Hz, 1H), 6.18 (s, 1H), 3.97 (s, 3H) |
| 24 | 125.5-127.0 | ¹H NMR (CDCl$_3$) δ 7.73-7.65 (m, 2H), 7.13 (dd, J = 8.2, 0.6 Hz, 1H), 4.58 (s, 2H), 3.99 (s, 3H), 3.96 (s, 3H) |
| 25 | 132-134 | ¹H NMR (CDCl$_3$) δ 7.62 (dt, J = 8.4, 1.5 Hz, 1H), 7.57 (t, J = 1.4 Hz, 1H), 7.19 (d, J = 8.4 Hz, 1H), 4.83 (s, 2H), 4.06 (s, 3H) |
| 26 |  | ¹H NMR (400 MHz, CDCl$_3$) δ 7.01 (d, J = 5.8 Hz, 1H), 6.66 (d, J = 9.2 Hz, 1H), 6.01 (s, 2H), 4.57 (s, 2H), 3.96 (s, 3H). 3.97 (s, 3H) |
| 27 | 118-120 | ¹H NMR (400 MHz, CDCl$_3$) δ 7.33 (d, J = 5.5 Hz, 1H), 6.96-6.86 (m, 2H), 5.73 (dd, J = 11.6, 1.3 Hz, 1H), 5.59 (dd, J = 18.1, 1.4 Hz, 1H), 4.76 (s, 2H), 3.92 (s, 3H). |
| 28 | 162-165 (dec) | ¹H NMR (400 MHz, DMSO-$d_6$) δ 13.17 (s, 1H), 7.68 (d, J = 9.0 Hz, 1H), 7.61 (d, J = 5.7 Hz, 1H), 6.83-6.71 (m, 1H), 6.49 (s, 2H), 5.57 (dd, J = 6.2, 1.2 Hz, 1H), 5.54 (s, 1H) |
| 29 | 112-114 | ¹H NMR (CDCl$_3$) δ 7.74 (ddd, J = 6.1, 3.1, 1.3 Hz, 2H), 7.14 (dd, J = 8.3, 0.4 Hz, 1H), 6.90 (dd, J = 18.1, 11.6 Hz, 1H), 5.72 (dd, J = 11.6, 1.4 Hz, 1H), 5.58 (dd, J = 18.1, 1.4 Hz, 1H), 4.73 (s, 2H), 3.93 (s, 3H) |
| 30 |  | ¹H NMR (CDCl$_3$) δ 7.72-7.65 (m, 1H), 7.62 (t, J = 1.3 Hz, 1H), 7.29-7.22 (m, 1H), 7.20 (d, J = 8.3 Hz, 1H), 5.82 (dd, J = 11.7, 1.4 Hz, 1H), 5.62 (dd, J = 18.4, 1.4 Hz, 1H), 5.02 (s, 2H). |
| 31 |  | ¹H NMR (400 MHz, CDCl$_3$) δ 7.04 (d, J = 5.8 Hz, 1H), 6.91 (dd, J = 18.1, 11.5 Hz, 1H), 6.66 (d, J = 9.2 Hz, 1H), 6.02 (s, 2H), 5.71 (dd, J = 11.5, 1.4 Hz, 1H), 5.58 (dd, J = 18.1, 1.4 Hz, 1H), 4.71 (s, 2H), 3.91 (s, 3H) |
| 32 | 150-151 | ¹H NMR (400 MHz, acetone-$d_6$) δ 7.84 (d, J = 6.2 Hz, 1H), 7.39 (d, J = 1.7 Hz, 1H), 7.35 (d, J = 10.2 Hz, 1H), 6.34 (s, 1H), 3.93 (s, 3H) |
| 33 | 145-146 | ¹H NMR (400 MHz, CDCl$_3$) δ 7.37 (d, J = 8.3 Hz, 1H), 7.05 (d, J = 8.4 Hz, 1H), 6.99 (s, 1H), 4.91 (s, 2H), 3.98 (s, 3H) |
| 34 | 153-155 | ¹H NMR (400 MHz, DMSO-$d_6$) δ 13.57 (s, 1H), 7.51 (d, J = 8.4 Hz, 1H), 7.42 (d, J = 8.4 Hz, 1H), 6.98 (s, 1H), 6.81 (s, 2H) |
| 35 | 116-118 | ¹H NMR (400 MHz, CDCl$_3$) δ 7.10 (d, J = 8.2 Hz, 1H), 6.96-6.89 (m, 1H), 6.76 (s, 1H), 4.86 (s, 2H), 3.97 (s, 3H) |
| 36 | 172-174 | ¹H NMR (400 MHz, DMSO-$d_6$) δ 13.46 (s, 1H), 7.30 (d, J = 8.2 Hz, 1H), 7.22 (d, J = 8.3 Hz, 1H), 6.83 (s, 1H), 6.71 (s, 2H), 2.27 (s, 3H) |
| 37 | 153-155 | ¹H NMR (400 MHz, CDCl$_3$) δ 7.77 (dd, J = 8.6, 7.1 Hz, 1H), 7.14 (d, J = 1.9 Hz, 1H), 6.97 (dd, J = 8.6, 0.9 Hz, 1H), 4.87 (s, 2H), 4.00 (s, 3H) |
| 38 |  | ¹H NMR (400 MHz, CDCl$_3$) δ 7.60 (s, 1H), 7.29 (s, 1H), 6.76 (s, 1H), 4.77 (s, 2H), 3.98 (s, 3H), 3.82 (s, 3H) |

TABLE 3-continued

Analytical Data for Compounds in Table 1

| C. No. | MP (° C.) | ¹H NMR |
|---|---|---|
| 39 | 165-166 | ¹H NMR (400 MHz, DMSO-$d_6$) δ 7.66 (s, 1H), 7.39 (s, 1H), 7.27 (s, 1H), 6.70 (s, 2H), 3.85 (s, 3H) |
| 40 | 127-129 | ¹H NMR (400 MHz, CDCl$_3$) δ 7.33 (s, 1H), 7.16 (s, 1H), 7.03 (s, 1H), 4.91 (s, 2H), 3.98 (s, 3H) |
| 41 | 173-175 | ¹H NMR (400 MHz, DMSO-$d_6$) δ 7.73 (dd, J = 8.6, 7.3 Hz, 1H), 7.39 (d, J = 8.6 Hz, 1H), 7.16 (d, J = 1.9 Hz, 1H), 6.83 (s, 2H) |
| 42 | 173-174 | ¹H NMR (400 MHz, DMSO-$d_6$) δ 13.54 (s, 1H), 7.84 (d, J = 6.3 Hz, 1H), 7.66 (d, J = 10.2 Hz, 1H), 7.20 (d, J = 1.9 Hz, 1H), 6.82 (s, 2H) |
| 43 | 176-77 | ¹H NMR (400 MHz, CDCl$_3$) δ 7.75 (d, J = 1.8 Hz, 1H), 7.71 (dd, J = 11.5, 1.5 Hz, 1H), 6.79 (s, 2H), 3.90 (s, 3H) |
| 44 | 182-183 (dec) | ¹H NMR (400 MHz, DMSO-$d_6$) δ 13.32 (s, 1H), 7.77 (m, 2H), 7.25 (s, 1H), 6.76 (s, 2H) |
| 45 |  | ¹H NMR (400 MHz, CDCl$_3$) δ 7.89 (dd, J = 8.2, 1.7 Hz, 1H), 7.72 (d, J = 1.7 Hz, 1H), 6.77 (d, J = 8.2 Hz, 1H), 5.49 (s, 2H), 4.01 (s, 3H), 1.69 (s, 6H) |
| 46 |  | ¹H NMR (400 MHz, CDCl$_3$) δ 6.95 (s, 1H), 6.78 (dd, J = 22.3, 11.8 Hz, 1H), 5.01 (s, 2H), 3.99 (s, 3H) |
| 47 | 115-116 | ¹H NMR (400 MHz, CDCl$_3$) δ 7.51 (d, J = 8.5 Hz, 1H), 7.14 (s, 1H), 6.81 (d, J = 8.5 Hz, 1H), 4.80 (s, 2H), δ 4.02 (s, 3H), 3.98 (s, 3H) |
| 48 | 135-140 | ¹H NMR (400 MHz, CDCl$_3$) δ 6.83 (s, 1H), 6.53 (dd, J = 8.7, 1.3 Hz, 1H), 6.06 (d, J = 7.1 Hz, 2H), 4.85 (s, 2H), 3.98 (s, 3H) |
| 49 | 158-160 | ¹H NMR (CDCl$_3$) δ 7.21 (dd, J = 1.6, 0.4 Hz, 1H), 7.16 (dd, J = 8.2, 1.6 Hz, 1H), 7.10 (dd, J = 8.2, 0.4 Hz, 1H), 4.85 (s, 2H), 3.96 (s, 3H), 2.17 (s, 3H) |
| 50 | 162-165 | ¹H NMR (CDCl$_3$) δ 7.17 (d, J = 5.6 Hz, 1H), 6.90 (d, J = 8.2 Hz, 1H), 4.86 (s, 2H), 3.96 (s, 3H), 2.09 (d, J = 2.8 Hz, 3H) |
| 51 | 125.5-127.0 | ¹H NMR (CDCl$_3$) δ 7.12 (d, J = 5.6 Hz, 1H), 6.97 (d, J = 8.3 Hz, 1H), 5.12 (s, 2H), 2.13 (d, J = 2.6 Hz, 3H) |
| 52 | 150-153 | ¹H NMR (CDCl$_3$) δ 7.18-7.16 (m, 3H), 5.11 (s, 2H), 2.23 (s, 3H) |
| 53 | 153.5-155.0 | ¹H NMR (400 MHz, CDCl$_3$) δ 7.17 (dd, J = 8.3, 6.4 Hz, 1H), 6.97 (dd, J = 8.3, 0.8 Hz, 1H), 4.87 (s, 2H), 3.95 (s, 3H), 2.09 (d, J = 2.3 Hz, 3H) |
| 54 | 139-147 | ¹H NMR (400 MHz, DMSO-$d_6$) δ 7.39 (d, J = 8.4 Hz, 1H), 7.25 (dd, J = 8.4, 6.6 Hz, 1H), 6.53 (s, 2H), 2.00 (d, J = 1.7 Hz, 3H) |
| 55 | 132-139 | ¹H NMR (400 MHz, CDCl$_3$) δ 7.89 (dd, J = 8.2, 1.7 Hz, 1H), 7.72 (d, J = 1.7 Hz, 1H), 6.77 (d, J = 8.2 Hz, 1H), 5.49 (s, 2H), 4.00 (s, 3H), 1.69 (s, 6H) |
| 56 |  | ¹H NMR (400 MHz, CDCl$_3$) δ 7.73 (d, J = 6.0 Hz, 1H), 6.92 (d, J = 9.3 Hz, 1H), 5.65 (s, 2H), 4.01 (s, 3H) |
| 57 | 178-179 | ¹H NMR (400 MHz, DMSO-$d_6$) δ 8.15-7.87 (m, 1H), 7.81 (d, J = 6.1 Hz, 1H), 7.63 (d, J = 9.7 Hz, 2H) |
| 58 |  | ¹H NMR (DMSO-$d_6$) δ 3.92 (s, 3H), 7.40 (dd, J = 8.7, 0.9 Hz, 1H), 7.65 (s, 1H), 7.81 (dd, J = 8.7, 7.1 Hz, 1H), 8.16 (s, 1H) |
| 59 |  | ¹H NMR (DMSO-$d_6$) δ 7.41 (d, J = 8.6 Hz, 1H), 7.46-7.75 (m, 1H), 7.82 (dd, J = 8.7, 7.0 Hz, 1H), 7.89-8.41 (m, 1H), 14.13 (s, 1H) |
| 60 |  | ¹H NMR (DMSO-$d_6$) δ 3.93 (s, 3H), 7.53 (d, J = 8.5 Hz, 1H), 8.07 (d, J = 1.8 Hz, 1H), 8.15 (dd, J = 8.5, 1.7 Hz, 1H) |
| 61 |  | ¹H NMR (DMSO-$d_6$) δ 7.53 (d, J = 8.5 Hz, 1H), 7.87 (s, 1H), 8.10 (d, J = 1.6 Hz, 1H), 8.16 (dd, J = 8.5, 1.7 Hz, 1H), 14.07 (s, 1H) |
| 62 | 178 | ¹H NMR (400 MHz, DMSO-$d_6$) δ 8.11 (dd, J = 8.5, 1.7 Hz, 1H), 8.06-8.01 (m, 1H), 7.52-7.47 (m, 1H), 7.42 (s, 2H), 3.90 (s, 3H), 3.74 (s, 3H) |
| 63 | 144-145 | ¹H NMR (400 MHz, DMSO-$d_6$) δ 8.13 (dd, J = 8.5, 1.6 Hz, 1H), 8.08 (d, J = 1.5 Hz, 1H), 7.47 (d, J = 8.5 Hz, 1H), 7.15 (s, 2H), 3.76 (s, 3H) |
| 64 | 131-132 | ¹H NMR (400 MHz, CDCl$_3$) δ 7.67 (d, J = 6.0 Hz, 1H), 6.91 (d, J = 9.3 Hz, 1H), 5.48 (s, 2H), 4.00 (s, 3H), 3.94 (s, 3H) |
| 65 | 109-111 | ¹H NMR (400 MHz, CDCl$_3$) δ 7.74 (dd, J = 8.5, 6.8 Hz, 1H), 6.93 (dd, J = 8.5, 0.9 Hz, 1H), 5.45 (s, 2H), 4.00 (s, 3H), 3.94 (s, 3H) |
| 66 | 125-126 (dec) | ¹H NMR (400 MHz, DMSO-$d_6$) δ 7.77 (dd, J = 8.6, 7.1 Hz, 1H), 7.37 (dd, J = 8.6, 0.7 Hz, 3H), 3.76 (s, 3H) |
| 67 | 159-164 | ¹H NMR (400 MHz, CDCl$_3$) δ 7.83 (dd, J = 8.2, 1.6 Hz, 1H), 7.70 (d, J = 1.6 Hz, 1H), 6.76 (d, J = 8.2 Hz, 1H), 5.28 (s, 2H), 4.00 (s, 3H), 3.90 (s, 3H), 1.69 (s, 6H) |
| 68 | 119-120 (dec) | ¹H NMR (400 MHz, DMSO-$d_6$) δ 7.78 (d, J = 6.1 Hz, 1H), 7.59 (d, J = 9.6 Hz, 1H), 7.38 (s, 2H), 3.76 (s, 3H) |
| 69 |  | ¹H NMR (DMSO-$d_6$) δ 3.74 (s, 3H), 3.88 (s, 3H), 6.12 (s, 2H), 6.98 (d, J = 10.3 Hz, 1H), 7.26 (d, J = 6.4 Hz, 1H), 7.37 (s, 2H) |
| 70 | 161-164 | ¹H NMR (400 MHz, CDCl$_3$) δ 7.21 (m, 2H), 5.39 (s, 2H), 3.98 (s, 3H) |
| 71 | 146-148 | ¹H NMR (400 MHz, CDCl$_3$) δ 7.16-7.09 (m, 1H), 6.98-6.85 (m, 2H), 6.01 (s, 2H), 4.91 (br s, 2H), 3.98 (s, 3H) |
| 72 | 171-173 | ¹H NMR (400 MHz, DMSO-$d_6$) δ 7.08-7.00 (m, 2H), 6.99-6.94 (m, 1H), 6.93 (br s, 2H), 6.06 (s, 2H) |
| 73 | 119-121 | ¹H NMR (400 MHz, CDCl$_3$) δ7.43 (dd, J = 7.9, 1.4 Hz, 1H), 7.19 (t, J = 7.9 Hz, 1H), 7.14 (dd, J = 8.0, 1.4 Hz, 1H), 5.01 (br s, 2H), 3.99 (s, 3H) |
| 74 | 153-156 | ¹H NMR (300 MHz, DMSO-$d_6$) δ 7.55 (dd, J = 7.9, 1.3 Hz, 1H), 7.46 (dd, J = 8.1, 1.2 Hz, 1H), 7.36 (t, J = 8.0 Hz, 1H), 7.10 (br s, 2H) |

TABLE 3-continued

Analytical Data for Compounds in Table 1

| C. No. | MP (° C.) | $^1$H NMR |
|---|---|---|
| 75 | 160-162 | $^1$H NMR (400 MHz, CDCl$_3$) δ 7.41 (d, J = 8.8 Hz, 1H), 7.20 (d, J = 8.8 Hz, 1H), 5.01 (s, 2H), 3.99 (s, 3H) |
| 76 | 157-159 | $^1$H NMR (400 MHz, DMSO-d$_6$) δ 7.50 (dd, J = 9.1, 4.9 Hz, 1H), 7.40 (dd, J = 17.0, 7.7 Hz, 1H), 7.19 (s, 2H), 3.88 (s, 3H) |
| 77 | 161-162 | $^1$H NMR (400 MHz, DMSO-d$_6$) δ 13.45 (d, J = 233.5 Hz, 1H), 7.52 (dd, J = 9.1, 4.9 Hz, 1H), 7.40 (dd, J = 17.4, 8.2 Hz, 1H), 7.12 (d, J = 21.0 Hz, 2H) |
| 78 | 151-153 | $^1$H NMR (400 MHz, CDCl$_3$) δ 7.35 (s, 1H), 7.34 (s, 1H), 5.02 (s, 2H), 3.99 (s, 3H) |
| 79 | 156-159 | $^1$H NMR (400 MHz, CDCl$_3$) δ 7.50 (d, J = 8.6 Hz, 1H), 7.23 (d, J = 8.6 Hz, 1H), 5.02 (s, 2H), 3.99 (s, 3H) |
| 80 | 168-170 | $^1$H NMR (400 MHz, DMSO-d$_6$) δ 13.84 (s, 1H), 7.60 (d, J = 8.7 Hz, 1H), 7.45 (d, J = 8.7 Hz, 1H), 7.11 (s, 2H) |
| 81 | 169-170 (dec) | $^1$H NMR (400 MHz, DMSO-d$_6$) δ 13.54 (d, J = 165.0 Hz, 1H), 7.70 (d, J = 8.5 Hz, 1H), 7.28 (d, J = 8.5 Hz, 1H), 7.09 (s, 2H) |
| 82 | 173-175 | $^1$H NMR (400 MHz, DMSO-d$_6$) δ 13.71 (s, 1H), 7.51 (s, 1H), 7.12 (s, 1H) |
| 83 | 159-161 | $^1$H NMR (400 MHz, CDCl$_3$) δ 7.11 (dd, J = 8.9, 4.9 Hz, 1H), 6.79 (m, 1H), 6.09 (s, 2H), 4.91 (s, 2H), 3.98 (s, 3H) |
| 84 | 129 | $^1$H NMR (300 MHz, CDCl$_3$) δ 7.93 (dd, J = 8.1, 1.4 Hz, 1H), 7.34 (s, 1H), 7.15 (t, J = 8.0 Hz, 1H), 7.07 (dd, J = 7.9, 1.4 Hz, 1H), 4.96 (s, 2H), 4.01 (s, 3H) |
| 85 | 170 | $^1$H NMR (300 MHz, DMSO-d$_6$) δ 7.88 (dd, J = 8.2, 1.2 Hz, 1H), 7.48 (dd, J = 8.0, 1.2 Hz, 1H), 7.39 (s, 1H), 7.33 (t, J = 8.1 Hz, 1H), 6.93 (s, 2H) |
| 86 | 172-174 | $^1$H NMR (400 MHz, CDCl$_3$) δ 7.97 (d, J = 8.9 Hz, 1H), 7.33 (s, 1H), 7.17 (d, J = 8.9 Hz, 1H), 4.92 (s, 2H), 4.01 (s, 3H) |
| 87 | 182-184 | $^1$H NMR (400 MHz, DMSO-d$_6$) δ 13.58 (s, 1H), 7.91 (d, J = 9.0 Hz, 1H), 7.45 (d, J = 8.9 Hz, 1H), 7.35 (s, 1H), 6.89 (s, 2H) |
| 88 | 142-143 | $^1$H NMR (400 MHz, CDCl$_3$) δ 7.98 (dd, J = 9.3, 5.0 Hz, 1H), 7.30 (s, 1H), 7.00 (dd, J = 11.3, 7.1 Hz, 1H), 4.92 (s, 2H), 4.01 (s, 3H) |
| 89 | 168-169 | $^1$H NMR (400 MHz, DMSO-d$_6$) δ 13.46 (d, J = 154.8 Hz, 1H), 7.91 (dd, J = 9.3, 5.1 Hz, 1H), 7.36 (t, J = 9.5 Hz, 1H), 7.32 (s, 1H), 6.89 (s, 2H) |
| 90 | | $^1$H NMR (400 MHz, DMSO-d$_6$) δ 7.52 (dd, J = 8.9, 4.0 Hz, 1H), 7.22 (dd, J = 11.0, 9.0 Hz, 1H), 7.06 (d, J = 1.4 Hz, 1H), 6.99 (s, 2H), 3.88 (s, 3H) |
| 91 | 163-164 | $^1$H NMR (400 MHz, DMSO-d$_6$) δ 13.51 (s, 1H), 7.52 (dd, J = 9.0, 4.0 Hz, 1H), 7.22 (dd, J = 11.1, 9.0 Hz, 1H), 7.02 (d, J = 1.4 Hz, 1H), 6.88 (s, 2H) |
| 92 | 175-178 | $^1$H NMR (400 MHz, CDCl$_3$) δ 7.71 (dd, J = 9.1, 5.1 Hz, 1H), 7.40 (s, 1H), 6.77 (t, J = 9.3 Hz, 1H), 6.13 (s, 2H), 4.79 (s, 2H), 4.00 (s, 3H) |
| 93 | 40-50 | $^1$H NMR (400 MHz, CDCl$_3$) δ 7.71 (dd, J = 8.1, 1.3 Hz, 1H), 7.47 (s, 1H), 6.93 (t, J = 7.9 Hz, 1H), 6.86 (dd, J = 7.7, 1.3 Hz, 1H), 6.06 (s, 2H), 4.78 (s, 2H), 4.00 (s, 3H) |
| 94 | 181-186 | $^1$H NMR (400 MHz, CDCl$_3$) δ 7.20 (q, J = 8.6 Hz, 2H), 4.90 (s, 2H), 3.97 (s, 3H), 2.12 (s, 3H) |
| 95 | 154-156 | $^1$H NMR (400 MHz, CDCl$_3$) δ7.91 (d, J = 8.9 Hz, 1H), 7.13 (d, J = 8.9 Hz, 1H), 5.42 (s, 2H), 4.02 (s, 3H), 3.93 (s, 3H) |
| 96 | 187-189 | $^1$H NMR (400 MHz, DMSO-d$_6$) δ7.93 (d, J = 8.9 Hz, 1H), 7.45 (d, J = 9.0 Hz, 1H), 7.42 (br s, 2H), 3.76 (s, 3H) |
| 97 | 206-208 | $^1$H NMR (400 MHz, CDCl$_3$) δ 7.65 (dd, J = 9.2, 5.1 Hz, 1H), 6.74 (t, J = 9.3 Hz, 1H), 6.19 (s, 2H), 5.40 (s, 2H), 4.01 (s, 3H), 3.92 (s, 3H) |
| 98 | 142-144 | $^1$H NMR (400 MHz, CDCl$_3$) δ 7.64 (dd, J = 6.8, 2.7 Hz, 1H), 6.89 (m, 2H), 6.11 (s, 2H), 5.40 (s, 2H), 4.01 (s, 3H), 3.93 (s, 3H) |
| 99 | 129-131 | $^1$H NMR (400 MHz, CDCl$_3$) δ 7.91 (dd, J = 7.4, 2.1 Hz, 1H), 7.13 (m, 2H), 5.45 (s, 2H), 4.02 (s, 3H), 3.94 (s, 3H) |
| 100 | 150-154 | $^1$H NMR (400 MHz, CDCl$_3$) δ 7.42 (dt, J = 7.7, 1.6 Hz, 1H), 7.33 (s, 1H), 7.28 (s, 1H), 4.88 (s, 2H), 4.62 (q, J = 8.4 Hz, 2H), 3.98 (d, J = 3.0 Hz, 3H), 3.31-3.18 (m, 2H) |
| 101 | 166-168 | $^1$H NMR (400 MHz, DMSO-d$_6$) δ 7.33 (q, J = 7.8 Hz, 2H), 7.18 (s, 1H), 6.89 (d, J = 16.4 Hz, 2H), 4.58 (t, J = 8.7 Hz, 2H), 3.23 (t, J = 8.7 Hz, 2H) |
| 102 | 135-138 | $^1$H NMR (300 MHz, CDCl$_3$) δ 7.33 (d, J = 7.6 Hz, 1H), 7.26 (dd, J = 7.3, 1.2 Hz, 1H), 6.94 (t, J = 7.5 Hz, 1H), 4.87 (s, 2H), 4.60 (t, J = 8.7 Hz, 2H), 3.96 (s, 3H), 3.26 (t, J = 8.7 Hz, 2H) |
| 103 | 153-156 | $^1$H NMR (400 MHz, CDCl$_3$) δ 7.81-7.86 (m, 2H), 7.33 (d, J = 8 Hz, 1H), 5.16 (br d, J = 4 Hz, 1H), 4.89 (br s, 2H), 3.97 (s, 3H) |
| 104 | 172-174 | $^1$H NMR (400 MHz, DMSO-d$_6$) δ 13.61 (br s, 1H), 7.76-7.83 (m, 2H), 7.46 (d, J = 8 Hz, 1H), 6.89 (br s, 2H), 5.08 (br s, 4H) |
| 105 | 113-115 | $^1$H NMR (400 MHz, CDCl$_3$) δ 7.79 (m, 1H), 7.60 (dt, J = 8.4, 1.8 Hz, 1H), 6.89 (d, J = 8.4 Hz, 1H), 5.74 (d, J = 3.7 Hz, 2H), 4.89 (s, 2H), 3.98 (d, J = 7.5 Hz, 3H) |
| 106 | 170-171 | $^1$H NMR (400 MHz, CDCl$_3$) δ 7.88 (dd, J = 8.1, 6.1 Hz, 1H), 7.43 (dq, J = 8.1, 1.2 Hz, 1H), 7.21 (d, J = 1.7 Hz, 1H), 4.95 (s, 2H), 4.01 (s, 3H) |

TABLE 3-continued

Analytical Data for Compounds in Table 1

| C. No. | MP (° C.) | $^1$H NMR |
|---|---|---|
| 107 | 120-122 | $^1$H NMR (400 MHz, CDCl$_3$) δ 7.68-7.73 (m, 2H), 6.49 (d, J = 9 Hz, 1H), 4.77 (br s, 2H), 3.96 (s, 3H), 3.37 (t, J = 8.5 Hz, 2H), 2.99 (t, J = 8.5 Hz, 2H), 2.77 (s, 3H) |
| 108 | 161-163 | $^1$H NMR (400 MHz, DMSO-d$_6$) δ 13.43 (br s, 1H), 7.56-7.62 (m, 2H), 6.69 (br s, 2H), 6.57 (d, J = 9 Hz, 1H), 3.37 (t, J = 8 Hz, 2H), 2.96 (t, J = 8 Hz, 2H), 2.77 (s, 3H) |

Examples of Herbicidal Activities

Herbicidal evaluations were made visually on a scale of 0 to 100 where 0 represents no activity and 100 represents complete plant death. The data is displayed as indicated in Table 4.

TABLE 4

Percent Control Rating Conversion Table

| Rating | % Control |
|---|---|
| A | 95-100 |
| B | 85-94 |
| C | 75-84 |
| D | 60-74 |
| E | 45-59 |
| F | 30-44 |
| G | 0-29 |

Example A

Evaluation of Postemergent Herbicidal Activity

Post-Emergent Test I:

Seeds of test species were obtained from commercial suppliers and planted into a 5"-round pot containing soil-less media mix (Metro-Mix 360®, Sun Gro Horticulture). Postemergence treatments were planted 8-12 days (d) prior to application and cultured in a greenhouse equipped with supplemental light sources to provide a 16 h photoperiod at 24-29° C. All pots were surface irrigated.

Approximately 10 milligrams (mg) of each compound were dissolved in 1.3 mL acetone-DMSO (97:3, volume per volume (v/v)) and diluted with 4.1 mL water-isopropanol-crop oil concentrate (78:20:2, v/v/v) containing 0.02% Triton X-155. Treatments were serial diluted with the above formulation solvent to provide 1.85, 0.926, 0.462 and 0.231 milligrams per milliliter (mg/mL) of test compound delivered in 2.7 mL/pot (roughly equivalent to 4.0, 2.0, 1.0, and 0.5 kg/ha, respectively). Formulated compounds were applied using a DeVilbiss® compressed air sprayer at 2-4 pounds per square inch (psi). Following treatment, pots were returned to the greenhouse for the duration of the experiment. All pots were sub-irrigated as needed to provide optimum growing conditions. All pots were fertilized one time per week by subirrigating with Peters Peat-Lite Special® fertilizer (20-10-20).

Phytotoxicity ratings were obtained 10 days after treatment postemergence applications. All evaluations were made visually on a scale of 0 to 100 where 0 represents no activity and 100 represents complete plant death and are presented as indicated in Table 4.

Some of the compounds tested, application rates employed, plant species tested, and results are given in Table 5.

TABLE 5

Post-Emergent Test I Herbicidal Activity on Key Broadleaf and Grass Weed as well as Crop Species

| | Application Rate | Visual Growth Reduction (%) 10 Days After Application | | | | |
|---|---|---|---|---|---|---|
| C. No. | (kg ai/ha) | AVEFA | ECHCG | HELAN | IPOHE | SETFA |
| 3 | 4 | C | C | C | C | C |
| 5 | 4 | G | G | A | A | C |
| 51 | 4 | G | G | D | G | G |
| 54 | 4 | G | G | D | G | G |
| 71 | 4 | G | G | A | C | G |
| 72 | 4 | G | G | A | G | G |
| 73 | 3.96 | G | G | A | C | G |
| 74 | 3.96 | G | n/t | A | D | G |

AVEFA: wild oats (*Avena fatua*)
ECHCG: barnyardgrass (*Echinochloa crus-galli*)
HELAN: sunflower (*Helianthus annuus*)
IPOHE: ivyleaf morningglory (*Ipomoea hederecea*)
SETFA: giant foxtail (*Setaria faberi*)
kg ai/ha: kilograms active ingredient per hectare
n/t: not tested

Example B

Evaluation of Preemergent Herbicidal Activity

Pre-Emergent Test I:

Seeds of test species were planted into round plastic pots (5-inch diameter) containing sandy loam soil. After planting, all pots were sub-irrigated 16 h prior to compound application.

Compounds were dissolved in a 97:3 v/v mixture of acetone and DMSO and diluted to the appropriate concentration in a final application solution containing water, acetone, isopropanol, DMSO and Agri-dex (crop oil concentrate) in a 59:23:15:1.0:1.5 v/v ratio and 0.02% w/v (weight/volume) of Triton X-155 to obtain the spray solution containing the highest application rate. The high application rate was serial diluted with the above application solution to provide delivery of the compound at rates ½×, ¼× and ⅛× of the highest rate (equivalent to 4.0, 2.0, 1.0, and 0.5 kg/ha, respectively).

Formulated compound (2.7 mL) was applied pipetted evenly over the soil surface followed by incorporation with water (15 mL). Following treatment, pots were returned to the greenhouse for the duration of the experiment. The greenhouse was programmed for an approximate 15 h photoperiod which was maintained at about 23-29° C. during the day and 22-28° C. during the night. Nutrients and water were added on a regular basis through surface irrigation and supplemental lighting was provided with overhead metal halide 1000-Watt lamps as necessary.

Herbicidal effect ratings were obtained 14 days after treatment. All evaluations were made relative to appropriate controls on a scale of 0 to 100 where 0 represents no herbicidal effect and 100 represents plant death or lack of emergence from the soil and are presented as indicated in Table 4.

Some of the compounds tested, application rates employed, plant species tested, and results are given in Table 6.

TABLE 6

Pre-Emergent Test I Herbicidal Activity on Key
Broadleaf and Grass Weed as well as Crop Species

| Compound Number | Application Rate (kg ai/ha) | Visual Growth Reduction (%) 14 Days After Application | | | | |
|---|---|---|---|---|---|---|
| | | AVEFA | ECHCG | HELAN | IPOHE | SETFA |
| 71 | 4 | F | F | A | E | G |
| 72 | 4 | D | C | A | G | G |
| 73 | 3.96 | G | G | A | C | G |
| 74 | 3.96 | D | A | A | D | E |

AVEFA: wild oats (*Avena fatua*)
ECHCG: barnyardgrass (*Echinochloa crus-galli*)
HELAN: sunflower (*Helianthus annuus*)
IPOHE: ivyleaf morningglory (*Ipomoea hederecea*)
SETFA: giant foxtail (*Setaria faberi*)
kg ai/ha: kilograms active ingredient per hectare Example C Evaluation of Postemergent Herbicidal Activity Post-Emergent Test II:

Seeds or nutlets of the desired test plant species were planted in Sun Gro Metro-Mix® 360 planting mixture, which typically has a pH of 6.0 to 6.8 and an organic matter content of about 30 percent, in plastic pots with a surface area of 64 square centimeters ($cm^2$). When required to ensure good germination and healthy plants, a fungicide treatment and/or other chemical or physical treatment was applied. The plants were grown for 7-21 d in a greenhouse with an approximate 15 h photoperiod which was maintained at about 23-29° C. during the day and 22-28° C. during the night. Nutrients and water were added on a regular basis and supplemental lighting was provided with overhead metal halide 1000-Watt lamps as necessary. The plants were employed for testing when they reached the first or second true leaf stage.

A weighed amount, determined by the highest rate to be tested, of each test compound was placed in a 25 mL glass vial and was dissolved in 4 mL of a 97:3 v/v mixture of acetone and DMSO to obtain concentrated stock solutions. If the test compound did not dissolve readily, the mixture was warmed and/or sonicated. The concentrated stock solutions obtained were diluted with 20 mL of an aqueous mixture containing acetone, water, isopropyl alcohol, DMSO, Atplus 411F crop oil concentrate, and Triton® X-155 surfactant in a 48.5:39:10:1.5:1.0:0.02 v/v ratio to obtain spray solutions containing the highest application rates. Additional application rates were obtained by serial dilution of 12 mL of the high rate solution into a solution containing 2 mL of a 97:3 v/v mixture of acetone and DMSO and 10 mL of an aqueous mixture containing acetone, water, isopropyl alcohol, DMSO, Atplus 411F crop oil concentrate, and Triton X-155 surfactant in a 48.5:39:10:1.5:1.0:0.02 v/v ratio to obtain ½×, ¼×, ⅛× and ¹⁄₁₆× rates of the high rate. Compound requirements are based upon a 12 mL application volume at a rate of 187 liters per hectare (L/ha). Formulated compounds were applied to the plant material with an overhead Mandel track sprayer equipped with 8002E nozzles calibrated to deliver 187 L/ha over an application area of 0.503 square meters at a spray height of 18 inches (43 cm) above the average plant canopy height. Control plants were sprayed in the same manner with the solvent blank.

The treated plants and control plants were placed in a greenhouse as described above and watered by subirrigation to prevent wash-off of the test compounds. After 14 d, the condition of the test plants as compared with that of the untreated plants was determined visually and scored on a scale of 0 to 100 percent where 0 corresponds to no injury and 100 corresponds to complete kill and are presented as indicated in Table 4.

Some of the compounds tested, application rates employed, plant species tested, and results are given in Table 7.

TABLE 7

Post-Emergent Test II Herbicidal Activity on Key
Broadleaf Weed and Crop Species

| C. No. | Application Rate (g ai/ha) | Visual Growth Reduction (%) 14 Days After Application | | | | | |
|---|---|---|---|---|---|---|---|
| | | ABUTH | AMARE | BRSNN | CHEAL | EPHHL | HELAN |
| 1 | 35 | G | G | G | G | G | B |
| | 70 | G | G | G | G | G | B |
| | 140 | G | G | G | G | G | B |
| 3 | 35 | G | G | G | G | G | G |
| | 70 | G | A | G | G | G | G |
| | 140 | G | A | G | E | G | B |
| 4 | 35 | G | G | G | G | G | G |
| | 70 | G | G | G | G | G | E |
| | 140 | G | G | G | G | G | D |
| 5 | 35 | G | G | E | G | G | F |
| | 70 | G | G | D | G | G | F |
| | 140 | G | G | D | G | G | E |
| 6 | 35 | A | C | C | A | B | B |
| | 70 | A | C | B | A | B | B |
| | 140 | A | A | B | A | A | A |
| 7 | 35 | B | C | B | A | A | A |
| | 70 | B | A | B | A | A | A |
| | 140 | A | A | A | A | A | A |
| 8 | 35 | A | G | D | E | A | G |
| | 70 | A | E | D | C | A | E |
| | 140 | A | D | C | B | A | B |
| 9 | 35 | C | G | C | B | C | B |
| | 70 | B | G | B | B | B | B |
| | 140 | A | G | A | B | B | A |
| 10 | 35 | B | B | C | B | A | B |
| | 70 | A | A | B | B | A | B |
| | 140 | A | A | B | A | A | B |
| 11 | 35 | B | n/t | B | A | A | A |
| | 70 | B | n/t | B | A | A | A |
| | 140 | A | n/t | B | A | A | A |
| 12 | 35 | G | G | G | G | G | G |
| | 70 | G | G | G | G | G | G |
| | 140 | D | G | G | G | G | G |
| 13 | 35 | D | G | G | D | E | B |
| | 70 | C | G | F | B | C | B |
| | 140 | C | G | E | B | A | B |
| 14 | 140 | G | G | G | C | G | B |
| 15 | 35 | G | G | G | G | G | G |
| | 70 | G | G | G | E | G | G |
| | 140 | G | E | G | C | G | G |
| 16 | 35 | D | B | F | E | A | B |
| | 70 | D | B | D | D | A | A |
| | 140 | C | A | B | D | A | A |
| 17 | 35 | G | G | G | G | G | G |
| | 70 | G | G | G | G | G | G |
| | 140 | G | G | G | G | G | G |

TABLE 7-continued

Post-Emergent Test II Herbicidal Activity on Key Broadleaf Weed and Crop Species

| C. No. | Application Rate (g ai/ha) | ABUTH | AMARE | BRSNN | CHEAL | EPHHL | HELAN |
|---|---|---|---|---|---|---|---|
| 18 | 35 | G | G | G | G | G | G |
|  | 70 | G | G | G | G | G | G |
|  | 140 | G | G | G | G | G | E |
| 19 | 35 | G | B | G | G | A | G |
|  | 70 | D | B | E | G | A | G |
|  | 140 | D | B | D | G | A | F |
| 20 | 35 | F | D | G | G | E | D |
|  | 70 | D | A | G | F | B | C |
|  | 140 | A | A | F | C | B | B |
| 21 | 35 | G | G | G | G | G | E |
|  | 70 | G | G | G | G | G | E |
|  | 140 | G | G | G | G | G | D |
| 22 | 35 | G | G | G | G | F | B |
|  | 70 | G | G | G | G | E | B |
|  | 140 | G | G | G | G | E | B |
| 23 | 35 | G | G | G | G | A | C |
|  | 70 | G | G | C | G | A | B |
|  | 140 | G | G | B | G | A | B |
| 24 | 35 | G | G | G | G | C | G |
|  | 70 | G | G | G | G | A | G |
|  | 140 | G | G | G | G | A | G |
| 25 | 35 | E | G | C | G | A | G |
|  | 70 | D | G | A | G | A | G |
|  | 140 | C | G | A | E | A | G |
| 26 | 35 | G | G | E | G | A | B |
|  | 70 | G | G | D | G | A | A |
|  | 140 | G | B | C | G | A | A |
| 27 | 35 | G | G | G | G | G | F |
|  | 70 | G | G | G | G | G | C |
|  | 140 | G | G | G | G | G | B |
| 28 | 35 | G | G | G | G | A | B |
|  | 70 | G | G | G | G | A | B |
|  | 140 | D | G | D | G | A | A |
| 30 | 35 | E | G | E | G | D | G |
|  | 70 | C | G | D | G | C | G |
|  | 140 | C | G | C | G | B | B |
| 31 | 35 | G | B | G | G | A | E |
|  | 70 | G | B | G | G | A | B |
|  | 140 | E | A | E | G | A | B |
| 32 | 35 | B | G | D | A | G | C |
|  | 70 | B | E | D | A | D | C |
|  | 140 | B | C | C | A | D | C |
| 33 | 35 | D | D | D | C | G | C |
|  | 70 | C | C | D | C | D | B |
|  | 140 | C | A | D | C | D | B |
| 34 | 35 | E | B | C | C | E | C |
|  | 70 | D | A | C | C | D | B |
|  | 140 | C | A | B | C | D | B |
| 35 | 35 | G | B | F | G | G | D |
|  | 70 | C | A | E | D | G | B |
|  | 140 | C | A | D | B | G | A |
| 36 | 35 | G | A | G | G | G | C |
|  | 70 | G | A | F | E | G | C |
|  | 140 | G | A | E | E | G | B |
| 37 | 35 | A | B | B | A | A | G |
|  | 70 | A | A | A | A | A | F |
|  | 140 | A | A | A | A | A | C |
| 38 | 35 | G | G | G | G | G | G |
|  | 70 | G | D | G | G | G | G |
|  | 140 | G | D | G | G | G | D |
| 40 | 35 | G | G | G | G | G | G |
|  | 70 | G | A | G | G | G | G |
|  | 140 | G | A | G | G | G | G |
| 41 | 35 | D | A | D | B | A | G |
|  | 70 | C | A | C | B | A | D |
|  | 140 | C | A | C | B | A | D |
| 42 | 35 | B | A | A | B | A | E |
|  | 70 | B | A | A | B | A | D |
|  | 140 | B | A | A | B | A | C |
| 44 | 35 | G | G | G | G | G | G |
|  | 70 | G | G | G | G | G | G |
|  | 140 | G | G | G | G | G | G |
| 45 | 35 | A | A | C | B | C | D |
|  | 70 | A | A | A | A | B | D |
|  | 140 | A | A | A | A | A | C |
| 46 | 35 | B | A | A | A | F | G |
|  | 70 | A | A | A | A | D | F |
|  | 140 | A | A | A | A | B | D |
| 47 | 35 | G | G | D | F | G | F |
|  | 70 | F | C | D | F | G | F |
|  | 140 | D | B | D | E | G | E |
| 48 | 35 | B | B | A | A | A | G |
|  | 70 | A | A | A | A | A | E |
|  | 140 | A | A | A | A | A | D |
| 49 | 35 | G | G | G | G | G | B |
|  | 70 | G | G | G | F | G | B |
|  | 140 | F | G | G | B | G | A |
| 52 | 35 | G | G | G | G | G | B |
|  | 70 | G | G | G | G | G | A |
|  | 140 | G | G | G | G | G | A |
| 55 | 35 | C | E | G | E | A | E |
|  | 70 | C | B | G | D | A | D |
|  | 140 | C | A | G | C | A | C |
| 56 | 35 | G | G | G | G | D | B |
|  | 70 | G | G | G | G | A | B |
|  | 140 | G | G | G | G | A | B |
| 57 | 35 | G | G | G | G | G | E |
|  | 70 | G | G | G | G | D | B |
|  | 140 | G | B | G | G | A | A |
| 58 | 35 | G | G | G | A | A | C |
|  | 70 | G | E | G | A | A | C |
|  | 140 | C | A | D | A | A | C |
| 59 | 35 | G | E | D | C | A | D |
|  | 70 | G | B | B | B | A | C |
|  | 140 | D | A | B | B | A | C |
| 60 | 35 | F | G | E | D | C | C |
|  | 70 | D | F | D | C | C | C |
|  | 140 | C | E | D | B | B | C |
| 61 | 35 | E | G | D | D | B | D |
|  | 70 | D | F | B | D | A | D |
|  | 140 | D | F | C | C | A | C |
| 62 | 35 | E | G | E | G | A | B |
|  | 70 | B | G | E | G | A | C |
|  | 140 | B | G | D | G | A | A |
| 63 | 35 | B | G | D | G | A | B |
|  | 70 | D | F | C | G | A | B |
|  | 140 | B | D | C | G | A | B |
| 64 | 35 | G | G | G | G | C | G |
|  | 70 | G | G | G | G | B | D |
|  | 140 | G | G | G | G | A | C |
| 66 | 35 | C | A | D | E | A | C |
|  | 70 | C | A | C | B | A | B |
|  | 140 | B | A | B | A | A | A |
| 67 | 35 | G | G | G | G | D | G |
|  | 70 | G | G | G | G | A | G |
|  | 140 | G | G | G | G | A | G |
| 68 | 35 | G | G | G | G | C | F |
|  | 70 | G | G | G | G | A | E |
|  | 140 | G | G | G | G | A | D |
| 69 | 35 | G | G | C | G | G | G |
|  | 70 | G | G | C | G | D | E |
|  | 140 | G | G | A | G | C | D |
| 70 | 35 | E | A | D | C | G | B |
|  | 70 | C | A | D | B | G | A |
|  | 140 | C | A | C | A | G | A |
| 71 | 35 | D | D | F | A | G | B |
|  | 70 | C | A | B | A | G | A |
|  | 140 | A | A | B | A | G | A |
|  | 280 | A | A | A | A | G | A |

TABLE 7-continued

Post-Emergent Test II Herbicidal Activity on Key Broadleaf Weed and Crop Species

| C. No. | Application Rate (g ai/ha) | ABUTH | AMARE | BRSNN | CHEAL | EPHHL | HELAN |
|---|---|---|---|---|---|---|---|
| 72 | 35 | C | A | C | A | G | A |
|  | 70 | A | A | A | A | G | A |
|  | 140 | A | A | A | A | G | A |
|  | 280 | A | A | A | A | G | A |
| 73 | 35 | C | A | B | A | G | C |
|  | 70 | C | A | A | A | G | B |
|  | 140 | B | A | A | A | G | A |
| 74 | 35 | G | A | C | B | G | C |
|  | 70 | F | A | B | A | G | C |
|  | 140 | E | A | A | A | G | B |
| 75 | 35 | B | A | C | A | G | A |
|  | 70 | A | A | B | A | G | A |
|  | 140 | A | A | A | A | G | A |
| 76 | 35 | D | A | D | B | G | B |
|  | 70 | C | A | C | B | G | B |
|  | 140 | B | A | B | A | G | B |
| 77 | 35 | F | A | C | B | G | B |
|  | 70 | D | A | B | A | G | A |
|  | 140 | C | A | A | A | G | A |
| 78 | 35 | B | A | D | A | G | A |
|  | 70 | B | A | C | A | G | A |
|  | 140 | B | A | C | A | G | A |
| 79 | 35 | D | A | D | B | G | B |
|  | 70 | C | A | D | B | G | B |
|  | 140 | C | A | D | B | G | B |
| 80 | 35 | D | A | B | A | G | B |
|  | 70 | C | A | B | A | G | B |
|  | 140 | B | A | B | A | G | B |
| 81 | 35 | G | A | C | B | G | B |
|  | 70 | D | A | B | B | G | B |
|  | 140 | C | A | A | B | G | B |
| 82 | 35 | F | A | A | A | G | B |
|  | 70 | D | A | A | A | G | B |
|  | 140 | C | A | A | A | G | A |
| 83 | 35 | B | A | F | A | G | B |
|  | 70 | B | A | A | A | G | A |
|  | 140 | A | A | A | A | G | A |
| 84 | 35 | E | A | D | B | G | G |
|  | 70 | D | A | C | B | G | F |
|  | 140 | C | A | B | A | G | F |
| 86 | 35 | C | A | C | A | G | C |
|  | 70 | B | A | C | A | G | B |
|  | 140 | B | A | B | A | G | B |
| 87 | 35 | C | A | D | A | G | C |
|  | 70 | B | A | C | A | G | C |
|  | 140 | B | A | B | A | G | C |
| 88 | 35 | D | A | D | B | G | F |
|  | 70 | B | A | D | B | G | D |
|  | 140 | B | A | C | A | G | D |
| 89 | 35 | G | A | B | A | G | D |
|  | 70 | C | A | B | A | G | D |
|  | 140 | C | A | A | A | G | C |
| 90 | 35 | D | A | G | B | G | G |
|  | 70 | C | A | G | A | G | G |
|  | 140 | B | A | D | A | G | G |
| 91 | 35 | D | A | G | A | G | G |
|  | 70 | C | A | E | A | G | G |
|  | 140 | C | A | D | A | G | G |
| 92 | 35 | D | A | F | A | G | D |
|  | 70 | B | A | D | B | G | D |
|  | 140 | B | A | C | A | G | C |
| 93 | 35 | G | G | G | D | G | E |
|  | 70 | G | G | F | C | G | D |
|  | 140 | E | D | D | A | G | C |
| 94 | 35 | F | A | G | C | G | D |
|  | 70 | E | A | G | B | G | B |
|  | 140 | E | A | G | B | G | A |
| 95 | 35 | E | A | E | A | G | A |
|  | 70 | C | A | E | A | G | A |
|  | 140 | C | A | D | A | G | A |
| 96 | 35 | C | A | G | A | G | A |
|  | 70 | D | A | C | A | G | A |
|  | 140 | B | A | B | A | G | A |
| 97 | 35 | G | G | G | D | G | D |
|  | 70 | G | G | G | B | G | C |
|  | 140 | G | G | G | D | G | B |
| 98 | 35 | G | G | G | E | G | G |
|  | 70 | G | G | G | D | G | F |
|  | 140 | G | F | G | D | G | D |
| 99 | 35 | G | G | G | D | G | C |
|  | 70 | G | G | G | C | G | B |
|  | 140 | G | G | G | B | G | B |
| 100 | 35 | E | C | G | A | A | D |
|  | 70 | B | A | G | A | A | D |
|  | 140 | A | A | G | A | A | C |
| 101 | 35 | C | A | G | A | G | B |
|  | 70 | B | A | B | A | G | B |
|  | 140 | A | A | A | A | F | B |
| 102 | 35 | G | n/t | G | A | G | C |
|  | 70 | G | n/t | G | A | G | B |
|  | 140 | E | n/t | G | A | G | B |
| 103 | 35 | G | G | G | E | G | C |
|  | 70 | G | G | G | B | G | C |
|  | 140 | G | G | G | A | G | C |
| 104 | 35 | G | G | G | E | G | E |
|  | 70 | G | G | G | B | G | C |
|  | 140 | G | G | G | B | G | C |
| 105 | 35 | G | G | G | F | D | B |
|  | 70 | G | G | F | F | C | B |
|  | 140 | G | E | D | D | B | A |
| 106 | 35 | E | F | G | G | E | G |
|  | 70 | C | F | G | G | D | G |
|  | 140 | C | D | G | E | C | G |
|  | 280 | B | C | G | C | C | F |
| 107 | 140 | D | G | G | B | A | G |
| 108 | 140 | G | G | G | D | G | D |
| 110 | 140 | C | A | G | C | D | B |

ABUTH: velvetleaf (*Abutilon theophrasti*)
AMARE: redroot pigweed (*Amaranthus retroflexus*)
BRSNN: oilseed rape, canola (*Brassica napus*)
CHEAL: lambsquarters (*Chenopodium album*)
EPHHL: wild poinsettia (*Euphorbia heterophylla*)
HELAN: sunflower (*Helianthus annuus*)
g ai/ha: grams active ingredient per hectare
n/t: not tested

TABLE 8

Post-Emergent Test II Herbicidal Activity on Key
Grass and Sedge Weeds as well as Grass Crops

| C. No. | Application Rate (g ai/ha) | Visual Growth Reduction (%) 14 Days After Application | | | | | |
|---|---|---|---|---|---|---|---|
| | | CYPES | ECHCG | SETFA | ORYSA | TRZAS | ZEAMX |
| 1 | 35 | G | E | G | G | G | D |
| | 70 | G | D | E | G | G | D |
| | 140 | G | D | E | G | G | D |
| 3 | 35 | G | G | G | G | G | G |
| | 70 | G | G | G | G | G | G |
| | 140 | G | G | G | G | G | G |
| 4 | 35 | G | G | G | G | G | G |
| | 70 | G | G | G | G | G | G |
| | 140 | G | G | G | G | G | G |
| 5 | 35 | G | G | G | G | G | G |
| | 70 | G | G | G | G | G | G |
| | 140 | G | G | G | G | G | G |
| 6 | 35 | A | A | D | F | E | B |
| | 70 | A | A | C | E | D | B |
| | 140 | A | A | B | E | D | B |
| 7 | 35 | A | A | A | F | E | A |
| | 70 | A | A | A | F | D | A |
| | 140 | A | A | A | D | D | A |
| 8 | 35 | A | A | B | G | G | A |
| | 70 | A | A | A | G | F | A |
| | 140 | A | A | A | F | F | A |
| 9 | 35 | A | B | E | G | F | D |
| | 70 | A | B | D | G | E | D |
| | 140 | A | A | C | G | D | C |
| 10 | 35 | A | A | C | G | E | D |
| | 70 | A | A | A | G | D | C |
| | 140 | A | A | A | G | D | C |
| 11 | 35 | G | B | C | G | D | D |
| | 70 | A | A | B | G | D | D |
| | 140 | A | A | A | F | C | C |
| 12 | 35 | G | G | G | G | G | G |
| | 70 | G | G | G | G | G | G |
| | 140 | G | G | G | G | G | G |
| 13 | 35 | E | C | C | G | E | D |
| | 70 | C | A | C | G | D | D |
| | 140 | A | B | B | G | D | C |
| 14 | 140 | G | G | G | G | G | G |
| 15 | 35 | G | G | G | G | G | G |
| | 70 | G | G | G | G | G | G |
| | 140 | G | G | G | G | G | G |
| 16 | 35 | G | D | D | G | G | F |
| | 70 | E | D | D | G | F | E |
| | 140 | E | C | D | G | E | C |
| 17 | 35 | G | n/t | n/t | G | G | G |
| | 70 | G | n/t | n/t | G | G | G |
| | 140 | G | n/t | n/t | G | G | D |
| 18 | 35 | G | E | E | G | G | G |
| | 70 | G | D | E | G | E | F |
| | 140 | G | D | D | G | E | D |
| 19 | 35 | A | B | G | G | G | D |
| | 70 | A | B | G | G | G | D |
| | 140 | A | A | G | G | G | D |
| 20 | 35 | E | D | E | G | G | F |
| | 70 | C | C | C | F | G | E |
| | 140 | B | B | B | F | G | D |
| 21 | 35 | G | G | G | G | G | G |
| | 70 | G | G | G | G | G | G |
| | 140 | G | G | D | G | G | E |
| 22 | 35 | A | G | n/t | G | G | G |
| | 70 | A | G | n/t | G | E | D |
| | 140 | A | E | n/t | G | D | C |
| 23 | 35 | G | C | D | G | E | D |
| | 70 | E | A | C | G | E | D |
| | 140 | E | A | C | G | D | D |
| 24 | 35 | A | D | G | G | G | D |
| | 70 | A | B | G | G | G | C |
| | 140 | A | A | G | G | F | C |
| 25 | 35 | A | B | E | G | E | D |
| | 70 | A | B | D | F | E | C |
| | 140 | A | A | D | D | D | C |

TABLE 8-continued

Post-Emergent Test II Herbicidal Activity on Key
Grass and Sedge Weeds as well as Grass Crops

| C. No. | Application Rate (g ai/ha) | CYPES | ECHCG | SETFA | ORYSA | TRZAS | ZEAMX |
|---|---|---|---|---|---|---|---|
| 26 | 35 | G | E | G | G | G | E |
|  | 70 | G | D | G | G | G | E |
|  | 140 | G | C | G | G | G | D |
| 27 | 35 | G | G | G | G | G | G |
|  | 70 | G | G | G | G | G | G |
|  | 140 | G | G | G | G | G | F |
| 28 | 35 | A | D | G | G | G | D |
|  | 70 | A | C | E | G | G | D |
|  | 140 | A | C | D | G | F | C |
| 30 | 35 | G | C | G | G | G | E |
|  | 70 | A | C | G | G | G | D |
|  | 140 | A | C | G | G | G | C |
| 31 | 35 | G | G | G | G | G | G |
|  | 70 | G | D | G | G | G | F |
|  | 140 | G | C | G | G | G | E |
| 32 | 35 | A | D | n/t | G | E | D |
|  | 70 | A | C | n/t | G | D | D |
|  | 140 | A | C | n/t | G | D | C |
| 33 | 35 | A | n/t | G | G | G | D |
|  | 70 | n/t | n/t | G | G | G | D |
|  | 140 | A | n/t | E | G | G | C |
| 34 | 35 | G | n/t | C | G | E | D |
|  | 70 | G | n/t | C | G | D | D |
|  | 140 | G | n/t | C | G | D | D |
| 35 | 35 | G | G | G | G | G | G |
|  | 70 | F | G | G | G | G | G |
|  | 140 | A | G | G | G | G | F |
| 36 | 35 | G | n/t | G | G | G | G |
|  | 70 | G | n/t | F | G | G | G |
|  | 140 | G | n/t | E | G | G | G |
| 37 | 35 | A | A | D | G | G | D |
|  | 70 | A | A | A | G | G | C |
|  | 140 | A | A | A | G | G | B |
| 38 | 35 | G | G | G | G | G | G |
|  | 70 | G | G | G | G | G | G |
|  | 140 | G | G | G | G | G | G |
| 40 | 35 | G | G | n/t | G | G | G |
|  | 70 | G | G | n/t | G | G | G |
|  | 140 | G | G | n/t | G | G | E |
| 41 | 35 | G | C | C | G | F | D |
|  | 70 | G | B | B | G | F | C |
|  | 140 | G | A | B | G | E | C |
| 42 | 35 | A | A | D | F | D | D |
|  | 70 | A | A | C | F | D | C |
|  | 140 | A | A | C | F | D | C |
| 44 | 35 | G | D | G | G | G | G |
|  | 70 | G | D | G | G | G | G |
|  | 140 | G | C | G | G | G | G |
| 45 | 35 | F | C | D | E | F | E |
|  | 70 | F | C | D | D | E | D |
|  | 140 | D | B | B | D | D | C |
| 46 | 35 | A | E | G | G | G | G |
|  | 70 | A | D | G | G | F | E |
|  | 140 | A | B | G | G | E | C |
| 47 | 35 | G | G | G | G | G | G |
|  | 70 | G | G | G | G | G | G |
|  | 140 | G | G | G | G | G | G |
| 48 | 35 | G | C | G | F | G | F |
|  | 70 | G | C | D | E | F | D |
|  | 140 | F | B | C | D | D | C |
| 49 | 35 | G | G | G | G | G | F |
|  | 70 | G | G | G | G | F | D |
|  | 140 | G | G | G | G | F | D |
| 52 | 35 | G | E | G | G | G | D |
|  | 70 | G | D | G | G | F | D |
|  | 140 | G | C | E | G | F | D |
| 55 | 35 | G | C | C | G | G | D |
|  | 70 | G | C | B | G | G | D |
|  | 140 | G | C | B | G | G | D |
| 56 | 35 | G | C | D | G | G | E |
|  | 70 | E | C | C | G | F | D |
|  | 140 | E | A | C | G | F | C |

TABLE 8-continued

Post-Emergent Test II Herbicidal Activity on Key
Grass and Sedge Weeds as well as Grass Crops

| C. No. | Application Rate (g ai/ha) | Visual Growth Reduction (%) 14 Days After Application | | | | | |
|---|---|---|---|---|---|---|---|
| | | CYPES | ECHCG | SETFA | ORYSA | TRZAS | ZEAMX |
| 57 | 35 | G | B | E | G | G | G |
| | 70 | G | A | G | G | G | F |
| | 140 | G | A | E | G | F | E |
| 58 | 35 | D | C | F | G | G | E |
| | 70 | D | B | E | G | G | D |
| | 140 | D | A | E | G | G | C |
| 59 | 35 | G | C | E | G | G | D |
| | 70 | G | C | D | G | G | D |
| | 140 | B | n/t | D | G | G | D |
| 60 | 35 | C | D | F | G | E | D |
| | 70 | B | C | D | G | D | C |
| | 140 | B | B | C | G | D | B |
| 61 | 35 | G | B | D | G | D | n/t |
| | 70 | G | B | C | E | C | n/t |
| | 140 | E | B | B | D | C | n/t |
| 62 | 35 | A | B | G | G | G | A |
| | 70 | A | B | F | G | G | A |
| | 140 | A | A | D | G | G | A |
| 63 | 35 | A | n/t | C | G | E | A |
| | 70 | A | A | A | G | E | A |
| | 140 | A | A | A | G | E | A |
| 64 | 35 | F | G | G | G | G | F |
| | 70 | D | E | E | G | F | E |
| | 140 | B | C | C | G | F | C |
| 66 | 35 | G | A | C | F | E | D |
| | 70 | A | A | C | F | D | D |
| | 140 | A | A | B | F | D | C |
| 67 | 35 | G | G | G | G | G | G |
| | 70 | G | E | E | G | G | D |
| | 140 | E | C | D | G | G | D |
| 68 | 35 | G | D | D | G | G | E |
| | 70 | G | D | D | G | E | D |
| | 140 | G | C | D | G | E | C |
| 69 | 35 | G | G | G | G | G | G |
| | 70 | G | G | G | G | G | G |
| | 140 | G | G | G | G | G | G |
| 70 | 35 | G | G | G | G | G | n/t |
| | 70 | G | G | G | G | G | n/t |
| | 140 | G | G | G | G | G | n/t |
| 71 | 35 | G | G | G | G | G | G |
| | 70 | G | G | G | G | G | G |
| | 140 | F | G | G | G | G | G |
| | 280 | E | G | G | G | G | G |
| 72 | 35 | G | G | G | G | G | G |
| | 70 | G | G | G | G | G | G |
| | 140 | G | G | G | G | G | G |
| | 280 | G | G | G | G | G | G |
| 73 | 35 | G | G | G | G | G | G |
| | 70 | E | G | G | G | G | G |
| | 140 | E | G | G | G | G | G |
| 74 | 35 | G | G | G | G | G | n/t |
| | 70 | G | G | G | G | G | n/t |
| | 140 | G | G | G | G | G | n/t |
| 75 | 35 | G | G | G | G | G | A |
| | 70 | G | G | G | G | G | A |
| | 140 | E | G | G | G | G | A |
| 76 | 35 | G | G | G | G | F | G |
| | 70 | F | G | G | G | E | G |
| | 140 | F | G | G | G | D | G |
| 77 | 35 | G | G | G | G | E | G |
| | 70 | G | G | G | G | D | G |
| | 140 | G | G | G | G | D | G |
| 78 | 35 | G | G | G | G | G | D |
| | 70 | G | G | G | G | G | D |
| | 140 | G | G | G | G | G | D |

TABLE 8-continued

Post-Emergent Test II Herbicidal Activity on Key
Grass and Sedge Weeds as well as Grass Crops

| C. No. | Application Rate (g ai/ha) | Visual Growth Reduction (%) 14 Days After Application | | | | | |
|---|---|---|---|---|---|---|---|
| | | CYPES | ECHCG | SETFA | ORYSA | TRZAS | ZEAMX |
| 79 | 35 | G | G | G | G | G | G |
| | 70 | G | G | G | G | G | G |
| | 140 | G | G | G | G | G | G |
| 80 | 35 | G | G | G | G | G | E |
| | 70 | G | G | G | G | G | D |
| | 140 | G | G | G | G | G | D |
| 81 | 35 | G | G | G | G | G | G |
| | 70 | G | G | G | G | G | G |
| | 140 | G | G | G | G | G | G |
| 82 | 35 | G | G | G | G | D | E |
| | 70 | F | G | G | F | D | D |
| | 140 | E | G | G | F | C | D |
| 83 | 35 | G | G | G | G | G | G |
| | 70 | G | G | G | G | G | G |
| | 140 | G | G | G | G | G | G |
| 84 | 35 | G | G | G | G | G | n/t |
| | 70 | G | G | G | G | G | n/t |
| | 140 | G | G | G | G | G | n/t |
| 86 | 35 | D | G | G | G | G | B |
| | 70 | D | G | G | G | G | B |
| | 140 | D | G | G | G | G | A |
| 87 | 35 | G | G | G | G | G | G |
| | 70 | G | G | G | G | G | G |
| | 140 | G | G | G | G | G | G |
| 88 | 35 | F | G | G | G | G | G |
| | 70 | D | G | G | G | E | G |
| | 140 | C | G | G | G | D | G |
| 89 | 35 | G | G | G | G | G | G |
| | 70 | G | G | G | G | G | G |
| | 140 | G | G | G | G | G | G |
| 90 | 35 | G | G | G | G | G | G |
| | 70 | G | G | G | G | G | G |
| | 140 | G | G | G | G | G | G |
| 91 | 35 | G | G | G | G | G | G |
| | 70 | G | G | G | G | G | G |
| | 140 | G | G | G | G | G | G |
| 92 | 35 | G | G | G | G | G | G |
| | 70 | G | G | G | G | G | G |
| | 140 | G | G | G | G | G | G |
| 93 | 35 | G | G | G | G | G | G |
| | 70 | G | G | G | G | G | G |
| | 140 | G | G | G | G | G | G |
| 94 | 35 | G | G | G | G | G | n/t |
| | 70 | G | G | G | G | G | n/t |
| | 140 | G | G | G | G | G | n/t |
| 95 | 35 | G | G | G | G | G | G |
| | 70 | E | G | G | G | G | G |
| | 140 | E | G | G | G | G | G |
| 96 | 35 | G | G | G | G | G | F |
| | 70 | G | G | G | G | F | D |
| | 140 | G | G | G | G | E | D |
| 97 | 35 | G | G | G | G | G | G |
| | 70 | G | G | G | G | G | G |
| | 140 | G | G | G | G | G | G |
| 98 | 35 | G | G | G | G | G | G |
| | 70 | G | G | G | G | G | G |
| | 140 | G | G | G | G | G | G |
| 99 | 35 | G | G | G | G | G | G |
| | 70 | G | G | G | G | G | G |
| | 140 | G | G | G | G | G | G |
| 100 | 35 | G | E | G | G | G | G |
| | 70 | G | C | G | G | G | A |
| | 140 | G | B | G | G | G | A |
| 101 | 35 | G | D | n/t | G | G | G |
| | 70 | G | D | n/t | G | G | G |
| | 140 | G | C | n/t | G | G | G |

TABLE 8-continued

Post-Emergent Test II Herbicidal Activity on Key
Grass and Sedge Weeds as well as Grass Crops

| C. No. | Application Rate (g ai/ha) | Visual Growth Reduction (%) 14 Days After Application | | | | | |
|---|---|---|---|---|---|---|---|
| | | CYPES | ECHCG | SETFA | ORYSA | TRZAS | ZEAMX |
| 102 | 35 | G | G | G | G | G | G |
| | 70 | G | G | G | G | G | G |
| | 140 | G | G | G | G | G | G |
| 103 | 35 | G | G | G | G | G | G |
| | 70 | G | G | G | G | G | G |
| | 140 | G | G | G | G | G | G |
| 104 | 35 | G | G | G | G | G | G |
| | 70 | G | G | G | G | G | G |
| | 140 | G | G | G | G | G | G |
| 105 | 35 | G | E | G | G | G | G |
| | 70 | G | D | G | G | G | G |
| | 140 | G | C | F | G | G | G |
| 106 | 35 | G | G | G | G | G | G |
| | 70 | G | G | G | G | G | G |
| | 140 | G | G | G | G | G | G |
| | 280 | G | G | G | G | G | G |
| 107 | 140 | G | G | G | G | G | G |
| 108 | 140 | G | C | G | G | G | G |
| 110 | 140 | E | G | G | G | G | G |

ECHCG: barnyardgrass (*Echinochloa crus-galli*)
CYPES: yellow nutsedge (*Cyperus esculentus*)
ORYSA: rice (*Oryza sativa*)
SETFA: giant foxtail (*Setaria faberi*)
TRZAS: wheat, spring (*Triticum aestivum*)
ZEAMX: maize, corn (*Zea mays*)
g ai/ha: grams active ingredient per hectare
n/t: not tested Example D Evaluation of Postemergent Herbicidal Activity in Wheat and Barley Post-Emergent Test III.

Seeds of the desired test plant species were planted in Sun Gro MetroMix® 306 planting mixture, which typically has a pH of 6.0 to 6.8 and an organic matter content of about 30 percent, in plastic pots with a surface area of 103.2 square centimeters ($cm^2$). When required to ensure good germination and healthy plants, a fungicide treatment and/or other chemical or physical treatment was applied. The plants were grown for 7-36 days (d) in a greenhouse with an approximate 14 hour (h) photoperiod which was maintained at about 18° C. during the day and 17° C. during the night. Nutrients and water were added on a regular basis and supplemental lighting was provided with overhead metal halide 1000-Watt lamps as necessary. The plants were employed for testing when they reached the second or third true leaf stage.

A weighed amount, determined by the highest rate to be tested, of each test compound was placed in a 25 mL glass vial and was dissolved in 4 mL of a 97:3 v/v mixture of acetone and DMSO to obtain concentrated stock solutions. If the test compound did not dissolve readily, the mixture was warmed and/or sonicated. The concentrated stock solutions obtained were diluted with 20 mL of an aqueous mixture containing acetone, water, isopropyl alcohol, DMSO, Agri-Dex crop oil concentrate, and X-77 surfactant in a 48:39:10:1.5:1.5:0.02 v/v ratio to obtain spray solutions containing the highest application rates. Additional application rates were obtained by serial dilution of 12 mL of the high rate solution into a solution containing 2 mL of a 97:3 v/v mixture of acetone and DMSO and 10 mL of an aqueous mixture containing acetone, water, isopropyl alcohol, DMSO, Agri-Dex crop oil concentrate, and X-77 surfactant in a 48:39:10:1.5:1.5:0.02 v/v ratio to obtain ½×, ¼×, ⅛× and ¹⁄₁₆× rates of the high rate. Compound requirements are based upon a 12 mL application volume at a rate of 187 liters per hectare (L/ha). Formulated compounds were applied to the plant material with an overhead Mandel track sprayer equipped with 8002E nozzles calibrated to deliver 187 L/ha over an application area of 0.503 square meters at a spray height of 18 inches (43 cm) above the average plant canopy height. Control plants were sprayed in the same manner with the solvent blank.

The treated plants and control plants were placed in a greenhouse as described above and watered by subirrigation to prevent wash-off of the test compounds. After 21 d, the condition of the test plants as compared with that of the untreated plants was determined visually and scored on a scale of 0 to 100 percent where 0 corresponds to no injury and 100 corresponds to complete kill and are presented as indicated in Table 4.

By applying the well-accepted probit analysis as described by J. Berkson in *Journal of the American Statistical Society*, 48, 565 (1953) and by D. Finney in "*Probit Analysis*" Cambridge University Press (1952), herbicidal injury of a specific compound at various rates can be used to calculate $GR_{20}$, $GR_{50}$, $GR_{80}$ and $GR_{90}$ values, which are defined as growth reduction factors that correspond to the effective dose of herbicide required to provide plant growth reduction (GR) of 20 percent, 50 percent, 80 percent and 90 percent, respectively. Probit analysis was applied to data collected from multiple dose rates of individual compounds utilizing the procedures explained in the following examples. The data for some of the dose rates and analysis of all of the dose rates are captured in the following tables.

Some of the compounds tested, application rates employed, plant species tested, and results are given in Tables 9 through 13.

TABLE 9

Activity of Herbicidal Compounds in Wheat and Barley

| C. No. | Application Rate (g ai/ha) | ALOMY | APESV | BROTE | LOLSS | PHAMI | SETVI | HORVS | TRZAS | BRSNW | GALAP | LAMPU | SINAR |
|---|---|---|---|---|---|---|---|---|---|---|---|---|---|
| | | | | | | | Visual Growth Reduction (%) 21 Days After Application | | | | | | |
| 7 | 17.5 | E | E | E | F | C | D | C | C | D | E | C | C |
| | 35 | B | D | D | E | B | C | B | B | C | D | B | B |
| | 70 | A | C | A | D | A | B | B | B | A | A | A | A |
| | $GR_{10}$ | — | — | — | — | — | — | 1 | 2 | 0.5 | — | — | — |
| | $GR_{20}$ | — | — | — | — | — | — | 2 | 3 | 1 | — | — | — |
| | $GR_{50}$ | 16 | 30 | 15 | >140 | 10 | 6 | — | — | 5 | 12 | 3 | 3 |
| | $GR_{80}$ | 25 | 114 | 37 | >140 | 24 | 13 | — | — | 24 | 31 | 12 | 15 |
| | $GR_{90}$ | 34 | >140 | 59 | >140 | 39 | 21 | — | — | 53 | 52 | 27 | 36 |

TABLE 10

Activity of Herbicidal Compounds in Wheat and Barley

| C. No. | Application Rate (g ai/ha) | HORVS | TRZAS | CIRAR | GALAP | KCHSC | LAMPU | MATCH | PAPRH | SASKR | SINAR | VERPE | VIOTR |
|---|---|---|---|---|---|---|---|---|---|---|---|---|---|
| | | | | | | Visual Growth Reduction (%) 21 Days After Application | | | | | | | |
| 78 | 17.5 | F | G | B | D | B | D | G | F | B | A | G | F |
| | 35 | E | F | B | D | A | C | F | D | n/a | A | D | F |
| | 70 | D | E | B | D | A | B | E | C | n/a | A | C | D |
| | $GR_{20}$ | 13 | 20 | — | — | — | — | — | — | — | — | — | — |
| | $GR_{50}$ | — | — | 2 | 1 | 2 | 2 | 63 | 44 | 0.4 | 1 | 33 | 47 |
| | $GR_{80}$ | — | — | 7 | >140 | 9 | 46 | >140 | >140 | 9 | 3 | 77 | >140 |
| | $GR_{90}$ | — | — | 12 | >140 | 19 | >140 | >140 | >140 | 42 | 8 | 119 | >140 |
| 82 | 17.5 | F | D | B | D | D | G | C | G | B | A | G | E |
| | 35 | D | D | B | B | C | G | C | G | B | A | G | D |
| | 70 | C | C | B | B | C | F | B | F | B | A | G | D |
| | $GR_{20}$ | 7 | 4 | — | — | — | — | — | — | — | — | — | — |
| | $GR_{50}$ | — | — | 1 | 10 | 2 | 89 | 18 | 113 | 1 | 0.02 | >140 | 31 |
| | $GR_{80}$ | — | — | 10 | 33 | 83 | 131 | 35 | >140 | 10 | 0.5 | >140 | 62 |
| | $GR_{90}$ | — | — | 34 | 64 | >140 | >140 | 49 | >140 | 32 | 2 | >140 | 90 |

TABLE 11

Activity of Herbicidal Compounds in Wheat and Barley

| C. No. | Application Rate (g ai/ha) | ALOMY | APESV | LOLSS | SETVI | KCHSC | HORVS | TRZAS |
|---|---|---|---|---|---|---|---|---|
| | | | | Visual Growth Reduction (%) 21 Days After Application | | | | |
| 8 | 17.5 | G | G | G | D | E | F | F |
| | 35 | F | B | G | C | D | D | D |
| | 70 | E | B | F | C | D | D | D |
| | $GR_{20}$ | — | — | — | — | — | 7 | 6 |
| | $GR_{50}$ | >70 | 22 | >70 | 11 | 21 | — | — |
| | $GR_{80}$ | >70 | 36 | >70 | 72 | >70 | — | — |
| | $GR_{90}$ | >70 | 46 | >70 | >70 | >70 | — | — |
| 9 | 17.5 | C | G | G | E | G | D | D |
| | 35 | B | D | G | C | G | B | C |
| | 70 | B | C | E | B | G | B | C |
| | $GR_{20}$ | — | — | — | — | — | 3 | 4 |
| | $GR_{50}$ | 13 | 30 | 70 | 21 | >70 | — | — |
| | $GR_{80}$ | 26 | 61 | >70 | 46 | >70 | — | — |
| | $GR_{90}$ | 38 | 89 | >70 | 71 | >70 | — | — |
| 10 | 35 | F | G | G | D | G | D | D |
| | 70 | E | E | F | C | D | C | B |
| | 140 | B | B | D | A | C | B | B |
| | $GR_{20}$ | — | — | — | — | — | 11 | 4 |
| | $GR_{50}$ | 52 | 65 | 93 | 36 | 78 | — | — |
| | $GR_{80}$ | 109 | 106 | >140 | 63 | 117 | — | — |
| | $GR_{90}$ | >140 | 138 | >140 | 85 | >140 | — | — |

TABLE 11-continued

Activity of Herbicidal Compounds in Wheat and Barley

| C. No. | Application Rate (g ai/ha) | Visual Growth Reduction (%) 21 Days After Application | | | | | | |
|---|---|---|---|---|---|---|---|---|
| | | ALOMY | APESV | LOLSS | SETVI | KCHSC | HORVS | TRZAS |
| 42 | 35 | B | D | E | C | E | C | C |
| | 70 | A | C | D | B | E | B | C |
| | 140 | A | B | D | A | D | B | B |
| | GR$_{20}$ | — | — | — | — | — | 0.50 | 0.20 |
| | GR$_{50}$ | 11 | 22 | 44 | 10 | 54 | — | — |
| | GR$_{80}$ | 25 | 81 | >140 | 46 | >140 | — | — |
| | GR$_{90}$ | 40 | >140 | >140 | >140 | >140 | — | — |
| 46 | 35 | D | G | G | G | B | E | D |
| | 70 | A | E | E | F | A | D | C |
| | 140 | A | D | D | D | A | B | B |
| | GR$_{20}$ | — | — | — | — | — | 8 | 10 |
| | GR$_{50}$ | 18 | 88 | 91 | 106 | 1 | — | — |
| | GR$_{80}$ | 35 | >140 | >140 | >140 | 7 | — | — |
| | GR$_{90}$ | 49 | >140 | >140 | >140 | 17 | — | — |

TABLE 12

Activity of Herbicidal Compounds in Wheat and Barley

| C. No. | Application Rate (g ai/ha) | Visual Growth Reduction (%) 21 Days After Application | | | | | | |
|---|---|---|---|---|---|---|---|---|
| | | ALOMY | APESV | LOLSS | SETVI | MATCH | VERPE | HORVS | TRZAS |
| 11 | 17.5 | F | F | E | E | G | E | D | C |
| | 35 | E | D | D | C | F | D | D | B |
| | 70 | D | B | C | B | E | B | B | B |
| | GR$_{20}$ | — | — | — | — | — | — | 3 | 0.12 |
| | GR$_{50}$ | 41 | 25 | 31 | 18 | 65 | 17 | — | — |
| | GR$_{80}$ | >70 | 52 | 62 | 37 | >70 | 41 | — | — |
| | GR$_{90}$ | >70 | >70 | >70 | 53 | >70 | 65 | — | — |
| 13 | 17.5 | E | G | G | D | G | C | D | D |
| | 35 | D | E | G | C | F | B | C | C |
| | 70 | A | D | G | A | D | A | B | C |
| | GR$_{20}$ | — | — | — | — | — | — | 2 | 2 |
| | GR$_{50}$ | 20 | >70 | >70 | 4 | 58 | 3 | — | — |
| | GR$_{80}$ | 40 | >70 | >70 | 20 | >70 | 16 | — | — |
| | GR$_{90}$ | 57 | >70 | >70 | 45 | >70 | 37 | — | — |

TABLE 13

Activity of Herbicidal Compounds in Wheat and Barley

| C. No. | Application Rate (g ai/ha) | Visual Growth Reduction (%) 21 Days After Application | | | | | |
|---|---|---|---|---|---|---|---|
| | | ALOMY | AVEFA | LOLSS | PHAMI | HORVS | TRZAS |
| 32 | 17.5 | B | E | G | G | E | D |
| | 35 | A | D | F | F | D | D |
| | 70 | A | D | D | E | D | C |
| | GR$_{20}$ | — | — | — | — | 3 | 1 |
| | GR$_{50}$ | 5 | 31 | 54 | 65 | — | — |

TABLE 13-continued

Activity of Herbicidal Compounds in Wheat and Barley

| C. No. | Application Rate (g ai/ha) | Visual Growth Reduction (%) 21 Days After Application | | | | | |
|---|---|---|---|---|---|---|---|
| | | ALOMY | AVEFA | LOLSS | PHAMI | HORVS | TRZAS |
| | $GR_{80}$ | 12 | >70 | >70 | >70 | — | — |
| | $GR_{90}$ | 18 | >70 | >70 | >70 | — | — |

ALOMY: black-grass (*Alopecurus myosuroides*)
APESV: bentgrass (*Apera spica-venti*)
BROTE: downy brome (*Bromus tectorum*)
HORVS: barley, spring (*Zea mays*)
TRZAS: wheat, spring (*Hordeum vulgare*)
LOLSS: ryegrass including, Italian ryegrass (*Lolium multiflorum*), rigid ryegrass (*Lolium rigidum*), annual ryegrass (*Lolium multiflorum* subsp. *Gaudini*)
PHAMI: lesser canary grass (*Phalaris minor*)
SETVI: green foxtail (*Setaria viridis*)
KCHSC: kochia (*Kochia scoparia*)
LAMPU: purple deadnettle (*Lamium purpureum*)
GALAP: cleavers (*Galium aparine*)
SINAR: wild mustard (*Sinapis arvensis*)
VERPE: bird's-eye speedwell (*veronica persica*)
BRSNW: oil seed rape, winter; canola, winter (*Brassica napus*)
PAPRH: common poppy (*Papaver rhoeas*)
SASKR: Russian thistle (*Salsola iberica*)
CIRAR: Canada thistle (*Cirsium arvense*)
VIOTR: wild pansy (*Viola tricolor*)
AVEFA: wild oat (*Avena fatua*)
MATCH: wild chamomile (*Matricaria recutita* L.)
g ai/ha: grams active ingredient per hectare
NT: Not tested
$GR_{20}$: Growth reduction of 20% of plant growth
$GR_{50}$: Growth reduction of 50% of plant growth
$GR_{80}$: Growth reduction of 80% of plant growth
$GR_{90}$: Growth reduction of 90% of plant growth Example E Evaluation of Postemergence Herbicidal Activity in Direct Seeded Rice Seeds or nutlets of the desired test plant species were planted in a soil matrix prepared by mixing a loam soil (43 percent silt, 19 percent clay, and 38 percent sand, with a pH of about 8.1 and an organic matter content of about 1.5 percent) and river sand in an 80 to 20 ratio. The soil matrix was contained in plastic pots with a surface area of 139.7 cm². When required to ensure good germination and healthy plants, a fungicide treatment and/or other chemical or physical treatment was applied. The plants were grown for 10-17 d in a greenhouse with an approximate 14-h photoperiod which was maintained at about 29° C. during the day and 26° C. during the night. Nutrients and water were added on a regular basis and supplemental lighting was provided with overhead metal halide 1000-Watt lamps as necessary. The plants were employed for testing when they reached the second or third true leaf stage.

A weighed amount, determined by the highest rate to be tested, of each test compound was placed in 25 mL glass vials and dissolved in a volume of 97:3 v/v acetone-DMSO to obtain 12× stock solutions. If the test compound did not dissolve readily, the mixture was warmed and/or sonicated. The concentrated stock solutions were added to the spray solutions so that the final acetone and DMSO concentrations were 16.2% and 0.5%, respectively. Spray solutions were diluted to the appropriate final concentrations with the addition of 10 mL of an aqueous mixture of 1.5% (v/v) Agri-dex crop oil concentrate. The final spray solutions contained 1.25% (v/v) Agri-dex crop oil concentrate. Compound requirements are based upon a 12 mL application volume at a rate of 187 L/ha. Formulated compounds were applied to the plant material with an overhead Mandel track sprayer equipped with 8002E nozzles calibrated to deliver 187 L/ha over an application area of 0.503 square meters (m²) at a spray height of 18 inches (43 cm) above average plant canopy height. Control plants were sprayed in the same manner with the solvent blank.

The treated plants and control plants were placed in a greenhouse as described above and watered by sub-irrigation to prevent wash-off of the test compounds. After 20-22 days, the condition of the test plants, compared with that of the untreated plants, was determined visually and scored on a scale of 0 to 100 percent where 0 corresponds to no injury and 100 corresponds to complete kill and are presented as indicated in Table 4.

By applying the well-accepted probit analysis as described by J. Berkson in *Journal of the American Statistical Society*, 48, 565 (1953) and by D. Finney in "*Probit Analysis*" Cambridge University Press (1952), herbicidal injury of a specific compound at various rates can be used to calculate $GR_{20}$, $GR_{50}$, $GR_{80}$ and $GR_{90}$ values, which are defined as growth reduction factors that correspond to the effective dose of herbicide required to provide plant growth reduction (GR) of 20 percent, 50 percent, 80 percent and 90 percent, respectively. Probit analysis was applied to data collected from multiple dose rates of individual compounds utilizing the procedures explained in the following examples. The data for some of the dose rates and analysis of all of the dose rates are captured in the following tables.

Some of the application rates and ratios employed, plant species tested, and results are given in Table 14.

TABLE 14

Activity of Herbicidal Compounds in Direct Seeded Rice

| C. No. | Application Rate (g ai/ha) | Visual Growth Reduction (%) 21 Days After Application | | | | | | |
|---|---|---|---|---|---|---|---|---|
| | | BRAPP | CYPDI | CYPES | CYPIR | DIGSA | ECHCG | ECHCO |
| 10 | 17.5 | B | A | A | A | A | A | B |
| | 35 | A | A | A | A | B | A | A |
| | 70 | A | A | A | A | A | A | A |
| | GR$_{20}$ | — | — | — | — | — | — | — |
| | GR$_{50}$ | 7 | 4 | <18 | 6 | 1 | 10 | 6 |
| | GR$_{80}$ | 16 | 8 | <18 | 10 | 8 | 14 | 14 |
| | GR$_{90}$ | 24 | 10 | <18 | 13 | 21 | 16 | 21 |
| 11 | 17.5 | B | A | B | A | A | A | A |
| | 35 | A | A | A | A | A | B | A |
| | 70 | A | A | A | A | A | A | A |
| | GR$_{20}$ | — | — | — | — | — | — | — |
| | GR$_{50}$ | 7 | 3 | <18 | 5 | 1 | 7 | 4 |
| | GR$_{80}$ | 16 | 7 | <18 | 7 | 4 | 15 | 9 |
| | GR$_{90}$ | 25 | 10 | <18 | 7 | 9 | 23 | 14 |
| 37 | 17.5 | D | A | C | B | B | B | B |
| | 35 | B | A | B | E | A | B | A |
| | 70 | A | A | A | A | A | A | A |
| | GR$_{20}$ | — | — | — | — | — | — | — |
| | GR$_{50}$ | 3 | 0.04 | <18 | 6 | 0.07 | 0.33 | 0.001 |
| | GR$_{80}$ | 15 | 1 | <18 | 23 | 2 | 4 | 0.2 |
| | GR$_{90}$ | 39 | 2 | <18 | 46 | 8 | 17 | 3 |
| 66 | 17.5 | B | A | A | A | C | A | A |
| | 35 | A | A | A | A | B | A | A |
| | 70 | A | A | A | A | B | A | A |
| | GR$_{20}$ | — | — | — | — | — | — | — |
| | GR$_{50}$ | 2 | 0.42 | 0.0001 | 9 | 2 | 3 | 2 |
| | GR$_{80}$ | 7 | 3 | 0.0001 | 15 | 21 | 7 | 6 |
| | GR$_{90}$ | 16 | 6 | 0.0001 | 19 | 77 | 12 | 11 |
| 25 | 17.5 | A | A | A | B | F | A | A |
| | 35 | A | A | A | A | D | A | A |
| | 70 | A | A | A | A | D | A | A |
| | GR$_{20}$ | — | — | — | — | — | — | — |
| | GR$_{50}$ | 4 | 0.04 | 0.04 | 2 | 27 | 0.025 | 2 |
| | GR$_{80}$ | 9 | 1 | 1 | 5 | 2530 | 1 | 4 |
| | GR$_{90}$ | 13 | 2 | 1 | 9 | 27000 | 3 | 6 |
| 13 | 17.5 | A | A | A | A | A | A | A |
| | 35 | A | A | A | A | A | B | A |
| | 70 | A | A | A | A | A | A | A |
| | GR$_{20}$ | — | — | — | — | — | — | — |
| | GR$_{50}$ | 3 | 0.04 | 0.04 | 0.04 | 0.05 | 0.01 | 1 |
| | GR$_{80}$ | 5 | 1 | 0 | 0 | 1 | 1 | 3 |
| | GR$_{90}$ | 7 | 2 | 0 | 0 | 6 | 10 | 6 |
| 41 | 17.5 | A | A | A | A | A | B | A |
| | 35 | A | A | A | A | A | A | A |
| | 70 | A | A | A | A | A | A | A |
| | GR$_{20}$ | — | — | — | — | — | — | — |
| | GR$_{50}$ | 0.3 | 4 | 0.0001 | 0.0001 | 0.001 | 0.0018 | 0.0003 |
| | GR$_{80}$ | 2 | 6 | 0.0001 | 0.0001 | 0.131 | 0.0018 | 0.0415 |
| | GR$_{90}$ | 6 | 7 | 0.0001 | 0.0001 | 2 | 0.0018 | 1 |
| 42 | 17.5 | A | A | A | A | A | A | A |
| | 35 | A | A | A | A | A | A | A |
| | 70 | A | A | A | A | A | A | A |
| | GR$_{20}$ | — | — | — | — | — | — | — |
| | GR$_{50}$ | 0.004 | 0.004 | 0.4 | 3 | 0.004 | 0.0001 | 0.00015 |
| | GR$_{80}$ | 0.2 | 0.2 | 2 | 5 | 0.158 | 0.0001 | 0.02070 |
| | GR$_{90}$ | 1 | 1 | 5 | 6 | 1 | 0.0001 | 0.268 |

| C. No. | Application Rate (g ai/ha) | Visual Growth Reduction (%) 21 Days After Application | | | | |
|---|---|---|---|---|---|---|
| | | LEFCH | ORYSJ | ORYSK | SCPJU | SEBEX |
| 10 | 17.5 | D | G | G | A | A |
| | 35 | A | D | E | A | A |
| | 70 | A | C | C | A | A |
| | GR$_{20}$ | — | 14 | 20 | — | — |
| | GR$_{50}$ | 12 | — | — | 0.0002 | 3 |
| | GR$_{80}$ | 20 | — | — | 0.0207 | 8 |
| | GR$_{90}$ | 27 | — | — | 0.268 | 13 |

TABLE 14-continued

Activity of Herbicidal Compounds in Direct Seeded Rice

| | | | | | | |
|---|---|---|---|---|---|---|
| 11 | 17.5 | G | F | E | A | A |
| | 35 | A | C | D | A | A |
| | 70 | A | B | C | A | A |
| | GR$_{20}$ | — | 8 | 7 | — | — |
| | GR$_{50}$ | 23 | — | — | 0.04 | 3 |
| | GR$_{80}$ | 34 | — | — | 1 | 7 |
| | GR$_{90}$ | 41 | — | — | 2 | 10 |
| 37 | 17.5 | G | G | G | A | C |
| | 35 | G | G | G | A | B |
| | 70 | E | F | G | A | A |
| | GR$_{20}$ | — | 56 | 70 | — | — |
| | GR$_{50}$ | 116 | — | — | 0.0001 | 2 |
| | GR$_{80}$ | 288 | — | — | 0.0001 | 15 |
| | GR$_{90}$ | 464 | — | — | 0.0001 | 47 |
| 66 | 17.5 | G | D | F | A | D |
| | 35 | G | B | D | A | A |
| | 70 | F | B | B | A | A |
| | GR$_{20}$ | — | 2 | 11 | — | — |
| | GR$_{50}$ | 105 | — | — | 0.0001 | 8 |
| | GR$_{80}$ | 227 | — | — | 0.0001 | 19 |
| | GR$_{90}$ | 339 | — | — | 0.0001 | 28 |
| 25 | 17.5 | G | B | B | A | G |
| | 35 | G | A | B | A | A |
| | 70 | G | A | A | A | A |
| | GR$_{20}$ | — | 1 | 3 | — | — |
| | GR$_{50}$ | 175 | — | — | 0.0001 | 19 |
| | GR$_{80}$ | 463 | — | — | 0.0001 | 26 |
| | GR$_{90}$ | 770 | — | — | 0.0001 | 30 |
| 13 | 17.5 | D | E | G | A | 95 |
| | 35 | A | B | E | A | 100 |
| | 70 | A | A | D | A | 100 |
| | GR$_{20}$ | — | 6 | 15 | — | — |
| | GR$_{50}$ | 14 | — | — | 0.0001 | 11 |
| | GR$_{80}$ | 25 | — | — | 0.0001 | 16 |
| | GR$_{90}$ | 33 | — | — | 0.0001 | 20 |
| 41 | 17.5 | B | B | D | A | A |
| | 35 | A | A | C | A | A |
| | 70 | A | A | B | A | A |
| | GR$_{20}$ | — | 1 | 2 | — | — |
| | GR$_{50}$ | 6 | — | — | 0.0001 | 4 |
| | GR$_{80}$ | 13 | — | — | 0.0001 | 9 |
| | GR$_{90}$ | 20 | — | — | 0.0001 | 13 |
| 42 | 17.5 | A | B | D | A | A |
| | 35 | A | A | C | A | A |
| | 70 | A | A | C | A | A |
| | GR$_{20}$ | — | 1 | 1 | — | — |
| | GR$_{50}$ | 4 | — | — | 0.0001 | 2 |
| | GR$_{80}$ | 8 | — | — | 0.0001 | 5 |
| | GR$_{90}$ | 13 | — | — | 0.0001 | 9 |

BRAPP: broadleaf signalgrass, *Brachiaria platyphylla*
CYPDI: small-flower flatsedge, *Cyperus difformis*
CYPES: yellow nutsedge, *Cyperus esculentus*
CYPIR: rice flatsedge, *Cyperus iria*
DIGSA: large crabgrass, *Digitaria sanguinalis*
ECHCG: barnyardgrass, *Echinochloa crus-galli*
ECHCO: junglerice, *Echinochloa colonum*
LEFCH: Chinese sprangletop, *Leptochloa chinensis*
SCPJU: Japanese bulrush, *Schoenoplectus juncoides* Roxb.
SEBEX: hemp sesbania, *Sesbania exaltata*
ORYSK: *Oryza sativa*
ORYSJ: *Oryza sativa*
g ai/ha: grams active ingredient per hectare

What is claimed is:

1. A compound of the Formula (I):

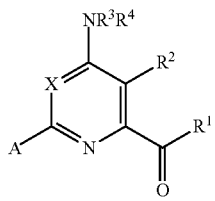
(I)

wherein

X is N or CY, wherein Y is hydrogen, halogen, $C_1$-$C_3$ alkyl, $C_1$-$C_3$ haloalkyl, $C_1$-$C_3$ alkoxy, $C_1$-$C_3$ haloalkoxy, $C_1$-$C_3$ alkoxy, $C_1$-$C_3$ alkylthio or $C_1$-$C_3$ haloalkylthio;

$R^1$ is $OR^{1'}$ or $NR^{1''}R^{1'}$, wherein $R^{1'}$ is hydrogen, $C_1$-$C_8$ alkyl, or $C_7$-$C_{10}$ arylalkyl, and $R^{1''}$ and $R^{1'}$ are independently hydrogen, $C_1$-$C_{12}$ alkyl, $C_3$-$C_{12}$ alkenyl, or $C_3$-$C_{12}$ alkynyl;

$R^2$ is halogen, $C_1$-$C_4$ alkyl, $C_1$-$C_4$ haloalkyl, $C_2$-$C_4$ alkenyl, $C_2$-$C_4$ haloalkenyl, $C_2$-$C_4$ alkynyl, $C_1$-$C_4$ alkoxy, $C_1$-$C_4$ haloalkoxy, $C_1$-$C_4$ alkylthio, $C_1$-$C_4$ haloalkylthio, amino, $C_1$-$C_4$ alkylamino, $C_2$-$C_4$ haloalkylamino, formyl, $C_1$-$C_3$ alkylcarbonyl, $C_1$-$C_3$ haloalkylcarbonyl, cyano, or a group of the formula —$CR^{17}$=$CR^{18}$—$SiR^{19}R^{20}R^{21}$, wherein $R^{17}$ is hydrogen, F, or $C_1$; $R^{18}$ is hydrogen, F, Cl, $C_1$-$C_4$ alkyl, or $C_1$-$C_4$ haloalkyl; and $R^{19}$, $R^{20}$, and $R^{21}$ are independently $C_1$-$C_{10}$ alkyl, $C_3$-$C_6$ cycloalkyl, phenyl, substituted phenyl, $C_1$-$C_{10}$ alkoxy, or OH;

$R^3$ and $R^4$ are independently hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamoyl, $C_1$-$C_6$ alkylsulfonyl, $C_1$-$C_6$ trialkylsilyl, $C_1$-$C_6$ dialkylphosphoryl, or $R^3$ and $R^4$ taken together with N is a 5- or 6-membered saturated ring, or $R^3$ and $R^4$ taken together represent =$CR^{3'}(R^{4'})$, wherein $R^{3'}$ and $R^{4'}$ are independently hydrogen, $C_1$-$C_6$ alkyl, $C_3$-$C_6$ alkenyl, $C_3$-$C_6$ alkynyl, $C_1$-$C_6$ alkoxy or $C_1$-$C_6$ alkylamino, or, $R^{3'}$ and $R^{4'}$ taken together with =C represent a 5- or 6-membered saturated ring;

A is one of groups Ar3 to Ar24:

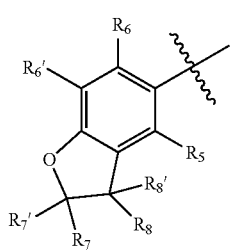
Ar4

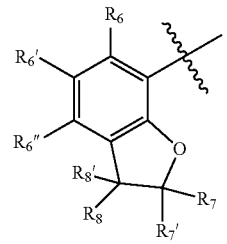
Ar5

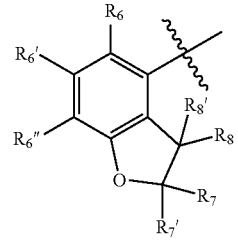
Ar6

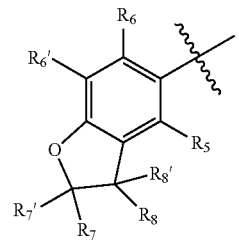
Ar4

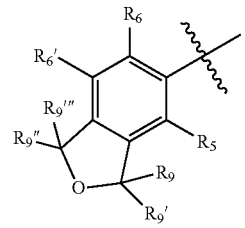
Ar7

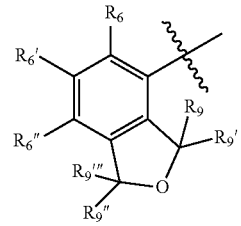
Ar8

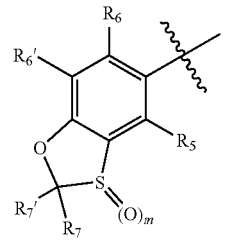
Ar9

-continued
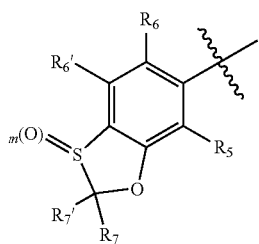
Ar10
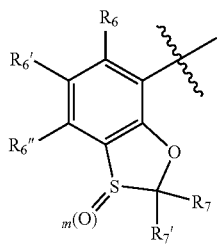
Ar11
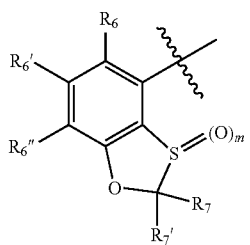
Ar12
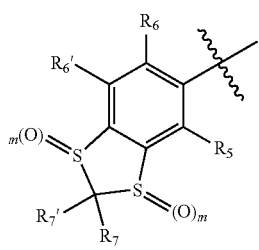
Ar13
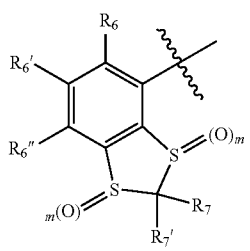
Ar14
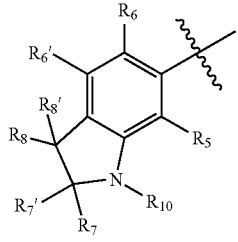
Ar15
-continued
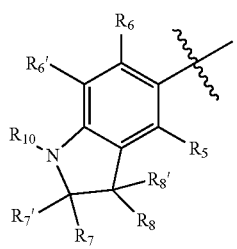
Ar16
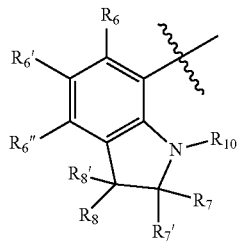
Ar17
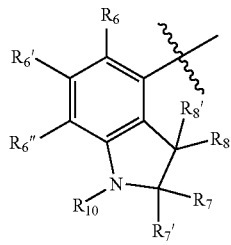
Ar18
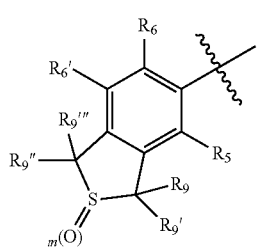
Ar19
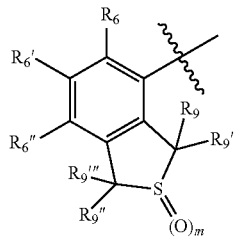
Ar20
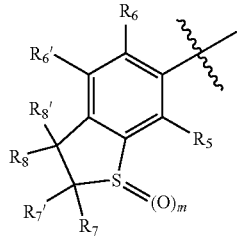
Ar21

-continued

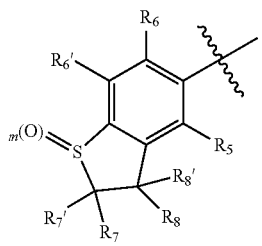
Ar22

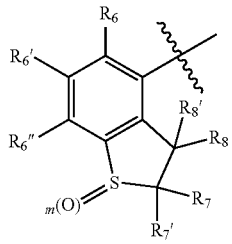
Ar23

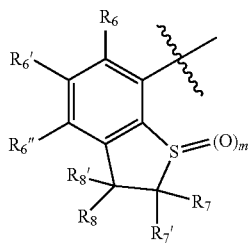
Ar24

R$^5$ is hydrogen, halogen, C$_1$-C$_4$ alkyl, C$_1$-C$_4$ haloalkyl, C$_1$-C$_3$ alkoxy, C$_1$-C$_3$ haloalkoxy, C$_1$-C$_3$ alkylthio, C$_1$-C$_3$ haloalkylthio, amino, C$_1$-C$_4$ alkylamino, or C$_2$-C$_4$ haloalkylamino.

R$^6$ is hydrogen, halogen, C$_1$-C$_4$ alkyl, C$_1$-C$_4$ haloalkyl, C$_1$-C$_3$ alkoxy, C$_1$-C$_3$ haloalkoxy, C$_1$-C$_3$ alkylthio, C$_1$-C$_3$ haloalkylthio, amino, C$_1$-C$_4$ alkylamino, or C$_2$-C$_4$ haloalkylamino;

R$^{6'}$ is hydrogen or halogen;

R$^{6''}$ is hydrogen, halogen, C$_1$-C$_4$ alkyl, C$_1$-C$_4$ haloalkyl, cyclopropyl, halocyclopropyl, C$_2$-C$_4$ alkenyl, C$_2$-C$_4$ haloalkenyl, C$_2$-C$_4$ alkynyl, C$_1$-C$_3$ alkoxy, C$_1$-C$_3$ haloalkoxy, C$_1$-C$_3$ alkylthio, C$_1$-C$_3$ haloalkylthio, amino, C$_1$-C$_4$ alkylamino, C$_2$-C$_4$ haloalkylamino, CN or NO$_2$;

R$^7$ and R$^{7'}$ are independently hydrogen, halogen, C$_1$-C$_4$ alkyl, C$_1$-C$_4$ haloalkyl, or C$_1$-C$_3$ alkoxy;

R$^8$ and R$^{8'}$ are independently hydrogen, halogen, C$_1$-C$_4$ alkyl, C$_1$-C$_4$ haloalkyl, or C$_1$-C$_3$ alkoxy;

R$^9$, R$^{9'}$, R$^{9''}$ and R$^{9'''}$ are independently hydrogen, halogen, C$_1$-C$_4$ alkyl, C$_1$-C$_4$ haloalkyl, or C$_1$-C$_3$ alkoxy;

R$^{10}$ is hydrogen, C$_1$-C$_6$ alkyl, C$_1$-C$_6$ haloalkyl, C$_3$-C$_6$ alkenyl, C$_3$-C$_6$ haloalkenyl, C$_3$-C$_6$ alkynyl, formyl, C$_1$-C$_3$ alkylcarbonyl, C$_1$-C$_3$ haloalkylcarbonyl, or C$_1$-C$_6$ trialkylsilyl;

or an N-oxide or an agriculturally acceptable salt thereof;

provided A is not

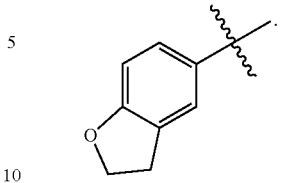

2. The compound of claim 1 wherein R$^2$ is halogen, C$_2$-C$_4$-alkenyl, C$_2$-C$_4$ haloalkenyl, or C$_1$-C$_4$-alkoxy.

3. The compound of claim 2 wherein R$^2$ is Cl, methoxy, vinyl, or 1-propenyl.

4. The compound of claim 1 wherein R$^3$ and R$^4$ are both hydrogen.

5. The compound of claim 1 wherein X is N, CH, or CF.

6. The compound of claim 1 wherein R$^5$ is hydrogen or halogen.

7. The compound of claim 6 wherein R$^5$ is hydrogen or F.

8. The compound of claim 1 wherein R$^6$ is hydrogen or F.

9. The compound of claim 1 wherein R$^{6'}$ is hydrogen.

10. The compound of claim 1 wherein:
R$^2$ is halogen, C$_2$-C$_4$-alkenyl, C$_2$-C$_4$ haloalkenyl, or C$_1$-C$_4$-alkoxy;
R$^3$ and R$^4$ are both hydrogen; and
X is N, CH, or CF.

11. The compound of claim 1 wherein:
R$^2$ is halogen, C$_2$-C$_4$-alkenyl, or C$_1$-C$_4$-alkoxy;
R$^3$ and R$^4$ are hydrogen; and
X is N, CH, or CF;
Ar is Ar7, Ar9, Ar10, Ar13, Ar15, Ar16, Ar19, Ar21, or Ar22;
R$^5$ is hydrogen or F;
R$^6$ is hydrogen or F;
R$^{6'}$ is hydrogen;
R$^7$, R$^{7'}$, R$^8$, R$^{8'}$, R$^9$, R$^{9'}$, R$^{9''}$, and R$^{9'''}$, if applicable to the relevant Ar group, are independently hydrogen or fluorine.

12. The compound of claim 1 wherein:
R$^2$ is chlorine, methoxy, vinyl, or 1-propenyl;
R$^3$ and R$^4$ are hydrogen; and
X is N, CH, or CF.

13. The compound of claim 1 wherein:
R$^2$ is chlorine;
R$^3$ and R$^4$ are hydrogen; and
X is N, CH, or CF.

14. The compound of claim 1 wherein:
R$^2$ is methoxy;
R$^3$ and R$^4$ are hydrogen; and
X is N, CH, or CF.

15. The compound of claim 1 wherein:
R$^2$ is vinyl or 1-propenyl;
R$^3$ and R$^4$ are hydrogen; and
X is N, CH, or CF.

16. A herbicidal composition comprising the compound of claim 1 and an agriculturally acceptable adjuvant or carrier.

17. The composition of claim 16, further comprising an additional herbicidal compound.

18. The composition of claim 16, further comprising a safener.

19. A method for controlling vegetation comprising applying a herbicidally effective amount of a compound of claim 1.

* * * * *